(12) United States Patent
Zhang et al.

(10) Patent No.: US 11,274,091 B2
(45) Date of Patent: Mar. 15, 2022

(54) CYCLOPENTANE COMPOUNDS

(71) Applicant: Dizal (Jiangsu) Pharmaceutical Co., Ltd., Wuxi (CN)

(72) Inventors: Xiaolin Zhang, Cambridge (GB); Weitao Pan, Cambridge (GB); Grigorios Nikitidis, Södertälje (SE); Jenny Susanna Marika Lindhagen, Södertälje (SE)

(73) Assignee: Dizal (Jiangsu) Pharmaceutical Co., Ltd., Wuxi (CN)

( * ) Notice: Subject to any disclaimer, the term of this patent is extended or adjusted under 35 U.S.C. 154(b) by 0 days.

(21) Appl. No.: 17/095,725

(22) Filed: Nov. 11, 2020

(65) Prior Publication Data

US 2021/0070733 A1   Mar. 11, 2021

Related U.S. Application Data

(63) Continuation of application No. PCT/EP2019/061888, filed on May 9, 2019.

(30) Foreign Application Priority Data

May 11, 2018  (WO) ................ PCT/CN2018/086503

(51) Int. Cl.
*C07D 401/08* (2006.01)
*A61P 13/12* (2006.01)

(52) U.S. Cl.
CPC ............ *C07D 401/08* (2013.01); *A61P 13/12* (2018.01); *C07B 2200/13* (2013.01)

(58) Field of Classification Search
CPC .................................................. C07D 401/08
See application file for complete search history.

(56) References Cited

U.S. PATENT DOCUMENTS

2013/0131034 A1*   5/2013   Follmann ................ A61P 35/00
514/210.01

* cited by examiner

*Primary Examiner* — Patricia L Morris
(74) *Attorney, Agent, or Firm* — Jun He Law Offices P.C.; Zhaohui Wang

(57) ABSTRACT

The present invention relates to cyclopentane compounds of Formula (I), physical forms thereof, processes for their production and their use in medicine.

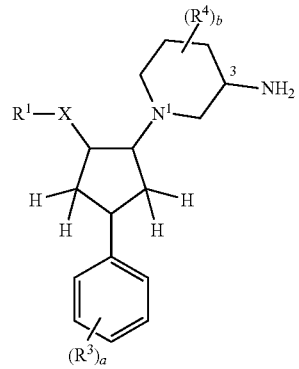

Formula (I)

9 Claims, 1 Drawing Sheet

X-Ray Powder Diffraction Pattern Compound 10, Form A
(y-axis = relative intensity)
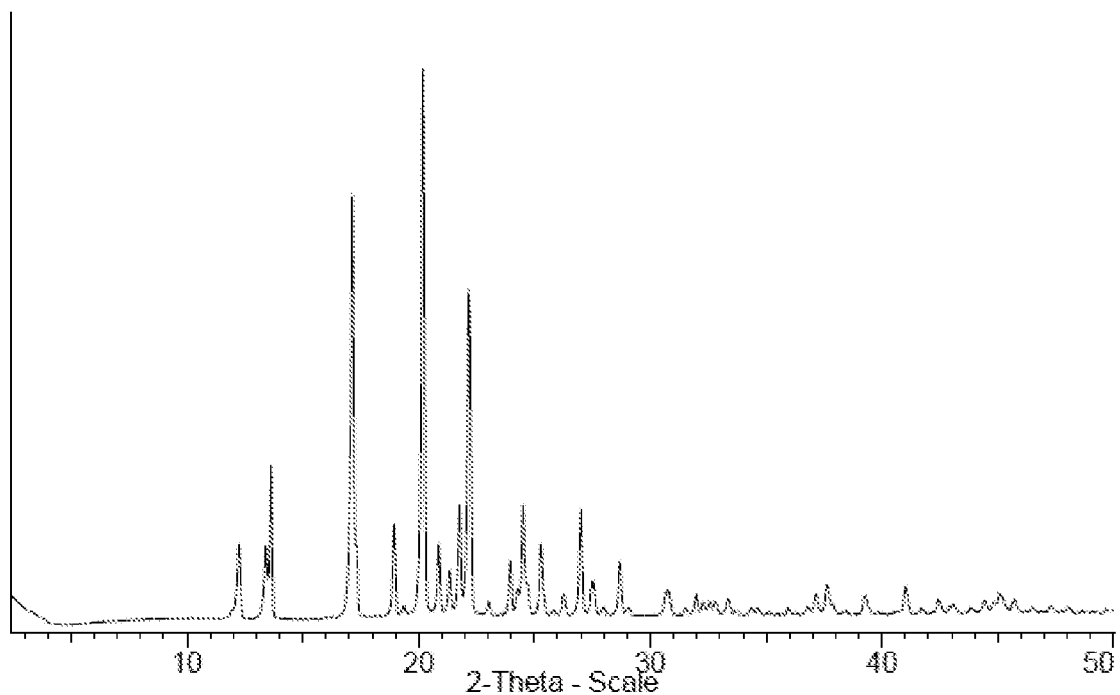

CYCLOPENTANE COMPOUNDS

CROSS-REFERENCE TO RELATED APPLICATIONS

This application is a Continuation of PCT Patent Application No. PCT/EP2019/061888, filed on May 9, 2019, which claims foreign priority of PCT Patent Application No. PCT/2018/086503, filed on May 11, 2018, now abandoned. Each of these applications is hereby incorporated by reference herein in its entirety.

The present disclosure relates to substituted cyclopentane compounds and pharmaceutically acceptable salts thereof that inhibit the canonical Transient receptor potential channels TRPC6 and TRPC3. The present disclosure also relates to the use of these compounds, and pharmaceutically acceptable salts thereof, in medicine, for example in the treatment of diseases in which inhibition of TRPC6 or TRPC3 function is of therapeutic significance. The present disclosure also relates to methods of treatment and methods of manufacture of medicaments using compounds according to the disclosure.

Transient receptor potential channels (TRP channels) are a group of ion channels located mostly on the plasma membrane of certain mammalian cells. TRP channels commonly modulate ion entry driving forces, and the $Ca^{2+}$ and $Mg^{2+}$ transport machinery, in the plasma membrane. The seven canonical Transient receptor potential channels (TRPC channels) are potential cation channels that are activated by phospholipase C (PLC)-coupled receptors and can be subdivided into four subgroups: group 1 (TRPC1), group 2 (TRPC2), group 3 (TRPC3, TRPC6 and TRPC7) and group 4 (TRPC4 and TRPC5). Of these, the group 3 TRPCs, i.e. TRPC3, TRPC6, and TRPC7, interact physically and, upon coexpression, coassemble to form functional tetrameric channels. The sequence homology between TRPCs 3, 6 and 7 is nearly 75%.

TRPC6, a member of the canonical transient receptor potential (TRPC) subfamily, is a non-selective $Ca^{2+}$ channel expressed on podocytes that has an important role in the maintenance of glomerular barrier function. Activation of TRPC6 results in $Ca^{2+}$ influx and regulates podocyte morphology and motility. Upregulation of the TRPC6 signaling has been observed to cause damage of podocytes, resulting in severe proteinuria.

Focal segmental glomerulosclerosis (FSGS) is the most common cause of steroid-resistant nephrotic syndrome in both children and adults. The prognosis of untreated patients with FSGS is poor, with more than 60% of untreated patients progressing to end stage renal disease (ESRD), also often referred to as kidney failure, that is, in turn, the last stage of chronic kidney disease. Typically, the time from FSGS diagnosis to ESRD is around 10 years. Progression to ESRD can however be much more rapid, for example within 6 months. Literature reports suggest that as many as 20% of ESRD patients initially present with FSGS.

TRPC6 gain of function mutations are identified in the familial or sporadic type of FSGS with the phenotype of proteinuria and resistance to steroid treatment, the standard of care for FSGS. Development of resistance to steroid treatment can in turn eventually lead to chronic kidney disease (CKD). A significant number of patients with FSGS present with a mutation of Transient receptor potential canonical 6 (TRPC6) that causes a gain of function (Winn et al, Science. 2005, 308 (5729):1801-4). Presence of TRPC6 gain-of-function mutations in FSGS are therefore of prognostic significance. Accordingly, inhibition of TRPC6 potentially offers a new opportunity for therapeutic intervention for the treatment of FSGS, especially for those patients with a TRPC6 gain of function mutation.

TRPC channel function has also been associated with a number of other disorders, with TRPC3 upregulation having been observed in muscular dystrophy and associated with myofibre degeneration (Millay et al PNAS, 2009, 106(45): 19023-19028). Other conditions that are associated with TRPC3 include cardiac hypertrophy (Kiyonaka et al, PNAS 2009, 106(13) 5400-5405). In addition to FSGS, TRPC6 has been associated with a range of conditions such as myocardial infarction (Varga-Szabo et al., J. Thromb. and Haemost. 2009, 7, 1057-1066) wherein loss of TRPC6 function has been linked to a slowing of the progression of cardiac dysfunction and cardiac remodelling in the post myocardial infarction heart in in vivo models (Gross et al, Circulation Research 2016, 119: A296); pulmonary hypertension (Yu et al, Circulation 2009, 119, 2313-22); skeletal muscle dysfunction (Millay et al, ibid); and cancer cell proliferation (Ding et al, J Natl Cancer Inst (2010) 102 (14): 1052-1068). TRPC6 and TRPC3 inhibitors therefore potentially have broad therapeutic application.

To the best of our knowledge, to date there have been no inhibitors of TRPC6 or TRPC3, nor dual inhibitors of TRPC6 and TRPC3 that have been approved for clinical use. Hence there is a need for new inhibitors of TRPC6 and/or TRPC3 with a pharmacological and pharmaceutical profile suitable for clinical use. It is an object of the present specification to provide new compounds that inhibit TRPC6 and TRPC3 that are suited for use as therapeutic agents.

We have now discovered, surprisingly, that the cyclopentane derivatives described herein are capable of inhibiting TRPC6 and TRPC3 and may therefore be useful for the treatment of conditions in which TRPC6 and TRPC3 function has pharmacological significance.

In one aspect, there is provided a compound of Formula I,

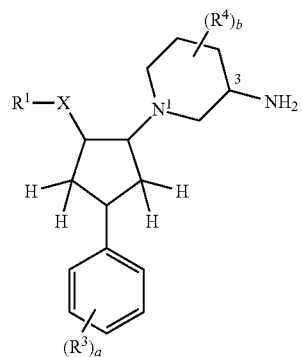

Formula I wherein:

X is a) O, and R is a 6-membered aromatic or heteroaromatic ring selected from phenyl, pyridyl, pyrimidyl, pyrazinyl or pyridazyl that is optionally substituted with one or two substituents Y that are independently selected from F, Cl, Br, CN, OH, $OC_{1-3}$alkyl, $OCF_3$, $C_{1-3}$alkyl, $C(O)NH_2$, $CF_3$ or cyclopropyl; or b) $NR^2$, and wherein N, $R^1$ and $R^2$ together form a 5-membered aromatic heterocycle that is optionally substituted with one or two substituents Y that are independently selected from F, Cl, CN, or Me;

$R^3$ is independently selected from F, Cl, CN, methyl, methoxy, hydroxy and ethynyl;

R[4] is independently selected from F or Cl attached to C2, C4 or C5 of the piperidine ring; and the integers a and b are independently selected from 0, 1 or 2;

or a pharmaceutically acceptable salt thereof.

In a further aspect, there is provided a pharmaceutical composition comprising a therapeutically effective amount of a compound of Formula I, or a pharmaceutically acceptable salt thereof, and at least one pharmaceutically acceptable diluent, excipient or inert carrier.

In a further aspect, there is provided a compound of Formula I or a pharmaceutically acceptable salt thereof, for use in treatment or prophylaxis of diseases and conditions in which inhibition of TRPC6 and/or TRPC3 is beneficial. In embodiments, the specification provides a compound of Formula I or a pharmaceutically acceptable salt thereof for use in the treatment of kidney disease. In embodiments, the kidney disease is focal segmental glomerulosclerosis (FSGS). In embodiments, the kidney disease is focal segmental glomerulosclerosis (FSGS) with a TRPC6 gain of function mutation.

In a further aspect, there is provided a method of treating diseases or conditions in which inhibition of TRPC6 and/or TRPC3 is beneficial, comprising administering to a patient in need thereof an effective amount of a compound of Formula I or a pharmaceutically acceptable salt thereof. In one embodiment, said disease or condition is kidney disease. In embodiments, the kidney disease is focal segmental glomerulosclerosis (FSGS). In embodiments, the kidney disease is focal segmental glomerulosclerosis (FSGS) with a TRPC6 gain of function mutation.

In a further aspect, there is provided the compound of Formula I or a pharmaceutically acceptable salt thereof, for use in the preparation of a medicine for the treatment of diseases or conditions in which inhibition of TRPC6 and/or TRPC3 is beneficial. In one embodiment, said disease or condition is kidney disease. In another embodiment, the kidney disease is focal segmental glomerulosclerosis (FSGS). In embodiments, the kidney disease is focal segmental glomerulosclerosis (FSGS) with a TRPC6 gain of function mutation.

In a further aspect, is provided a compound of Formula I, or a pharmaceutically acceptable salt thereof, for use in medicine.

In further aspect, there is provided a process for the preparation of a compound of Formula I, and the intermediates used in the preparation thereof.

In a further aspect, the compound of Formula I is (3R,5R)-5-fluoro-1-((1R,2R,4S)-4-(4-fluorophenyl)-2-(1H-1,2,4-triazol-1-yl)cyclopentyl)piperidin-3-amine. In embodiments, (3R,5R)-5-fluoro-1-((1R,2R,4S)-4-(4-fluorophenyl)-2-(1H-1,2,4-triazol-1-yl)cyclopentyl)piperidin-3-amine is provided in a crystalline form, for example a single crystalline polymorph Form A as further described herein.

These and other aspects of the present application are described in greater detail herein below.

BRIEF DESCRIPTION OF DRAWING

FIG. 1 shows an X-ray powder diffraction pattern of one crystalline form of (3R,5R)-5-fluoro-1-((1R,2R,4S)-4-(4-fluorophenyl)-2-(1H-1,2,4-triazol-1-yl)cyclopentyl)piperidin-3-amine, i.e. Compound 10 Form A.

The compounds of Formula I have a number of asymmetric carbons, for example, when b=1 there are two asymmetric carbons on the piperidine ring, at C3 and C5, and three on the cyclopentane ring, at C1, C2 and C4. The present description encompasses all of the possible enantiomers and diastereoisomers of the compounds of Formula I.

For the purpose of this specification, the term "5-membered aromatic heterocycle" means a 5-membered aromatic ring comprising 1 to 4 nitrogen atoms. Examples of suitable 5-membered aromatic heterocycles include pyrrolyl, imidazolyl, pyrazolyl, triazolyl and tetrazolyl.

For the avoidance of doubt, when the positions C2 to C5 on the piperidine ring are referred to in this specification, it is in reference to the positions on the piperidine ring as labeled below;

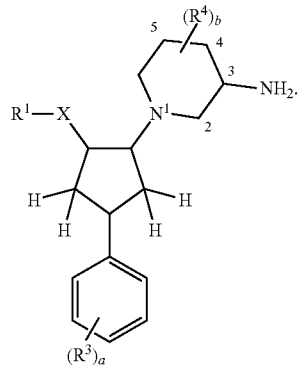

In embodiments the compound of Formula is a compound of Formula Ia wherein the asymmetric carbon at C3 of the piperidine group is in the (R)-configuration.

Formula Ia

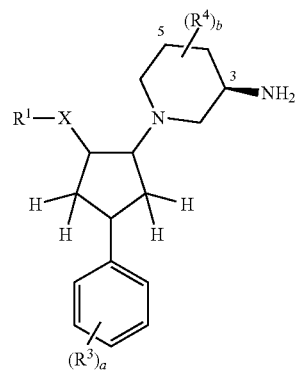

For example, the compound of Formula Ia may be a compound of Formula Iai wherein the asymmetric carbons at C3 and C5 of the piperidine group are in the (R)-configuration i.e. the compound of Formula Ia is (3R,5R)-5-fluoro-1-[4-(4-fluorophenyl)-2-(1H-1,2,4-triazol-1-yl)cyclopentyl]piperidin-3-amine as shown below.

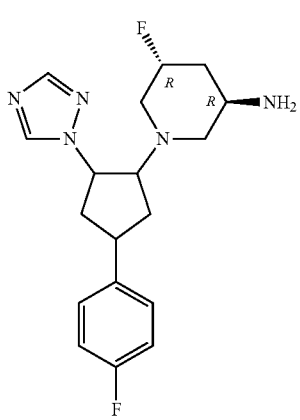

Formula Iai

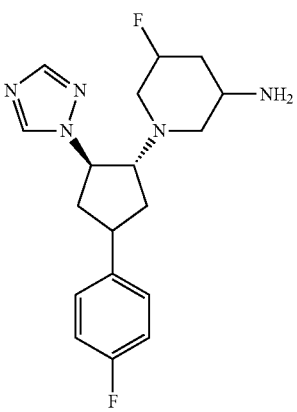

Embodiments of the compounds of Formula I and Ia, include compounds of Formula Ib wherein the group XR¹ and piperidine groups are trans to each other.

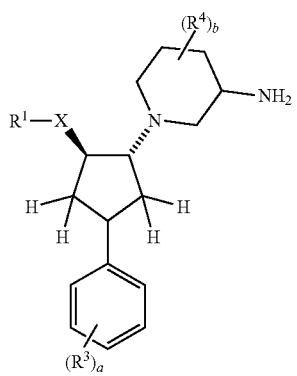

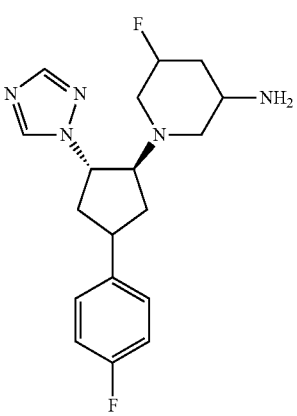

Diastereoisomers of Formula Ibi

Embodiments of the compounds of Formula I, Ia and Ib, include compounds of Formula Ic wherein the piperidine and phenyl groups are cis to each other.

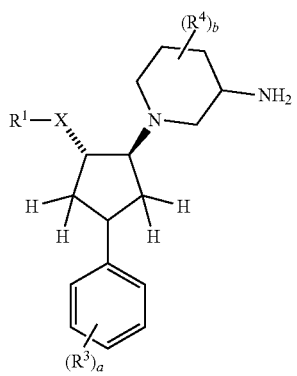

Diastereoisomers of Formula Ib

Thus, in the case wherein the stereochemistry of the groups on the piperidine ring are not specified the compound may be a compound of Formula Ibi, i.e. 5-fluoro-1-[(1R,2R)-4-(4-fluorophenyl)-2-(1H-1,2,4-triazol-1-yl)cyclopentyl]piperidin-3-amine or 5-fluoro-1-[(1S,2S)-4-(4-fluorophenyl)-2-(1H-1,2,4-triazol-1-yl)cyclopentyl]piperidin-3-amine as shown below.

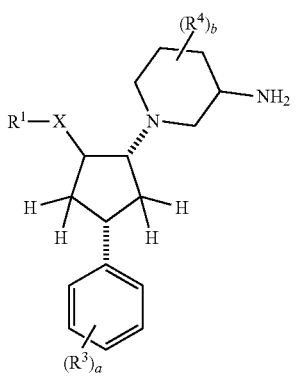

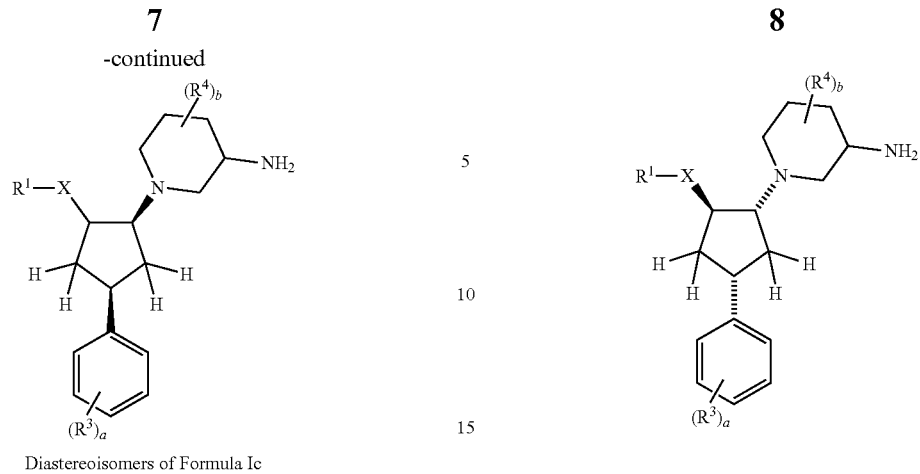

Diastereoisomers of Formula Ic

Thus, in the case where in the stereochemistry of the groups on the piperidine ring are not specified the compound of Formula Ic may be a compound of Formula Ici 5-fluoro-1-[(1R,4S)-4-(4-fluorophenyl)-2-(1H-1,2,4-triazol-1-yl)cyclopentyl]piperidin-3-amine or 5-fluoro-1-[(1S,4R)-4-(4-fluorophenyl)-2-(1H-1,2,4-triazol-1-yl)cyclopentyl]piperidin-3-amine as shown below.

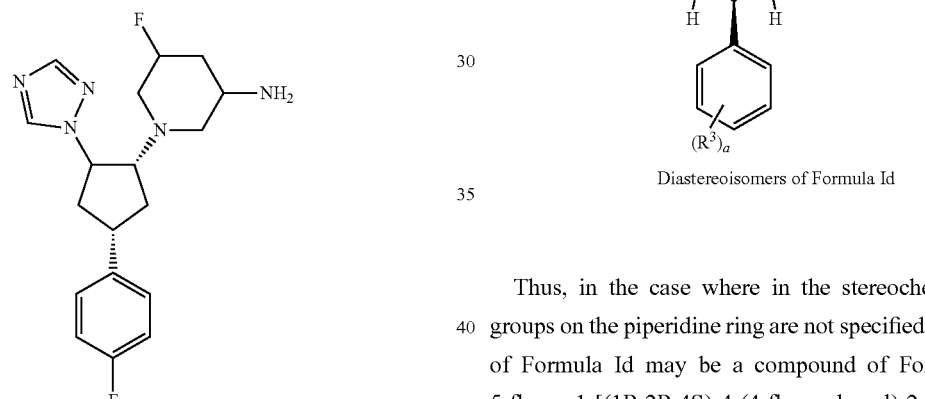

Diastereoisomers of Formula Ici

Embodiments of the compounds of Formula I, Ia, Ib, and Ic include compounds of Formula Id wherein the piperidine and phenyl groups are cis to each other, and the piperidine and $XR^1$ groups are trans to each other.

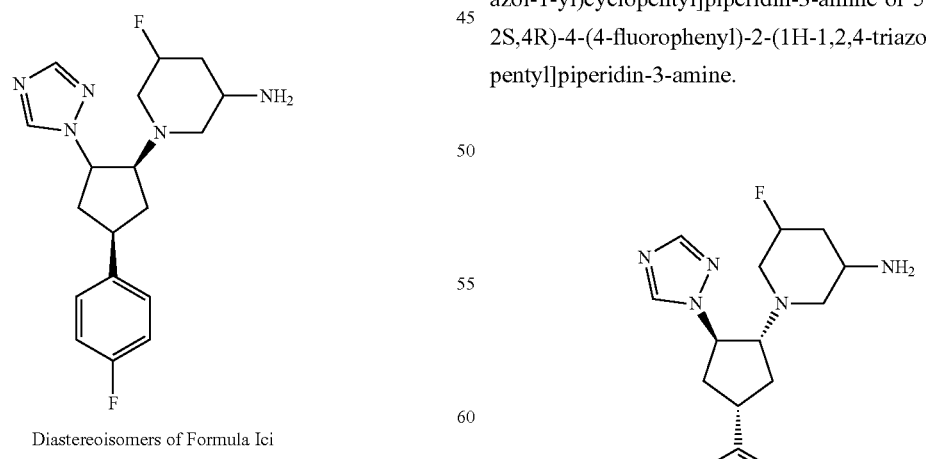

Diastereoisomers of Formula Id

Thus, in the case where in the stereochemistry of the groups on the piperidine ring are not specified the compound of Formula Id may be a compound of Formula Idi, i.e. 5-fluoro-1-[(1R,2R,4S)-4-(4-fluorophenyl)-2-(1H-1,2,4-triazol-1-yl)cyclopentyl]piperidin-3-amine or 5-fluoro-1-[(1S,2S,4R)-4-(4-fluorophenyl)-2-(1H-1,2,4-triazol-1-yl)cyclopentyl]piperidin-3-amine.

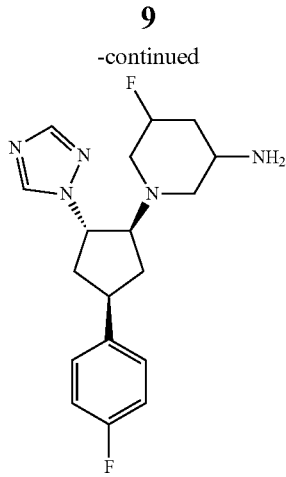

Diastereoisomers of Formula Idi

In embodiments of Formula Id wherein the piperidine group is a 5-fluoro-(3R,5R)-piperidine-3-amine group, the compound of Formula Id may be (3R,5R)-5-fluoro-1-[(1R,2R,4S)-4-(4-fluorophenyl)-2-(1H-1,2,4-triazol-1-yl)cyclopentyl]piperidin-3-amine or (3R,5R)-5-fluoro-1-[(1S,2S,4R)-4-(4-fluorophenyl)-2-(1H-1,2,4-triazol-1-yl)cyclopentyl]piperidin-3-amine, as shown below.

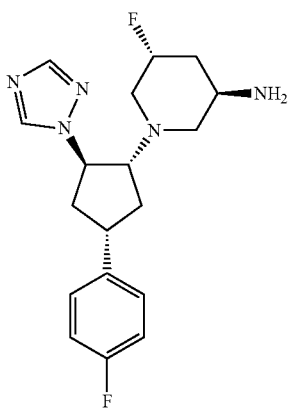

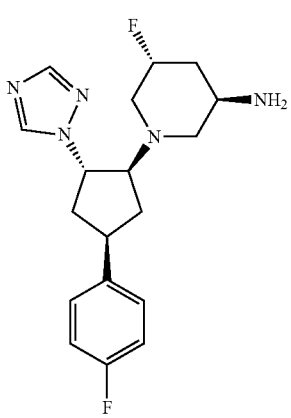

In one embodiment, the compound of Formula I is (3R,5R)-5-fluoro-1-[(1R,2R,4S)-4-(4-fluorophenyl)-2-(1H-1,2,4-triazol-1-yl)cyclopentyl]piperidin-3-amine.

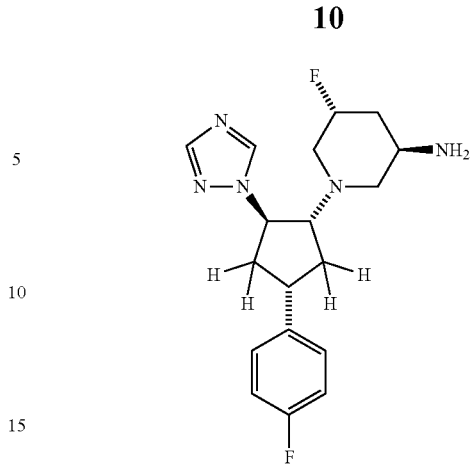

In embodiments, the compound of Formula I, Ia, Ib, Ic or Id is a compound of Formula Ie wherein the group X is O, and $R^1$ is a 6-membered aromatic or heteroaromatic ring selected from phenyl, pyridyl, pyrimidyl, pyrazinyl or pyridazyl that is optionally substituted with one or two substituents Y independently selected from F, Cl, Br, CN, OH, $OC_{1-3}$alkyl, $OCF_3$, $C(O)NH_2$, $CF_3$ or cyclopropyl.

In embodiments, the compound of Formula Ie is a compound of Formula If wherein at least one substituent on the 6-membered aromatic or heteroaromatic ring $R^1$ is selected from Me, Cl, F and CN.

In embodiments, the compound of Formula I, Ia, Ib, Ic or Id is a compound of Formula Ig wherein the group $XR^1$ is $NR^2$, and wherein N, $R^1$ and $R^2$ together form a 5-membered aromatic heterocycle that is optionally substituted with one or two substituents V independently selected from F, Cl, CN, or Me In embodiments, the compound of Formula Ig is a compound of Formula Ih wherein at least one substituent on the 5-membered aromatic heterocycle is selected from Me, Cl, F and CN.

In embodiments, the compound of Formula Ig is a compound of Formula Ii wherein the 5-membered aromatic heterocycle is unsubstituted.

In embodiments, the compound of Formula I, Ia, Ib, Ic, Id, Ie, If, Ig, Ih or Ii is a compound of Formula Ij wherein at least one substituent $R^3$ is para-to the bond to the cyclopentane ring.

In embodiments, the compound of Formula Ij is a compound of Formula Ik wherein the substituent $R^3$ is F and a=1.

In embodiments, the compound of Formula I, Ia, Ib, Ic, Id, Ie, If, Ig, Ih, Ii, Ij or Ik is a compound of Formula Il wherein at least one group $R^4$ is F.

In embodiments, the compound of Formula Il is a compound of Formula Im wherein b=1.

In embodiments, the compound of Formula I, Ia, Ib, Ic, Id, Ie, If, Ig, Ih, Ii, Ij, Ik, Il or Im is a compound of Formula In, wherein $R^4$ is independently selected from F or Cl attached to C4 or C5 of the piperidine ring.

In embodiments, the compound of Formula I, Ia, Ib, Ic, Id, Ie, If, Ig, Ih, Ii, Ij, Ik, Il or is a compound of Formula Io, wherein $R^4$ is F attached to C4 or C5 of the piperidine ring.

In embodiments, the compound of Formula I, Ia, Ib, Ic or Id is selected from:

1-[4-(4-fluorophenyl)-2-(triazol-2-yl)cyclopentyl]piperidin-3-amine;

1-[2-(3-amino-1-piperidyl)-4-(4-fluorophenyl)cyclopentyl]pyrazole-4-carbonitrile;

1-[2-(3-amino-1-piperidyl)-4-(4-fluorophenyl)cyclopentyl] pyrazole-3-carbonitrile;
1-[2-(3-amino-1-piperidyl)-4-(4-fluorophenyl)cyclopentyl] pyrrole-3-carbonitrile;
1-[2-(3-amino-1-piperidyl)-4-(4-fluorophenyl)cyclopentyl] triazole-4-carbonitrile;
1-[2-(3-amino-5-fluoro-1-piperidyl)-4-(4-fluorophenyl)cyclopentyl]pyrazole-4-carbonitrile;
1-[2-(3-amino-4,4-difluoro-1-piperidyl)-4-(4-fluorophenyl)cyclopentyl]pyrazole-4-carbonitrile;
1-[4-(4-fluorophenyl)-2-pyrazol-1-yl-cyclopentyl]piperidin-3-amine;
5-fluoro-1-[4-(4-fluorophenyl)-2-pyrazol-1-yl-cyclopentyl]piperidin-3-amine;
5-fluoro-1-[4-(4-fluorophenyl)-2-(1,2,4-triazol-1-yl)cyclopentyl]piperidin-3-amine;
5-fluoro-1-[4-(4-fluorophenyl)-2-(tetrazol-2-yl)cyclopentyl]piperidin-3-amine;
1-[4-(4-fluorophenyl)-2-(tetrazol-2-yl)cyclopentyl]piperidin-3-amine;
1-[2-(3-amino-1-piperidyl)-4-(4-fluorophenyl)cyclopentyl]-1,2,4-triazole-3-carbonitrile;
4-[2-(3-amino-1-piperidyl)-4-(4-fluoro-3-hydroxy-phenyl)cyclopentoxy]benzonitrile;
4-[2-(3-amino-1-piperidyl)-4-(4-fluoro-3-methoxy-phenyl)cyclopentoxy]benzonitrile;
4-[2-(3-amino-1-piperidyl)-4-(3-fluorophenyl)cyclopentoxy]-3-chloro-benzonitrile;
4-[2-(3-amino-4,4-difluoro-1-piperidyl)-4-(4-fluorophenyl)cyclopentoxy]benzonitrile;
4-[2-(5-amino-3,3-difluoro-1-piperidyl)-4-(4-fluorophenyl)cyclopentoxy]benzonitrile
4-[2-(3-amino-1-piperidyl)-4-(4-fluorophenyl)cyclopentoxy]-2-fluoro-benzonitrile;
2-[2-(3-amino-1-piperidyl)-4-phenyl-cyclopentoxy]benzonitrile;
4-[2-(3-amino-1-piperidyl)-4-phenyl-cyclopentoxy]-3-chloro-benzonitrile;
6-[2-(3-amino-5-fluoro-1-piperidyl)-4-(4-fluorophenyl)cyclopentoxy]-5-methyl-pyridazine-3-carbonitrile;
1-[2-(4-chloropyridazin-3-yl)oxy-4-(4-fluorophenyl)cyclopentyl]piperidin-3-amine;
6-[2-(3-amino-5-fluoro-1-piperidyl)-4-(4-fluorophenyl)cyclopentoxy]pyridazine-3-carbonitrile;
1-[4-(4-fluorophenyl)-2-(5-fluoropyridazin-3-yl)oxy-cyclopentyl]piperidin-3-amine;
6-(2-((R)-3-aminopiperidin-1-yl)-4-(4-fluorophenyl)cyclopentyloxy)nicotinonitrile;
6-[2-(3-amino-1-piperidyl)-4-(4-fluorophenyl)cyclopentoxy]pyridine-3-carbonitrile;
1-[4-(4-fluorophenyl)-2-pyridazin-3-yloxy-cyclopentyl]piperidin-3-amine;
5-fluoro-1-[4-(4-fluorophenyl)-2-pyrimidin-4-yloxy-cyclopentyl]piperidin-3-amine;
2-[2-(3-amino-1-piperidyl)-4-(4-fluorophenyl)cyclopentoxy]pyrimidine-5-carbonitrile;
5-[2-(3-amino-1-piperidyl)-4-(4-fluorophenyl)cyclopentoxy]pyrazine-2-carbonitrile; and
5-[2-(3-amino-1-piperidyl)-4-(4-fluorophenyl)cyclopentoxy]pyrimidine-2-carbonitrile;
or a pharmaceutically acceptable salt thereof.

In one embodiment, there is provided a pharmaceutical composition comprising a therapeutically effective amount of a compound of Formula I or a pharmaceutically acceptable salt thereof, and at least one pharmaceutically acceptable diluent, excipient or inert carrier. In one embodiment, the pharmaceutical composition comprises a compound of Formula I in the free base form.

In one embodiment, there is provided a compound of Formula I or a pharmaceutically acceptable salt thereof, for use in treatment or prophylaxis of diseases and conditions in which inhibition of TRPC6 and/or TRPC3 is beneficial. In one embodiment, the use of is for the treatment of kidney disease. In one embodiment, the kidney disease is focal segmental glomerulosclerosis (FSGS). In one embodiment, the kidney disease is focal segmental glomerulosclerosis (FSGS) with a TRPC6 gain of function mutation as described in Winn et al, Science. 2005, 308 (5729):1801-4.

In one embodiment, there is provided a compound of Formula I or a pharmaceutically acceptable salt thereof for use in the preparation of a medicine for the treatment of diseases or conditions in which inhibition of TRPC6 and/or TRPC3 is beneficial. In one embodiment, said disease or condition is kidney disease. In one embodiment, the kidney disease is focal segmental glomerulosclerosis (FSGS), for example FSGS with a TRPC6 gain of function mutation.

In one embodiment, there is provided a method of treating a disease or condition in which inhibition of TRPC6 and/or TRPC3 is beneficial, comprising administering to a patient in need thereof an effective amount of a compound of Formula I or a pharmaceutically acceptable salt thereof. In one embodiment, said disease or condition is kidney disease. In one embodiment, the kidney disease is focal segmental glomerulosclerosis (FSGS), for example FSGS with a gain of function mutation.

In one embodiment, is provided a compound of Formula I or a pharmaceutically acceptable salt thereof, for use as medicament.

In one embodiment, there is provided a process for the preparation of compounds of Formula I, and the intermediates used in the preparation thereof.

In one embodiment the process for the preparation of a compound of Formula I involves the step

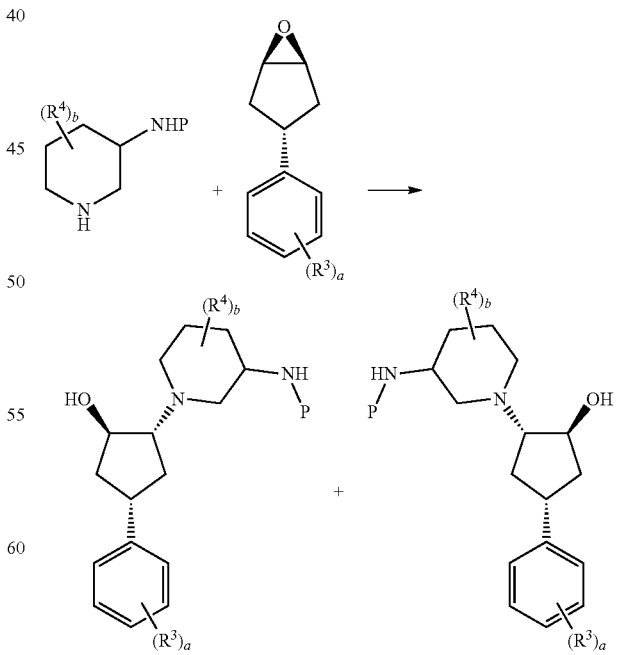

wherein P is a suitable nitrogen protecting group. P may be a carbamate protecting group, for example a tert-butoxycarbonyl or Boc group. The aminopiperidine group may be provided in single enantiomeric or diastereomeric form. The aminopiperidine group may be provided with an e.e. of >95%, a d.e. of >95% or an e.e. of >95% and a d.e. of >95%.

It has been found that (3R,5R)-5-fluoro-1-((1R,2R,4S)-4-(4-fluorophenyl)-2-(1H-1,2,4-triazol-1-yl)cyclopentyl)piperidin-3-amine, also referred to herein as Compound 10, may exist as a crystalline form, "Compound 10 Form A", or simply "Form A". One crystalline form of (3R,5R)-5-fluoro-1-((1R,2R,4S)-4-(4-fluorophenyl)-2-(1H-1,2,4-triazol-1-yl) cyclopentyl)piperidin-3-amine, i.e. Compound 10 Form A, provides an X-ray powder diffraction pattern substantially as shown in FIG. 1.

One aspect provides a crystalline form of (3R,5R)-5-fluoro-1-((1R,2R,4S)-4-(4-fluorophenyl)-2-(1H-1,2,4-triazol-1-yl)cyclopentyl)piperidin-3-amine.

Another aspect provides (3R,5R)-5-fluoro-1-((1R,2R, 4S)-4-(4-fluorophenyl)-2-(1H-1,2,4-triazol-1-yl)cyclopentyl)piperidin-3-amine, Form A, which exhibits the characteristic X-ray powder diffraction peaks (expressed in degrees 2θ) as shown in Table 1 below, using CuKα radiation.

(3R,5R)-5-Fluoro-1-((1R,2R,4S)-4-(4-fluorophenyl)-2-(1H-1,2,4-triazol-1-yl)cyclopentyl)piperidin-3-amine, Form A is characterised in providing at least one of the following 2θ values measured using CuKα radiation: 17.1° and 20.2°. (3R,5R)-5-Fluoro-1-((1R,2R,4S)-4-(4-fluorophenyl)-2-(1H-1,2,4-triazol-1-yl)cyclopentyl)piperidin-3-amine, Form A is characterised in providing an X-ray powder diffraction pattern, substantially as shown in Figure A. The thirteen most prominent peaks are shown in Table 1:

TABLE 1

The thirteen most prominent X-ray powder diffraction peaks for Compound 10, Form A

| Angle 2-Theta (2θ) | Intensity % | Relative Intensity |
| --- | --- | --- |
| 12.3 | 13.7% | s |
| 13.4 | 12.8% | s |
| 13.6 | 28.0% | vs |
| 17.1 | 77.2% | vs |
| 18.9 | 16.7% | s |
| 20.2 | 100% | vs |
| 20.9 | 12.8% | s |
| 21.3 | 8.2% | m |
| 21.8 | 20.1% | s |
| 22.2 | 58.3% | vs |
| 24.5 | 20.0% | s |
| 25.3 | 13.1% | s |
| 27.0 | 18.5% | s | w = weak m = medium s = strong vs = very strong (see also Table 3 below)

According to an embodiment of the present specification there is provided a crystalline form of (3R,5R)-5-fluoro-1-((1R,2R,4S)-4-(4-fluorophenyl)-2-(1H-1,2,4-triazol-1-yl) cyclopentyl)piperidin-3-amine, Form A, which has an X-ray powder diffraction pattern with at least one specific peak at about 2-theta=17.1°.

According to an embodiment of the present specification there is provided a crystalline, form of (3R,5R)-5-fluoro-1-((1R,2R,4S)-4-(4-fluorophenyl)-2-(1H-1,2,4-triazol-1-yl) cyclopentyl)piperidin-3-amine, Form A, which has an X-ray powder diffraction pattern with at least one specific peak at about 2-theta=20.2°.

According to an embodiment of the present specification there is provided a crystalline form of (3R,5R)-5-fluoro-1-((1R,2R,4S)-4-(4-fluorophenyl)-2-(1H-1,2,4-triazol-1-yl) cyclopentyl)piperidin-3-amine, Form A, which has an X-ray powder diffraction pattern with at least two specific peaks at about 2-theta=17.1° and 20.2°.

According to an embodiment of the present specification there is provided a crystalline form of (3R,5R)-5-fluoro-1-((1R,2R,4S)-4-(4-fluorophenyl)-2-(1H-1,2,4-triazol-1-yl) cyclopentyl)piperidin-3-amine, Form A, which has an X-ray powder diffraction pattern with specific peaks at about 2-theta 12.3, 13.4, 13.6, 17.1, 18.9, 20.2, 20.9, 21.3, 21.8, 22.2, 24.5, 25.3 and 27.0°.

According to an embodiment of the present specification there is provided crystalline form of (3R,5R)-5-fluoro-1-((1R,2R,4S)-4-(4-fluorophenyl)-2-(1H-1,2,4-triazol-1-yl) cyclopentyl)piperidin-3-amine, Form A, which has an X-ray powder diffraction pattern substantially the same as the X-ray powder diffraction pattern shown in FIG. 1.

According to an embodiment of the present specification there is provided a crystalline form of (3R,5R)-5-fluoro-1-((1R,2R,4S)-4-(4-fluorophenyl)-2-(1H-1,2,4-triazol-1-yl) cyclopentyl)piperidin-3-amine, Form A, wherein said form has an X-ray powder diffraction pattern with at least one specific peak at 2-theta=17.1° plus or minus 0.5° 2-theta.

According to an embodiment of the present specification there is provided a crystalline form, Form A, wherein said form has an X-ray powder diffraction pattern with at least one specific peak at 2-theta=20.2° plus or minus 0.5° 2-theta.

According to an embodiment of the present specification there is provided a crystalline form, Form A, wherein said form has an X-ray powder diffraction pattern with at least two specific peaks at 2-theta=17.1° and 20.2° wherein said values may be plus or minus 0.5° 2-Theta.

According to an embodiment of the present specification there is provided a crystalline form, Form A, wherein said form has an X-ray powder diffraction pattern with specific peaks at 2-theta=12.3, 13.4, 13.6, 17.1, 18.9, 20.2, 20.9, 21.3, 21.8, 22.2, 24.5, 25.3 and 27.0° wherein said values may be plus or minus 0.5° 2-theta.

When it is stated that embodiments of the present specification relate to a crystalline form of (3R,5R)-5-fluoro-1-((1R,2R,4S)-4-(4-fluorophenyl)-2-(1H-1,2,4-triazol-1-yl) cyclopentyl)piperidin-3-amine the degree of crystallinity is conveniently greater than about 60%, more conveniently greater than about 80%, preferably greater than about 90% and more preferably greater than about 95%. Most preferably the degree of crystallinity is greater than about 98%.

The crystalline form of (3R,5R)-5-fluoro-1-((1R,2R,4S)-4-(4-fluorophenyl)-2-(1H-1,2,4-triazol-1-yl)cyclopentyl)piperidin-3-amine, Form A provides X-ray powder diffraction patterns substantially the same as the X-ray powder diffraction patterns shown in FIG. 1 and has substantially the thirteen most prominent peaks (angle 2-theta values) shown in Table 1. It will be understood that the 2-theta values of the X-ray powder diffraction pattern may vary slightly from one machine to another or from one sample to another, and so the values quoted are not to be construed as absolute.

In this specification, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compounds of Formula I have more than one chiral center, and it is to be understood that the application encompasses all individual stereoisomers, enantiomers and diastereoisomers and mixtures thereof. Thus, it is to be understood that, insofar as the compounds of Formula I can exist in optically active or racemic forms by virtue of one or more asymmetric carbon atoms, the application includes in its definition any such optically active or racemic form which possesses the above-mentioned activity. The present application encompasses all such stereoisomers having activity as herein defined.

The synthesis of optically active forms may be carried out by standard techniques of organic chemistry well known in the art, for example by synthesis from optically active starting materials or by resolution of a racemic form, Racemates may be separated into individual enantiomers using known procedures (see, for example, Advanced Organic Chemistry: 3rd Edition: author J. March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using the standard laboratory techniques referred to hereinafter.

Thus, throughout the specification, where reference is made to the compound of Formula I it is to be understood that the term compound includes diastereoisomers, mixtures of diastereoisomers, and enantiomers that are TRPC6 and TRCP3 inhibitors.

Stereoisomers may be separated using conventional techniques, e.g. chromatography or fractional crystallisation. The enantiomers may be isolated by separation of a racemate for example by fractional crystallisation, resolution or HPLC or SFC, The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of Formula I may contain less than 30%, particularly less than 2.0%, and more particularly less than 10% by weight of other stereoisomers of the same compound. In another aspect, a mixture containing a particular stereoisomer of the compound of Formula I may contain less than 6%, particularly less than 3%, and more particularly less than 2% by weight of other stereoisomers of the compound. In another aspect, a mixture containing a particular stereoisomer of the compound of Formula I may contain less than 1%, particularly less than 0.5%, and more particularly less than 0.3%, and still more particularly less 0.1% by weight of other stereoisomers of the compound.

It is also to be understood that certain compounds of Formula I, and pharmaceuticals salts thereof, can exist in solvated as well as unsolvated forms such as, for example, hydrated and anhydrous forms. It is to be understood that the compounds herein encompass all such solvated forms. For the sake of clarity, this includes both solvated (e.g., hydrated) forms of the free form of the compound, as well as solvated (e.g., hydrated) forms of the salt of the compound.

Formula I as described herein is intended to encompass all isotopes of its constituent atoms. For example, H (or hydrogen) includes any isotopic form of hydrogen including $^1H$, $^2H$ (D), and $^3H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $^{13}N$, $^{14}N$ and $^{15}N$; F includes any isotopic form of fluorine including $^{19}F$ and $^{18}F$; and the like. In one aspect, the compounds of Formula I include isotopes of the atoms covered therein in amounts corresponding to their naturally occurring abundance. However, in certain instances, it may be desirable to enrich one or more atom in a particular isotope which would normally be present in a lower abundance. For example, $^1H$ would normally be present in greater than 99.98% abundance; however, in one aspect, a compound of any formula presented herein may be enriched in $^2H$ or $^3H$ at one or more positions where H is present. In another aspect, when a compound of any formula presented herein is enriched in a radioactive isotope, for example $^3$H and $^{14}$C, the compound may be useful in drug and/or substrate tissue distribution assays. It is to be understood that the present application encompasses all such isotopic forms.

There is provided a method of treatment of a condition where inhibition of TRPC6 and/or TRPC3 is required, which method comprises administration of a therapeutically effective amount of a compound of Formula I, or a pharmaceutically acceptable salt thereof, to a person suffering from, or susceptible to, such a condition.

The compounds of Formula I, or pharmaceutically acceptable salts thereof, will normally be administered via the oral route in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated, the compositions may be administered at varying doses.

The pharmaceutical formulations of the compound of Formula I described above may be prepared for oral administration, particularly in the form of tablets or capsules, and especially involving technologies aimed at furnishing colon-targeted drug release (Patel, M. M. Expert Opin. Drug Deliv. 2011, 8 (10), 1247-1258).

The pharmaceutical formulations of the compound of Formula described above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Pharmaceutical formulations suitable for oral administration may comprise one or more physiologically compatible carriers and/or excipients and may be in solid or liquid form. Tablets and capsules may be prepared with binding agents, fillers, lubricants and/or surfactants, such as sodium lauryl sulfate. Liquid compositions may contain conventional additives such as suspending agents, emulsifying agents and/or preservatives. Liquid compositions may be encapsulated in, for example, gelatin to provide a unit dosage form. Solid oral dosage forms include tablets, two-piece hard shell capsules and soft elastic gelatin (SEG) capsules. Such two-piece hard shell capsules may be made for example by filling a compound of Formula (I) into a gelatin or hydroxypropyl methylcellulose (HPMC) shell.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitable daily doses of the compounds of Formula I, or a pharmaceutically acceptable salt thereof, in therapeutic treatment of humans are about 0.0001-100 mg/kg body weight.

Oral formulations are preferred, particularly tablets or capsules which may be formulated by methods known to those skilled in the art to provide doses of the active compound in the range of 0.1 mg to 1000 mg.

According to a further aspect there is thus provided a pharmaceutical composition comprising a compound of Formula I, or a pharmaceutically acceptable salt thereof, in admixture with at least one pharmaceutically acceptable adjuvants, diluents and/or carriers.

Biological Assays

The following test procedures may be employed to determine the inhibitory properties of the compounds described herein.

TRPC3 and TRPC6 channel opening causes an influx of predominantly calcium and sodium cations that result in a change in the electrical potential across the cell membrane. This change in membrane potential can be monitored using membrane potential dyes in the following FLIPR™ (Fluorescent Imaging Plate Reader) assays.

Inhibition of TRPC6 FLIPR™ Assay

TRPC6-HEK293 was purchased from PerkinElmer (PerkinElmer, Product No.: AX-012-C), HEK293 cells were transfected using the pcDNA3.1(+)expression vector containing the coding sequence of the human TRPC6 ion channel. The coding sequence used is identical to coding sequence of GenBank NM_004621 with the exception of 2 synonym variations (t1683c and c2529t). The cells were grown in DMEM+10% fetal bovine serum (FBS) 0.5 mg/ml. Geneticin (ion channel expression selection) as culture medium.

TRPC6 cells were plated at 10K cells/well into 384-well polystyrene plates and then grown for 24 hs at 37° C. plus 5% $CO_2$. After this time the media was aspirated using a Tecan plate washer and then replaced with 40 µL of dye loading buffer (130 mM NaCl, 5 mM KCl, 0.15 mM $CaCl_2$, 1 mM $MgCl_2$, 20 mM HEPES ((4-(2-hydroxyethyl)-1-piperazineethanesulfonic acid)), 5 mM $NaHCO_3$). For TRPC6, a final concentration of 0.5× is used. Cells with membrane potential dye were then incubated for 30 mins at room temperature prior to beginning the experiments.

To test the effects of compounds on TRPC6 activity, compounds were first diluted in 100% DMSO to 3× the final concentration to be used in the experiments. Typical dose-response experiments ranged from 10 µM (top concentration) to 0.5 nM (lowest concentration). Ten microliters of 0.5× compound in 0.5% DMSO were added to 40 µL of cells incubated with membrane potential dye. Compound addition was performed on a FLIPRTetra or a FLIPR 384 (MDS Analytical Technologies, Molecular Devices, Sunnyvale, Calif., 94089, USA). After a 400 second incubation with compound, 12.5 of OAG (1-oleoyl-2-acetyl-sn-glycerol (OAG), Sigma, Gillingham, Dorset, SP8 4XT Cat #O6754-10 MG) was added at 5× the $EC_{80}$ (typical $EC_{80}$ for TRPC6=3 µM final). The OAG challenge is designed to measure the inhibitory activity of compounds on receptor-operated TRPC6 activation.

All data was normalized to low controls (buffer alone) or high controls (OAG $EC_{100}$). Data was analyzed using an $XC_{50}$ curve fitting module and reported as $pIC_{50}$ or $IC_{50}$ values. The values are averaged to determine a mean value, for a minimum of 2 experiments.

Inhibition of TRPC3—FLIPR™ Assay

AD293 cells were transfected using the PLVX-puro lentivirus vector containing the coding sequence of the human TRPC3 ion channel. Puromycin-resistant cells were selected by treating with 2 µm/mL puromycin for two weeks. Monoclonal cells were obtained by limiting dilution and compared for their response to OAG in a membrane potential assay. The cells were grown in DMEM+10% fetal bovine serum (FBS)+1 µg/mL puromycin as culture medium.

TRPC3 cells were plated at 9K/well into 384-well polystyrene plates. Cells were grown for 24 h at 37° C. plus 5% $CO_2$ after which media was aspirated using a Tecan plate washer and replaced with 40 µL of dye loading buffer (130 mM NaCl, 5 mM KCl, 0.15 mM CaCl$_2$, 1 mM MgCl$_2$, 20 mM HEPES ((4-(2-hydroxyethyl)-1-piperazineethanesulfonic acid)), 5 mM NaHCO$_3$). For TRPC3 a final concentration of 0.5× membrane potential dye (Molecular Devices Membrane Blue, FLIPR Membrane Potential Assay Kit (bulk), Product #R8034(BLUE), Molecular Devices, Sunnyvale, Calif., 94089, USA) was used. Cells with membrane potential dye were then incubated for 30 mins at room temperature prior to beginning the experiments.

To test the effects of compounds on TRPC3 activity, compounds were first diluted in 100% DMSO to 3× the final concentration to be used in the experiments. Typical dose-response experiments ranged from 10 µM (top concentration) to 0.5 nM (lowest concentration). Ten microliters of 5× compound in 0.5% DMSO were added to 40 µL of cells incubated with membrane potential dye. Compound addition was performed on a FLIPRTetra or a FLIPR 384 (MDS Analytical Technologies). After a 400 second incubation with compound, 12.5 µL of OAG was added at 5× the EC$_{80}$ (typical EC$_{80}$ for TRPC3=2 µM final). The OAG challenge is designed to measure the inhibitory activity of compounds on receptor-operated TRPC3 activation.

All data was normalized to low controls (buffer alone) or high controls (OAG EC$_{100}$). Data was analyzed using an XC$_{50}$ curve fitting module and reported as pIC$_{50}$ or IC$_{50}$ values. The values are averaged to determine a mean value, for a minimum of 2 experiments.

Electrophysiology Assays of TRPC6 and TRPC3 Activation

TRPC6 and TRPC3 channel activation results in ionic current which can be measured using the whole-cell patch-clamp technique (see Estacion et al, *J Physiol.* 2006 Apr. 15; 572(Pt 2): 359-377 and Washburn et al, *Bioorg Med Chem Lett.* 2013 Sep. 1; 23(17):4979-84), 10 µM OAG (OAG is a direct activator of TRPC6 and TRPC3 channel) was used to activate human TRPC6 or TRPC3 current in TRPC6 transduced HEK293 cells or TRPC3 transduced AD293 cells, respectively. The TRPC6 or TRPC3 transduced cells were incubated at 37° C. and 5% CO$_2$. The transduced cells were then detached from the flask using trypsin solution (0.25% trypsin+0.1% EDTA (ethylenediamine tetraacetic acid)) and then stored in culture medium for patch-clamp experiments within 5 h. Cells were placed in a small chamber and continuously perfused with an external solution (~3 mL/min) using a RSC-200 perfusion system (Science Instruments, BioLogic). All current recordings are conducted at room temperature (~22° C.). Electrodes were made from glass capillary tubes and to give a resistance of 2-4 MΩ when filled with the respective internal solutions.

For TRPC6 current recording, the intracellular solution contained (in mM): 120 CsOH, 120 Aspartate, 20 CsCl, 2 MgCl$_2$, 0.4 CaCl$_2$, 10 HEPES, 2 Na$_2$ATP, 0.1 Na$_3$GTP, 10 Glucose, 1 EGTA (pH 7.2-7.25, adjusted with CsOH). The extracellular solution contained (in mM): 145 NaCl, 5 KCl, 1 CaCl$_2$, 1 MgCl$_2$, 10 HEPES, 10 Glucose (pH 7.4 adjusted with NaOH).

For TRPC3 current recording, the intracellular solution contained (in mM): 130 CsCl, 5 HEPES, 5 EGTA, 5 Na$_2$ATP, Na$_3$GTP, 5.5 MgCl$_2$ (pH 7.2-7.25, adjusted with CsOH). The extracellular solution contained (in mM): 140 NaCl, 4 KCl, 1 MgCl$_2$, 10 HEPES, 0.2 CaCl$_2$, 10 Glucose, 2 Na$_4$EDTA (pH7.4 adjusted with NaOH).

A seal between cell membrane and electrode was made. After whole-cell configuration was established, cell membrane capacitance is cancelled electronically and the series resistance was compensated by about 70%. TRPC6 or TRPC3 current are induced by a 300 ms voltage ramp protocol (from +100 mV to −100 mV) every 5 seconds at a holding potential of −60 mV. Once the control current was stabilized, the recording chamber was perfused with external solution containing a test compound. At each drug concentration, sufficient time was allowed for the drug effect to reach steady-state.

The TRPC6 or TRPC3 current was measured as the average current at +100 mV. The time course of current was plotted for the whole experiment. Percent inhibition (% I) of TRPC6 or TRPC3 was calculated from the formula % I=100×(1−I$_D$/I$_c$), where I$_o$ is the current amplitude measured at the end of a particular drug concentration and Ic is the control current amplitude measured before drug application. Zero current (background) level is set at the very beginning before OAG activated TRPC6 or TRPC3 current. Multi-Clamp 700B amplifier with Digidata 1440 interface and pCLAMP software (AXON Instruments, Molecular Devices, Sunnyvale, Calif., 94089, USA) are used for data acquisition and analysis. The average percent inhibition at each drug concentration is calculated first. Then, the average data is fitted to a logistic function using Prism 6 software to calculate the IC$_{50}$ values.

TABLE 2

Inhibition of TRPC6 and hTRPC3 as evaluated by FLIPR ™ Assay

| Example | Name* | TRPC6 IC$_{50}$ (µM) | TRPC3 IC$_{50}$ (µM) |
|---|---|---|---|
| 1 | 1-[4-(4-fluorophenyl)-2-(triazol-2-yl)cyclopentyl]piperidin-3-amine | 0.00337 | 0.0177 |
| 2 | 1-[2-(3-amino-1-piperidyl)-4-(4-fluorophenyl)cyclopentyl]pyrazole-4-carbonitrile | 0.00797 | 0.00831 |
| 3 | 1-[2-(3-amino-1-piperidyl)-4-(4-fluorophenyl)cyclopentyl]pyrazole-3-carbonitrile | <0.0199 | 0.0464 |
| 4 | 1-[2-(3-amino-1-piperidyl)-4-(4-fluorophenyl)cyclopentyl]pyrrole-3-carbonitrile | 0.00531 | 0.00539 |
| 5 | 1-[2-(3-amino-1-piperidyl)-4-(4-fluorophenyl)cyclopentyl]triazole-4-carbonitrile | 0.00378 | 0.00428 |
| 6 | 1-[2-(3-amino-5-fluoro-1-piperidyl)-4-(4-fluorophenyl)cyclopentyl]pyrazole-4-carbonitrile | 0.00406 | 0.00622 |
| 7 | 1-[2-(3-amino-4,4-difluoro-1-piperidyl)-4-(4-fluorophenyl)cyclopentyl]pyrazole-4-carbonitrile | 0.0162 | 0.0175 |
| 8 | 1-[4-(4-fluorophenyl)-2-pyrazol-1-yl-cyclopentyl]piperidin-3-amine | 0.0028 | 0.00797 |

TABLE 2-continued

Inhibition of TRPC6 and hTRPC3 as evaluated by FLIPR ™ Assay

| Example | Name* | TRPC6 IC$_{50}$ (μM) | TRPC3 IC$_{50}$ (μM) |
|---|---|---|---|
| 9 | 5-fluoro-1-[4-(4-fluorophenyl)-2-pyrazol-1-yl-cyclopentyl]piperidin-3-amine | 0.0034 | 0.00664 |
| 10 | 5-fluoro-1-[4-(4-fluorophenyl)-2-(1,2,4-triazol-1-yl)cyclopentyl]piperidin-3-amine | 0.0298 | 0.0160 |
| 11 | 5-fluoro-1-[4-(4-fluorophenyl)-2-(tetrazol-2-yl)cyclopentyl]piperidin-3-amine | 0.0106 | 0.00403 |
| 12 | 1-[4-(4-fluorophenyl)-2-(tetrazol-2-yl)cyclopentyl]piperidin-3-amine | 0.0267 | 0.00755 |
| 13 | 1-[2-(3-amino-1-piperidyl)-4-(4-fluorophenyl)cyclopentyl]-1,2,4-triazole-3-carbonitrile | 0.00710 | 0.0143 |
| 14 | 4-[2-(3-amino-1-piperidyl)-4-(4-fluoro-3-hydroxy-phenyl)cyclopentoxy]benzonitrile | 0.0174 | 0.0588 |
| 15 | 4-[2-(3-amino-1-piperidyl)-4-(4-fluoro-3-methoxy-phenyl)cyclopentoxy]benzonitrile | 0.00951 | 0.0225 |
| 16 | 4-[2-(3-amino-1-piperidyl)-4-(3-fluorophenyl)cyclopentoxy]-3-chloro-benzonitrile | 0.0193 | 0.0695 |
| 17 | 4-[2-(3-amino-4,4-difluoro-1-piperidyl)-4-(4-fluorophenyl)cyclopentoxy]benzonitrile | 0.0207 | 0.0461 |
| 18 | 4-[2-(5-amino-3,3-difluoro-1-piperidyl)-4-(4-fluorophenyl)cyclopentoxy]benzonitrile | 0.0311 | 0.0425 |
| 19 | 4-[2-(3-amino-1-piperidyl)-4-(4-fluorophenyl)cyclopentoxy]-2-fluoro-benzonitrile | 0.0251 | 0.0645 |
| 20 | 2-[2-(3-amino-1-piperidyl)-4-phenyl-cyclopentoxy]benzonitrile | 0.0141 | 0.0388 |
| 21 | 4-[2-(3-amino-1-piperidyl)-4-phenyl-cyclopentoxy]-3-chloro-benzonitrile | 0.0174 | 0.0723 |
| 22 | 6-[2-(3-amino-5-fluoro-1-piperidyl)-4-(4-fluorophenyl)cyclopentoxy]-5-methyl-pyridazine-3-carbonitrile | 0.0288 | 0.118 |
| 23 | 1-[2-(4-chloropyridazin-3-yl)oxy-4-(4-fluorophenyl)cyclopentyl]piperidin-3-amine | 0.00656 | 0.0113 |
| 24 | 6-[2-(3-amino-5-fluoro-1-piperidyl)-4-(4-fluorophenyl)cyclopentoxy]pyridazine-3-carbonitrile | >0.0118 | 0.00720 |
| 25 | 1-[4-(4-fluorophenyl)-2-(5-fluoropyridazin-3-yl)oxy-cyclopentyl]piperidin-3-amine | 0.00993 | 0.209 |
| 26 | 6-[2-(3-amino-1-piperidyl)-4-(4-fluorophenyl)cyclopentoxy]pyridine-3-carbonitrile | 0.00951 | 0.0255 |
| 27 | 6-[2-(3-amino-1-piperidyl)-4-(4-fluorophenyl)cyclopentoxy]pyridine-3-carbonitrile | 0.0220 | 0.0507 |
| 28 | 1-[4-(4-fluorophenyl)-2-pyridazin-3-yloxy-cyclopentyl]piperidin-3-amine | 0.0178 | 0.0322 |
| 29 | 5-fluoro-1-[4-(4-fluorophenyl)-2-pyrimidin-4-yloxy-cyclopentyl]piperidin-3-amine | 0.00344 | 0.00368 |
| 30 | 2-[2-(3-amino-1-piperidyl)-4-(4-fluorophenyl)cyclopentoxy]pyrimidine-5-carbonitrile | 0.0115 | 0.0240 |
| 31 | 5-[2-(3-amino-1-piperidyl)-4-(4-fluorophenyl)cyclopentoxy]pyrazine-2-carbonitrile | 0.0137 | 0.0255 |
| 32 | 5-[2-(3-amino-1-piperidyl)-4-(4-fluorophenyl)cyclopentoxy]pyrimidine-2-carbonitrile | 0.0106 | 0.0392 |

*Data are presented for the most potent isolated isomer of each compound.

As can be seen from the table above the compound of the present disclosure is a highly active inhibitor of both TRPC6 and TRPC3, with inhibitory activity in the assays used in the sub-30 nM range. This ability to inhibit both TRPC6 and TRPC3 may have therapeutic importance as the degree of selectivity may provide enhanced therapeutic efficacy relative to a selective inhibitor of either of these group 3 canonical Transient receptor potential channels. As noted above, TRPC3 and TRPC6 have high sequence homology and belong to the group 3 canonical Transient receptor potential channel grouping. The compound of the present disclosure thus has promise as therapeutic agent for the treatment or prophylaxis of diseases and conditions in which inhibition of TRPC6 and/or TRPC3 is beneficial, for example kidney disease and, in particular, focal segmental glomerulosclerosis (FSGS).

Process for Preparation of Compounds

Compounds of the specification can be prepared as described below. For example, Compound 10 can be prepared from 1-(cyclopent-3-enyl)-4-fluorobenzene starting material, itself available from olefin metathesis of 1-fluoro-4-(hepta-1,6-dien-4-yl)benzene. Oxidation of the cyclopentane, with any suitable oxidant such as m-CPBA or hydrogen peroxide in formic acid, provides an epoxide intermediate that can undergo nucleophilic ring opening with a piperidine nucleophile to afford a cyclopentanol derivative. The cyclopentanol derivative can then be transformed by Mitsunobu reaction to give a 1H-1,2,4-triazol-1-yl derivative. The final products are then obtained by Boc deprotection under acidic conditions. Full details of one synthesis of the final compounds are provided below. The various possible isomeric products obtained in each synthetic step can be separated by chromatography, for example preparative HPLC, such as preparative chiral HPLC or SFC. Suitable columns for use in these standard techniques and the corresponding eluent systems are provided below.

EXAMPLES

The compounds of the application will now be further explained by reference to the following non-limiting examples.

1H NMR measurements were performed on Bruker Avance spectrometers, operating at $^1$H frequencies of 300 and 400 MHz, respectively. The experiments were typically recorded at 25° C. Chemical shifts are given in ppm with the solvent as internal standard. HPLC was generally performed on Shimadzu UHPLC coupled with DAD detector, ELSD detector and 2020EV MS, or Shimadzu UFLC coupled with DAD detector, ELSD detector and 2020EV MS. Flash chromatography was performed using straight phase flash chromatography on a SP1™ Purification system from Biotage™ using normal phase silica FLASH+™ (40M, 25M or 12 M) or SNAP™ KP-Sil Cartridges (340, 100, 50 or 10), with C18-flash columns or standard flash chromatography. In general, all solvents used were commercially available and of analytical grade. Anhydrous solvents were routinely used for reactions. Phase Separators used in the examples are ISOLUTE® Phase Separator columns. The intermediates and examples named below were named using ACD/Name 12.01 from Advanced Chemistry Development, Inc. (ACD/Labs). The starting materials were obtained from commercial sources or made via literature routes. For example, tert-butyl ((3R,5R)-5-fluoropiperidin-3-yl)carbamate was purchased from PharmaBlock Inc, 10 Xuefu Road, Nanjing Hi-Tech Zone, China.

The following abbreviations are used: AcOH=acetic acid; aq=aqueous; Boc$_2$O=di-tert-butyl decarbonate; Boc=t-butyloxycarbonyl; br=broad; CDCl$_3$=deuterated chloroform; CD$_3$OD=deuterated methanol; CH$_3$NO$_2$=nitromethane; d=doublet; δ=chemical shift in NMR relative to tetramethyl silane; DCE=1,2-dichloroethane; DCM=dichloromethane; DEA=diethylamine; DEAD=diethyl azodicarboxylate; DIPEA=N,N-diisopropylethylamine; DMAP=2,6-dimethylaminopyridine; DMF=N,N-dimethylformamide; DMSO=dimethylsulfoxide; DMSO-d$_6$=deuterated dimethylsulfoxide; DPPA=diphenyl phosphorazidate; dppf=1,1'-bis(diphenylphosphino)ferrocene; DIAD=Di-isopropyl (E)-diazene-1,2-dicarboxylate; DSC=differential scanning calorimetry; DTAD=Di-tert-butyl (E)-diazene-1,2-dicarboxylate; ee=enantiomeric excess; eq.=equivalent; ESI=electrospray ionization; Et$_2$O=diethyl ether; EtOAc or EA=ethylacetate; EtOH=ethanol; FA=formic acid; Grubbs catalyst (1,3-Dimesitylimidazolin-2-ylidene)(tricyclohexylphosphine)ruthenium dichloride; h=hour(s); HATU=(dimethylamino)-N,N-dimethyl(3-oxido-1H-[1,2,3]triazolo[4,5-b]pyridinyl) methaniminium hexafluorophosphate; HCl=hydrochloric acid; H$_2$O$_2$=hydrogen peroxide; HP=high pressure; IPA=isopropylalcohol; LC=liquid chromatography; LiClO$_4$=lithium perchlorate; m=multiplet; mmol=millimole; mCPBA=meta-chloroperoxybenzoic acid; MeOH=methanol; min=minute(s); MeCN=acetonitrile; MeNO$_2$=nitromethane; MS=mass-spectrometery; NMP=N-methyl-2-pyrrolidone; NMR=nuclear magnetic resonance; Pd$_2$dba$_3$=Tris(dibenzylideneacetone)dipalladium (0); Pd(dppf)Cl$_2$=1,1'-bis(di-tort-butylphosphino)ferrocene palladium dichloride; PE=Petroleum ether; PPh$_3$= Triphenylphosphine; q=quartet; rt=room temperature; Rt or RT=retention time; s=singlet; sat=saturated; SFC=supercritical fluid chromatography; t=triplet; T3P=2,4,6-tripropyl-1,3,5,2,4,6-trioxatriphosphinane 2,4,6-trioxide; TBTU=2-(1H-benzo[d][1,2,3]triazol-1-yl)-1,1,3,3-tetramethylisouronium tetrafluoroborate; TFA=trifluoroacetic add; THF=tetrahydrofuran; TLC=thin layer chromatography; TMS=trimethylsilyl; Xantphos=4,5-bis(diphenylphosphino)-9,9-dimethylxanthene.

Synthesis of Starting Materials and Intermediates

Hepta-1,6-dien-4-ylbenzene D1

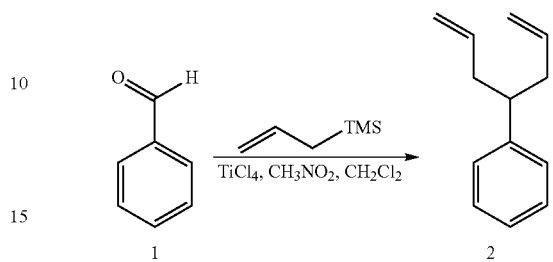

A solution of CH$_3$NO$_2$ (25.8 g) in DCM (400 mL) was treated with TiCl$_4$ solution (151 mL, 151 mmol, 1.0 M in DCM) at −60° C., then benzaldehyde (10 g, 94.2 mmol) in DCM (50 mL). The reaction was stirred at −60° C. for 0.5 h, then cooled to −78° C. prior to dropwise addition of allyltrimethylsilane (32 g, 282 mmol in DCM (50 mL). The reaction mixture was stirred at −78° C. for 2 h and −60° C. for 6 h, then poured into saturated NH$_4$Cl solution (500 mL) and extracted with dichloromethane (300 mL×2). The combined organic layers were washed with brine, dried over anhydrous sodium sulfate, filtered, concentrated. The residue was purified by column chromatography (petroleum ether) on silica gel to give hepta-1,6-dien-4-ylbenzene D1 (13.7 g, 84% yield) as colourless oil.

1-Fluoro-4-(hepta-1,6-dien-4-yl)benzene D2

TiCl$_4$ (56.9 mL, 0.516 mol) was added to MeNO$_2$ (69.5 mL, 1.29 mol) in DCM (1.5 L) at −78° C. over a period of 20 minutes under an N$_2$ atmosphere. The resulting mixture was stirred for 20 min and then treated with 4-fluorobenzaldehyde (40 g, 0.322 mol) in a dropwise manner over a period of 20 min. The resulting mixture was stirred at −70° C. for 1 h, then treated with allyltrimethylsilane (110 g, 0.967 mol) over a period of 0.5 h. The resulting mixture was stirred at −70° C. for 3 h and then warmed to 25° C. The reaction mixture was quenched with ice/water (1 L), extracted with DCM (3×400 mL), and the combined organic layers were dried (Na$_2$SO$_4$), filtered and evaporated to afford pale yellow oil. Silica gel flash chromatography, (0 to 5% EtOAc in pentane) gave 1-fluoro-4-(hepta-1,6-dien-4-yl) benzene (55.0 g, 90%) as a colourless oil. 1H NMR (300 MHz, CD$_3$OD) δ 7.14 (2H, m), 6.98 (2H, m), 5.65 (2H, ddt), 5.01-4.83 (4H, m), 2.72 (1H, tt), 2.51-2.18 (4H, m).

1-Fluoro-3-(hepta-1,6-dien-4-yl)benzene D3

TiCl$_4$ (56.9 mL, 515.65 mmol), MeNO$_2$ (69.5 mL, 1289.13 mmol) in DCM (1500 mL) were reacted with 3-fluorobenzaldehyde (40 g, 322.28 mmol) and allyltrimethylsilane (110 g, 966.85 mmol) at −78° C. as described for the synthesis of D1. Following work up, chromatography (Silica, 0 to 5% EtOAc in pentane) afforded 1-fluoro-3-(hepta-1,6-dien-4-yl)benzene D3 as a colourless oil which was used without further purification.

1-Fluoro-4-(hepta-1,6-dien-4-yl)-2-methoxybenzene D4

A solution of nitromethane (5.7 g, 4.5 eq.) in DCM (80 mL) and TiCl$_4$ (33.3 ml, 1.6 eq., 1M in DCM) was reacted with 4-fluoro-3-methoxybenzaldehyde (3.5 g, 1.0 eq.) in 20 mL DCM then allyltrimethylsilane (7.2 g, 3.0 eq.) as described for the synthesis of D1. Column chromatography (silica gel, petroleum ether) afforded 1-fluoro-4-(hepta-1,6-dien-4-yl)-2-methoxybenzene D4 (6.5 g, 98% yield) as yellow oil. 1H NMR (CDCl$_3$ 400 MHz) δ 7.00 (1H, dd), 6.76 (1H, dd), 6.73-6.67 (1H, m), 5.71-5.65 (2H, m), 5.02-4.95 (4H, m), 3.91 (3H, s), 2.72-2.67 (1H, m), 2.44-2.33 (4H, m).

Cyclopent-3-enylbenzene C1

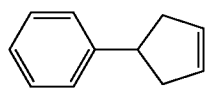

To a solution of D1 (13.7 g) in DCM (100 mL) was added Grubbs catalyst (1.0 g, 0.015 eq). The mixture was stirred at rt under nitrogen overnight at which stage TLC indicated no starting material remained. The reaction mixture was then washed with water (200 mL), brine (200 mL), then dried and evaporated. Column chromatography (n-heptane) on silica gel gave cyclopent-3-enylbenzene C1 (6.1 g, 55% yield) as colourless oil.

1-(Cyclopent-3-enyl)-4-fluorobenzene C2

Grubbs catalyst (2.68 g, 3.15 mmol) was added to 1-fluoro-4-(hepta-1,6-dien-4-yl)benzene (50 g, 0.263 mol) in DCM (500 mL) at 0° C. over a period of 20 min under nitrogen. The resulting mixture was stirred at 25° C. for 15 h. The solvent was removed under reduced pressure and the residue purified by column chromatography (0 to 5% EtOAc in petroleum ether) to afford 1-(cyclopent-3-en-1-yl)-4-fluorobenzene C2 (30.0 g, 70.4%) as a colourless liquid. 1H NMR (300 MHz, CD$_3$OD) δ 7.24 (2H, m), 6.97 (2H, m), 5.78 (2H, d), 3.46 (1H, tt), 2.81 (2H, m), 2.40 (2H, m).

1-(Cyclopent-3-enyl)-3-fluorobenzene C3

1-Fluoro-3-(hepta-1,6-dien-4-yl)benzene (3.5 g) in DCM (40 mL) was reacted with Grubbs catalyst (230 mg, 0.015 eq) as described for the synthesis of C1. Column chromatography (n-heptane) give C3 (2.1 g, 70%) as colourless oil. 1H NMR (CDCl$_3$, 400 MHz) δ 7.26-7.24 (1H, m), 7.04-6.88 (3H, m), 5.80-5.75 (2H, m), 3.49-3.45 (1H, m), 2.87-2.81 (2H, m), 2.48-2.41 (2H, m).

4-(cyclopent-3-enyl)-1-fluoro-2-methoxybenzene C4

1-Fluoro-4-(hepta-1,6-dien-4-yl)-2-methoxybenzene D4 (4.5 g, 1.0 eq.) in 50 ml DCM was reacted with was added Grubbs catalyst (450 mg, 0.025 eq.) as described for the synthesis of C1. Column chromatography on silica gel (Petroleum ether) gave 4-(cyclopent-3-enyl)-1-fluoro-2-methoxybenzene (3.1 g, 79% yield) as brown oil. 1H NMR (CDCl$_3$, 400 MHz) δ 6.99-6.94 (1H, m), 6.85 (1H, dd), 6.76-6.62 (1H, m), 5.78 (2H, s), 3.88 (3H, s), 3.44-3.38 (1H, m), 2.82 (2H, dd), 2.45-2.38 (2H, m).

3-Phenyl-6-oxabicyclo[3.1.0]hexane E1

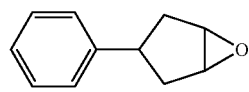

To a solution of cyclopent-3-enylbenzene C1 (6.1 g, 42.3 mmol) in DCM (80 mL) was added mCPBA (12.8 g, 1.5 eq, 85%) at 0° C. in a portionwise manner. The mixture was stirred at rt overnight. Saturated NaHSO$_3$ solution (400 ml) was then added and the suspension was stirred at rt for 30 min. The suspension was then diluted with water (200 mL), extracted with dichloromethane (200 ml) and the organic layer was washed with saturated sodium bicarbonate solution and brine. The combined organics were dried over anhydrous sodium sulfate, filtered and evaporated. The residue was purified by column chromatography (petroleum ether/EtOAc 20:1) on silica gel to afford 3-phenyl-6-oxabicyclo[3.1.0]hexane E1 (4.9 g, 73% yield) as colourless oil.

trans-3-(4-fluorophenyl)-6-oxabicyclo[3.1.0]hexane E2

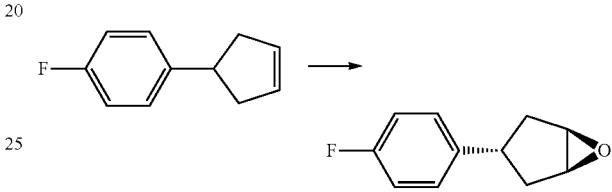

Formic acid (88%) (392 mL, 9.15 mol) was added dropwise to H$_2$O$_2$ (30%) (262 mL, 2.62 mol) cooled to 0° C. over a period of 1 h under air. 1-(Cyclopent-3-en-1-yl)-4-fluorobenzene C2 (20 g, 0.123 mol) in DCM (250 ml) was then added at 0° C. over a period of 3 h under air. The resulting mixture was then stirred at ambient temperature for 12 h, after which the solvent was then removed under reduced pressure. The crude product was purified by flash silica chromatography, (0 to 10% EtOAc in petroleum ether) to afford trans-3-(4-fluorophenyl)-6-oxabicyclo[3.1.0]hexane E2 (12.00 g, 54.6%) as a colourless oil. 1H NMR (300 MHz, CDCl$_3$) δ 7.15 (2H, m), 6.99 (2H, m), 3.60 (2H, s), 2.98 (1H, tt), 2.46 (2H, dd), 1.71 (2H, dd).

3-(3-Fluorophenyl)-6-oxabicyclo[3.1.0]hexane E3

1-(Cyclopent-3-enyl)-3-fluorobenzene C2 (2.1 g) in DCM (50 ml) and mCPBA (3.3 g, 1.5 eq, 85%) were reacted as described for the synthesis of E1. Silica gel chromatography (petroleum ether/EtOAc=20:1) gave E3 (1.1 g, 47%) as a colourless oil.

3-(4-fluoro-3-methoxyphenyl)-6-oxabicyclo[3.1.0] hexane E4 mCPBA (5.57 g, 2.0 eq.) and 4-(cyclopent-3-enyl)-1-fluoro-2-methoxybenzene C4 (3.1 g, 1.0 eq.) in 50 ml dichloromethane were reacted as described for the synthesis of E1. Column chromatography gave E4 as the trans isomer (1.3 g, 47% yield) and the cis isomer (300 mg, 9% yield) as colourless oils. Trans-E4 1H NMR (CDCl$_3$, 400 MHz) δ 7.00-6.95 (1H, m), 6.77 (1H, dd), 6.72-6.66 (1H, m), 3.87 (3H, s), 3.58 (2H, s), 2.98-2.91 (1H, m), 2.47-2.41 (2H, m), 1.71 (2H, dd). cis-E4 1H NMR (CDCl$_3$, 400 MHz) δ 6.99 (1H, dd), 6.92 (1H, dd), 6.75-6.73 (1H, m), 3.89 (3H, s), 3.57 (2H, s), 3.45-3.39 (1H, s), 2.33 (2H, dd), 2.08 (2H, dd).

tert-butyl (3R)-1-(2-hydroxy-4-phenylcyclopentyl) piperidin-3-ylcarbamate F1

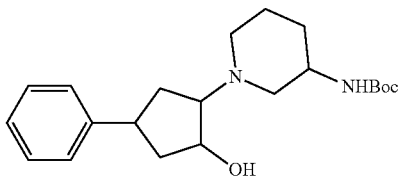 [SMILES: CC(C)(C)OC(=O)NC1CCCN(C2CC(c3ccccc3)CC2O)C1]

To a solution of 3-phenyl-6-oxabicyclo[3.1.0]hexane E1 (1.5 g) in CH₃CN (20 mL) was added (R)-tert-butyl piperidin-3-ylcarbamate (2.2 g, 1.2 eq) and LiClO₄ (2.0 g, 2.0 eq). The resulting suspension was refluxed overnight then cooled and filtered. The filtrate was evaporated and the residue was purified by column chromatography (petroleum ether/EtOAc 1:1) on silica gel to give tert-butyl (3R)-1-(2-hydroxy-4-phenylcyclopentyl)piperidin-3-ylcarbamate F1 (1.97 g, 59%) as yellow solid which was used without further purification.

tert-butyl (3R)-1-(4-(4-fluorophenyl)-2-hydroxycyclopentyl)piperidin-3-ylcarbamate F2a (R)-1,1'-Bi-2-naphthol (1.607 g, 5.61 mmol) in toluene (50 ml), was treated with dibutylmagnesium (7.29 ml, 1.0 M, 7.29 mmol in n-heptane) at 25° C. After 0.5 h stirring, the reaction was cooled to 0° C. and then trans-3-(4-fluorophenyl)-6-oxabicyclo[3.1.0]hexane E2 (10 g, 56.11 mmol) and tert-butyl (R)-piperidin-3-ylcarbamate (11.24 g, 56.11 mmol) in toluene (150 ml) were added. After overnight stirring, the reaction mixture was poured into crushed ice, the mixture partitioned between DCM and water. The aqueous layer was extracted again with DCM and the combined organic layers were washed with saturated NaHCO₃ and brine, then dried (sodium sulfate) and evaporated. Flash silica chromatography (0 to 10% MeOH in DCM) gave tert-butyl (3R)-1-(4-(4-fluorophenyl)-2-hydroxycyclopentyl)piperidin-3-ylcarbamate F2b (12.00 g, 56.5%) as a yellow oil. 1H NMR (300 MHz, CDCl₃) δ 7.20 (2H, ddt), 6.94-7.07 (2H, m), 4.94 (1H, s), 4.32 (1H, t), 3.78 (1H, s), 3.31 (1H, dtd), 2.72 (2H, dd), 2.53 (2H, s), 2.24 (1H, dt), 1.96-2.10 (2H, m), 1.52-1.86 (4H, m), 1.47 (10H, d). LCMS: m/z (ESI), [M+H]⁺=379.

tert-butyl N-[(3R,5R)-5-fluoro-1-[(1R,2R,4S)-4-(4-fluorophenyl)-2-hydroxy-cyclopentyl]-3-piperidyl] carbamate and tert-butyl N-[(3R,5R)-5-fluoro-1-[(1S,2S,4R)-4-(4-fluorophenyl)-2-hydroxy-cyclopentyl]-3-piperidyl]carbamate F2b

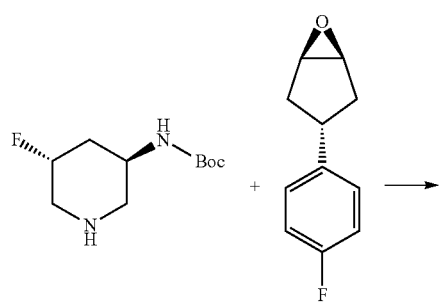

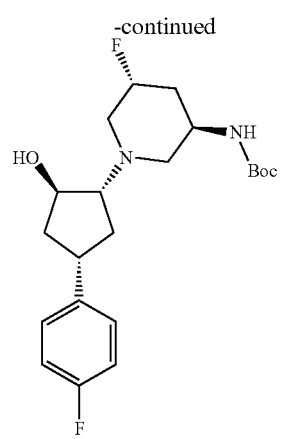

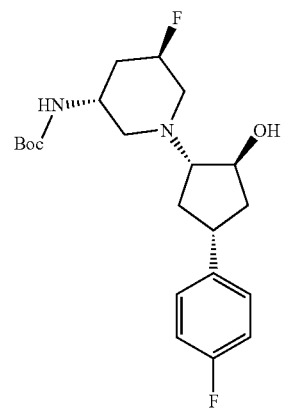

Trans-3-(4-fluorophenyl)-6-oxabicyclo[3.1.0]hexane E2 (1.225 g, 6.87 mmol) was added to tert-butyl ((3R,5R)-5-fluoropiperidin-3-yl)carbamate (1 g, 4.58 mmol), and Na₂CO₃ (1.457 g, 13.74 mmol) in EtOH (10 mL) at rt. The resulting mixture was stirred at 90° C. for 12 h. The solvent was then removed under reduced pressure and the crude product was purified by silica gel flash column chromatography (0 to 10% MeOH in DCM) to give a mixture of the above named stereoisomers, F2b, (1.030 g, 56.7%) as a yellow oil. LCMS: m/z (ES+), [M+H]+=397.

tert-butyl 4,4-difluoro-1-(4-(4-fluorophenyl)-2-hydroxycyclopentyl)piperidin-3-ylcarbamate F2c A mixture of trans 3-(4-fluorophenyl)-6-oxabicyclo[3.1.0]hexane E2 (450 mg, 1.2 eq.), tert-butyl 4,4-difluoropiperidin-3-ylcarbamate (500 mg, 1.0 eq.) and Na₂CO₃ (450 mg, 2.0 eq.) in ethanol (8 mL) was stirred under microwave condition: 130° C., 16 h. The mixture was diluted with dichloromethane and filtered the filtrate concentrated and the residue was purified by silica gel flash column chromatography (petroleum ether/EtOAc 90:10 to 60:40) to give tert-butyl 4,4-difluoro-1-(4-(4-fluorophenyl)-2-hydroxycyclopentyl)piperidin-3-ylcarbamate F2c (250 mg, 28% yield) as light yellow thick oil.

tert-butyl (3R)-5,5-difluoro-1-(4-(4-fluorophenyl)-2-hydroxycyclopentyl)piperidin-3-ylcarbamate F2d To a solution of (1R,3S,5S)-3-(4-fluorophenyl)-6-oxabicyclo[3.1.0]hexane (trans epoxide) E2 (300 mg, 1.0 eq.) in 10 mL anhydrous ethanol was added (R)-tert-butyl 5,5-difluoropiperidin-3-ylcarbamate (398 mg, 1.0 eq.) and sodium carbonate (357 mg, 2.0 eq.) in a sealed vial. The suspension was irradiated in microwave at 130° C. for 7 h. The suspension was filtered and concentrated. The residue was purified by column on silica gel (petroleum ether/EtOAc, 0 to 10% gradient then 20% EtOAc in DCM) to afford compound tert-butyl (3R)-5,5-difluoro-1-(4-(4-fluorophenyl)-2-hydroxycyclopentyl)piperidin-3-ylcarbamate F2d (290 mg, 42% yield) as white solid.

tert-butyl (3R)-1-(4-(3-fluorophenyl)-2-hydroxycyclopentyl)piperidin-3-ylcarbamate F3

To a solution of 3-(3-fluorophenyl)-6-oxabicyclo[3.1.0]hexane E3 (300 mg) in CH$_3$CN (10 mL) was added (R)-tert-butyl piperidin-3-ylcarbamate (404 mg, 1.2 eq), LiClO$_4$ (358 mg, 2.0 eq). The reaction mixture was refluxed overnight. TLC showed the starting material was consumed completely. The mixture was concentrated and the residue was added ethyl acetate (50 mL) and water (50 mL). The mixture was extracted with ethyl acetate. The organic layer was dried over Na$_2$SO$_4$, concentrated and purified by silica gel column chromatography eluted with ethyl acetate to give tert-butyl (3R)-1-(4-(3-fluorophenyl)-2-hydroxycyclopentyl)piperidin-3-ylcarbamate F3 (580 mg, 90%).

tert-butyl (3R)-1-(4-(4-fluoro-3-methoxyphenyl)-2-hydroxycyclopentyl)piperidin-3-ylcarbamate F4

To a solution of 3-(4-fluoro-3-methoxyphenyl)-6-oxabicyclo[3.1.0]hexane E4 (100 mg, 1.0 eq.) in 3 mL anhydrous ethanol was added (R)-tert-butyl piperidin-3-ylcarbamate (115 mg, 1.2 eq.) and sodium carbonate (101 mg, 2.0 eq.) in a sealed vial. The suspension was irradiated in microwave at 130° C. for 6 h. The suspension was filtered and concentrated. Column chromatography on the residue (silica gel DCM/methanol, 0 to 3% methanol) gave F4 (140 mg, 71% yield) as colourless solid. 1H NMR (CDCl$_3$ 400 MHz) δ 6.99 (1H, dd), 6.86 (1H, dd), 6.75-6.71 (1H, m), 4.92 (1H, br s), 4.27-4.21 (1H, m), 3.89 (3H, s), 3.75 (1H, br s), 3.10-3.06 (2H, m), 2.88-2.75 (2H, m), 2.53 (2H, m), 2.41-2.35 (2H, m), 2.15-2.05 (1H, m), 1.90-1.66 (6H, m), 1.40 (9H, d).

Compound 1

Step 1. tert-butyl (3R)-1-(4-(4-fluorophenyl)-2-(2H-1,2,3-triazol-2-yl)cyclopentyl)piperidin-3-ylcarbamate A solution of trans tert-butyl (3R)-1-(4-(4-fluorophenyl)-2-hydroxycyclopentyl)piperidin-3-ylcarbamate F2a (600 mg, 1.59 mmol), 1H-1,2,3-triazole (219 mg, 3.17 mmol), DIAD (0.401 mL, 2.06 mmol) and PPh$_3$ (541 mg, 2.06 mmol) in DCM (20 mL) were stirred at rt for 2 hours. The solvent was removed under reduced pressure and the residue purified by silica gel flash column chromatography, (10 to 50% MeCN in water) to afford the title compound (450 mg, 66.1%) as a white solid. The crude product was separated on a Waters SFC 350 Preparative System [Column: CHIRALART Amylose-SA, 2×25 cm, 5 μm; Mobile Phase A: CO$_2$: 80, Mobile Phase B: MeOH (2 mM NH$_3$-MeOH): 20; Flow rate: 40 mL/min; 220 nm]. Two fractions were obtained as white solids: fraction 1 (300 mg, 66.7%, RT1:3.03) and fraction 2 (100 mg, 22.22%, RT2:4.58).

Fraction 1 was further separated on a Waters SFC 350 Preparative System, Column: (R,R)-WHELK-O1-Kromasil, 5 cm×25 cm (5 μm); Mobile Phase A: CO$_2$: 85, Mobile Phase B: MeOH (2 mM NH$_3$-MeOH):15; Flow rate: 40 mL/min; 220 nm; RT1:2.31; RT2:2.71. The fractions containing the desired compound were evaporated to dryness to afford isomer 1 (120 mg, 40%, 100% ee) and isomer 2 (120 mg, 40%, 98.4% ee) as white solids. LCMS m/z (ESI), [M+H]$^+$=430.

Step 2. 1-[4-(4-fluorophenyl)-2-(triazol-2-yl)cyclopentyl]piperidin-3-amine Compound 1

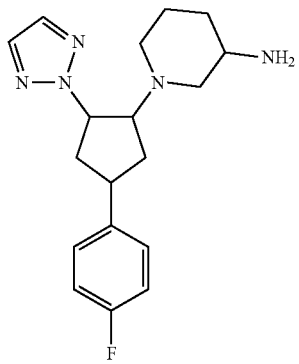 [SMILES: NC1CCCN(C2CC(c3ccc(F)cc3)CC2n2nccn2)C1]

A solution of isomer 1 (120 mg, 0.28 mmol) obtained in step 1 in TFA (1 mL) and DCM (5 ml) was stirred at rt for 1 h. The solvent was then removed under reduced pressure and the crude product was purified by preparative HPLC [Column: XBridge Prep OBD C18 Column 30×150 mm 5 μm; Mobile Phase A: Water (containing 10 mmol/L NH$_4$HCO$_3$+0.1% aq. NH$_3$), Mobile Phase B: MeCN; Flow rate: 60 mL/min; Gradient: 25% B to 54% B in 8 min; 254/220 nm; Rt: 6.87 min] to afford Compound 1 (70.0 mg, 76%) as a white solid. LCMS: m/z (ESI), [M+H]$^+$=330; 1H NMR (300 MHz, CD$_3$OD) δ 7.71 (2H, s), 7.31 (2H, ddd), 7.10-6.96 (m, 2H), 5.23 (1H, ddd), 3.58 (2H, ddt), 3.08-2.72 (3H, m), 2.52-2.17 (3H, m), 1.86 (4H, ddd), 1.75-1.45 (2H, m), 1.11 (1H, qd). 19F NMR (300 MHz, CD$_3$OD, 24° C.) δ −118.73 (s, 1F).

Compound 2

Step 1. tert-butyl (3R)-1-(2-(4-cyano-1H-pyrazol-1-yl)-4-(4-fluorophenyl)cyclopentyl)piperidin-3-yl carbamate To a mixture of tert-butyl (3R)-1-(4-(4-fluorophenyl)-2-hydroxycyclopentyl)piperidin-3-ylcarbamate F2a (5 g, 13.21 mmol), 1H-pyrazole-4-carbonitrile (1.230 g, 13.21 mmol), PPh$_3$ (5.20 g, 19.82 mmol) in DCM (100 mL) was added DTAD (4.56 g, 19.82 mmol). The reaction was stirred at 25° C. for 16 hours. The resulting solution was washed with sat. NaHCO$_3$ and brine. The organic layer was dried over Na$_2$SO$_4$, filtered, then concentrated to dryness. The residue was purified by C18 flash column chromatography (elution gradient 40 to 55% MeCN in water (with 0.2% ammonia) to afford the desired product as a yellow oil. LCMS: m/z (ESI), [M+H]$^+$=454. Separation by preparative chiral-HPLC [Chiralpak IA, 2×25 cm, 5 μm; Mobile Phase A: Hexanes-HPLC, Mobile Phase B: IPA-HPLC; Flow rate: 20 mL/min; Gradient: A:B=70:30, 17.5 min] gave the title compound (isomer 1, 2.60 g, 47.3%) as a yellow oil.

Step 2. 1-[2-(3-amino-1-piperidyl)-4-(4-fluorophenyl)cyclopentyl]pyrazole-4-carbonitrile Compound 2

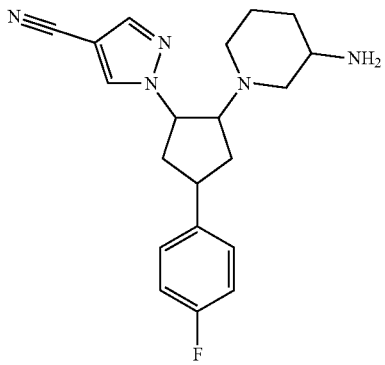 [SMILES: N#Cc1cnn(C2CC(c3ccc(F)cc3)CC2N2CCCC(N)C2)c1]

To isomer 1 obtained in step 1 (2.6 g, 5.73 mmol) was added to HCl in dioxane (50 mL, 200 mmol). The resulting mixture was stirred at 20° C. for 4 hours, then concentrated to dryness. The residue was treated with Et$_2$O/MeOH (10/1) and the resultant solid was collected, then treated with diluted with sat. Na$_2$CO$_3$ and then extracted into EtOAc. The organic layer was dried over Na$_2$SO$_4$ and concentrated to dryness to give Compound 2 (1.358 g, 67.0%) as a light-yellow solid. 1H NMR (300 MHz, DMSO-d$_6$) δ 8.74 (1H, s), 8.11 (1H, s), 7.30-7.43 (2H, m), 7.05-7.20 (2H, m), 4.87-5.00 (1H, m), 3.26-3.41 (2H, m), 2.79 (1H, d), 2.50-2.72 (2H, m), 2.09-2.32 (3H, m), 1.96 (1H, dd), 1.50-1.79 (4H, m), 1.37 (3H, d), 0.83-1.02 (1H, m). LCMS: m/z (ESI), [M+H]$^+$=354.

Compound 3

Step 1. tert-butyl (3R)-1-(2-(3-cyano-1H-pyrazol-1-yl)-4-(4-fluorophenyl)cyclopentyl) piperidin-3-yl carbamate DTAD (243 mg, 1.06 mmol) was added dropwise to F2a (200 mg, 0.53 mmol), 1H-pyrazole-3-carbonitrile (49.2 mg, 0.53 mmol) and PPh$_3$ (277 mg, 1.06 mmol) in DCM (15 mL) at 0° C. under nitrogen. The resulting mixture was stirred at 25° C. for 3 hours. The organic layer was washed with NaHCO$_3$ aq and the solvent was removed under reduced pressure. The crude product was purified by reverse phase chromatography (C18 column) using decreasingly polar mixtures of water (containing 0.1% NH$_3$) and MeCN as eluent. Fractions containing the desired compound were evaporated to dryness to afford tert-butyl (3R)-1-(2-(3-cyano-1H-pyrazol-1-yl)-4-(4-fluorophenyl)cyclopentyl)piperidin-3-ylcarbamate (240 mg, 100%) as a white solid. This solid was purified by preparative TLC (DCM:MeOH=40:1), to afford tert-butyl ((3R)-1-(2-(3-cyano-1H-pyrazol-1-yl)-4-(4-fluorophenyl)cyclopentyl)piperidin-3-yl)carbamate fraction 1 (90 mg, 37.5%) as a yellow solid and tert-butyl ((3R)-1-(2-(3-cyano-1H-pyrazol-1-yl)-4-(4-fluorophenyl)cyclopentyl)piperidin-3-yl)carbamate fraction 2 (70.0 mg, 29.2%) as a yellow solid. LCMS for both fraction: m/z (ESI), [M+H]$^+$=454; Fraction 1 (90 mg, 0.20 mmol) was purified by preparative chiral-HPLC [Chiralpak IE column, eluting isocratically with 5% IPA in Hexanes (modified with 0.1% DEA) as eluent to afford tert-butyl ((3R)-1-(2-(3-cyano-1H-pyrazol-1-yl)-4-(4-fluorophenyl)cyclopentyl)piperidin-3-yl)carbamate isomer 1 (35.0 mg, 38.9%, isomer 1, 99.3% ee) as a yellow solid and isomer 2 (30.0 mg, 33.3%, isomer 2, 99% ee) as a yellow solid. LCMS: (isomer 1) m/z (ESI), [M+H]$^+$=454; (isomer 2) m/z (ESI), [M+H]$^+$=454.

Step 2. 1-[2-(3-amino-1-piperidyl)-4-(4-fluorophenyl)cyclopentyl]pyrazole-3-carbonitrile Compound 3

TFA (0.5 mL, 6.49 mmol) was added to above tert-butyl ((3R)-1-(2-(3-cyano-1H-pyrazol-1-yl)-4-(4-fluorophenyl)cyclopentyl)piperidin-3-yl)carbamate isomer 1 (20 mg, 0.04 mmol) in DCM (3 mL). The resulting mixture was stirred at 25° C. for 2 hours. Preparative HPLC Column [X Select CSH Prep C18 OBD Column, 5 μm, 19*150 mm; Mobile Phase A: Waters (0.05% TFA), Mobile Phase B: MeCN; Flow rate: 20 ml/min; Gradient: 12% B to 32% B in 7 min; 254; 220 nm] Compound 3, isomer 1, (17.00 mg, 51.8%) as a white solid. 1H NMR (300 MHz, CD$_3$OD) δ 7.75 (dd, 1H), 7.28-7.42 (m, 2H), 6.96-7.14 (m, 3H), 5.17 (ddd, 1H), 3.81 (dt, 1H), 3.60 (s, 1H), 3.41 (dt, 2H), 3.14 (d, 1H), 2.67 (s, 1H), 2.29-2.63 (m, 5H), 1.90 (dt, 2H), 1.44-1.74 (m, 2H). 19F NMR (300 MHz, CD$_3$OD) δ −77.287 (m, 10F), −118.609 (s, 1F). LCMS: m/z (ESI), [M+H]$^+$=354.

Compound 4

Step 1. tert-butyl (3R)-1-(2-(3-cyano-1H-pyrrol-1-yl)-4-(4-fluorophenyl)cyclopentyl)piperidin-3-ylcarbamate To a solution of tert-butyl (3R)-1-(4-(4-fluorophenyl)-2-hydroxycyclopentyl)piperidin-3-ylcarbamate F2a (250 mg, 0.66 mmol), 1H-pyrrole-3-carbonitrile (60.8 mg, 0.66 mmol), PPh$_3$ (346 mg, 1.32 mmol) in DCM (15 mL), was reacted with DTAD (304 mg, 1.32 mmol) as described for the synthesis of compound 3 above. C18 flash column chromatography, elution gradient 20 to 60% MeCN in water (with 0.3% NH$_3$H$_2$O) delivered tert-butyl (3R)-1-(2-(3-cyano-1H-pyrrol-1-yl)-4-(4-fluorophenyl)cyclopentyl)piperidin-3-ylcarbamate (180 mg, 60.2%) as a colourless oil. Preparative chiral-HPLC [Phenomenex Lux 5 u Cellulose-4, AXIA Packed, 250*21.2 mm, 5 μm; Mobile Phase A: Hexanes-HPLC, Mobile Phase B: IPA-HPLC; Flow rate: 20 ml/min; Gradient: A:B=80:20 in 21 min; 254/220 nm; RT1:12.5; RT2:17.2 afforded tert-butyl (3R)-1-(2-(3-cyano-1H-pyrrol-1-yl)-4-(4-fluorophenyl)cyclopentyl)piperidin-3-ylcarbamate isomer 1 (70.0 mg, 38.9%, isomer 1) as a yellow oil and tert-butyl (3R)-1-(2-(3-cyano-1H-pyrrol-1-yl)-4-(4-fluorophenyl)cyclopentyl)piperidin-3-ylcarbamate isomer 2 (70.0 mg, 38.9%, isomer 2) as a yellow oil. LCMS for both isomers: m/z (ESI), [M+H]$^+$=453.

Step 2. 1-[2-(3-amino-1-piperidyl)-4-(4-fluorophenyl)cyclopentyl]pyrrole-3-carbonitrile Compound 4

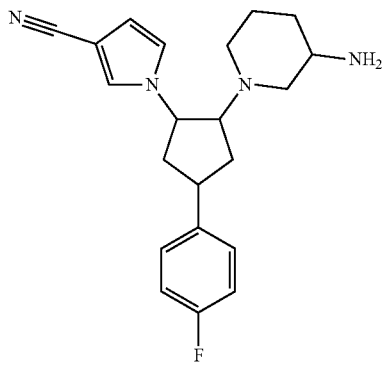 [SMILES: N#Cc1ccn(C2CC(c3ccc(F)cc3)CC2N2CCCC(N)C2)c1]

TFA (1 ml, 12.98 mmol) was added to the above tert-butyl (3R)-1-(2-(3-cyano-1H-pyrrol-1-yl)-4-(4-fluorophenyl)cyclopentyl)piperidin-3-ylcarbamate isomer 2 (70 mg, 0.18 mmol) in DCM (5 ml). The resulting mixture was stirred at 25° C. for 2 hours. Standard work-up, then preparative HPLC [XBridge Prep OBD C18 Column 30×150 mm 5 μm; Mobile Phase A: Waters (10 mmoL/L NH$_4$HCO$_3$), Mobile Phase B: MeCN; Flow rate: 20 ml/min; Gradient: 35% B to 39% B in 35 min; 254/220 nm) gave Compound 4, isomer 2 (20.00 mg, 24.25%) as a white solid. 1H NMR (300 MHz, CD$_3$OD) δ 1.36 (dtd, 2H), 1.50-1.93 (m, 3H), 2.13-2.45 (m, 5H), 2.63 (dt, 1H), 2.86-2.97 (m, 1H), 3.05 (dq, 1H), 3.33-3.56 (m, 2H), 4.71 (ddt, 1H), 6.48 (dd, 1H), 6.98-7.12 (m, 3H), 7.27-7.40 (m, 2H), 7.66 (t, 1H). 19F NMR (300 MHz, CD$_3$OD) δ −76.962 (m, 3F), −119.017 (s, 1F). LCMS: m/z (ESI), [M+H]$^+$=353.

Compound 5

Step 1. tert-butyl (3R)-1-(2-(4-cyano-1H-1,2,3-triazol-1-yl)-4-(4-fluorophenyl)cyclopentyl) piperidin-3-ylcarbamate A Mitsunobu reaction of F2a (350 mg, 0.92 mmol), 1H-1,2,3-triazole-4-carbonitrile (87 mg, 0.92 mmol), PPh$_3$ (485 mg, 1.85 mmol) in DCM (15 mL) and DTAD (426 mg, 1.85 mmol) was performed as described for the synthesis of compound 3 above. Flash C18 column chromatography [elution gradient 20 to 60% MeCN in water (with 0.3% aq. NH$_3$)] gave a colourless oil (220 mg, 52.3%).

Preparative chiral-HPLC on this oil [Phenomenex Lux 5 u Cellulose-4, AXIA Packed, 250*21.2 mm, 5 μm; Mobile Phase A: Hexanes-HPLC, Mobile Phase B: IPA-HPLC; Flow rate: 20 mL/min; Gradient: 30 B to 30 B in 12 min; 254/220 nm; RT1:6.2; RT2:8.4]. gave tert-butyl (3R)-1-(4-(4-fluorophenyl)-2-hydroxycyclopentyl)piperidin-3-ylcarbamate (95 mg, 43.2%, fraction 1) as a colourless oil and tert-butyl (3R)-1-(4-(4-fluorophenyl)-2-hydroxycyclopentyl)piperidin-3-ylcarbamate (95 mg, 43.2%, fraction 2) as a colourless oil. LCMS for both isomers: m/z (ESI), [M+H]$^+$=455.

Step 2. 1-[2-(3-amino-1-piperidyl)-4-(4-fluorophenyl)cyclopentyl]triazole-4-carbonitrile Compound 5

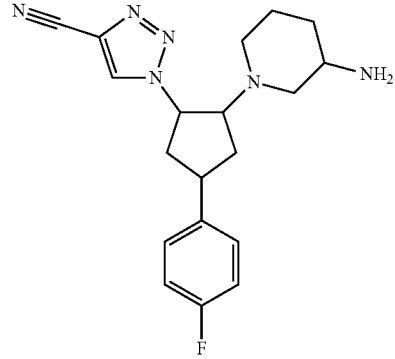 [SMILES: N#Cc1cn(C2CC(c3ccc(F)cc3)CC2N2CCCC(N)C2)nn1]

TFA (1 mL, 12.98 mmol) was added to tert-butyl (3R)-1-(4-(4-fluorophenyl)-2-hydroxycyclopentyl)piperidin-3-ylcarbamate fraction 1 (60 mg, 0.13 mmol) in DCM (5 mL). The resulting mixture was stirred at 25° C. for 2 h and solvent was then removed under reduced pressure. Purification by preparative HPLC Column: XBridge Shield RP18 OBD Column, 5 μm; 19*150 mm; Mobile Phase A: Waters (0.05% aq. NH$_3$), Mobile Phase B: MeCN; Flow rate: 20 ml/min; Gradient: 20% B to 47% B in 7 min; 254/220 nm gave Compound 5, isomer 1 (73.0 mg, 56.4%) as a white solid. 1H NMR (300 MHz, CD$_3$OD) δ 1.58-1.71 (m, 1H), 1.75 (s, 1H), 1.97 (s, 3H), 2.50 (s, 3H), 2.74 (br s, 2H), 2.95 (m, 1H), 3.22 (m, 1H), 3.46 (m, 1H), 3.61-3.72 (m, 1H), 3.92 (br.s, 1H), 5.53 (s, 1H), 7.01-7.15 (m, 2H), 7.31-7.42 (m, 2H), 8.34 (dd, 1H). 19F NMR (300 MHz, CD$_3$OD) δ −77.222 (m, 16F), −118.395 (s, 1F), LCMS: m/z (ESI), [M+H]$^+$=355.

Compound 6

Step 1. Synthesis of tert-butyl (3R,5R)-1-(2-(4-cyano-1H-pyrazol-1-yl)-4-(4-fluorophenyl)cyclopentyl)-5-fluoropiperidin-3-ylcarbamate Mitsunobu reaction of DIAD (235 mg, 1.16 mmol), PPh$_3$ (305 mg, 1.16 mmol), 1H-pyrazole-4-carbonitrile (64.9 mg, 0.70 mmol) and F2b (220 mg, 0.58 mmol) in DCM (20 mL) was performed at rt. The crude product from work-up was purified by C18 flash column chromatography, elution gradient 0 to 48% MeCN in water (contains 0.3% NH$_4$HCO$_3$). Pure fractions were evaporated to dryness to afford a pale yellow solid (220 mg, 80%). LCMS: m/z (ESI), [M+H]$^+$ =472. The crude product was further purified by preparative chiral-HPLC [Chiralpak IA column, eluting isocratically with 30% EtOH in Hexanes (modified with 0.1% DEA) as eluent to give tert-butyl (3R,5R)-1-(2-(4-cyano-1H-pyrazol-1-yl)-4-(4-fluorophenyl)cyclopentyl)-5-fluoropiperidin-3-ylcarbamate isomer 1 (100 mg, 45.5%, 100% ee) as a pale yellow solid and tert-butyl (3R,5R)-1-(2-(4-cyano-1H-pyrazol-1-yl)-4-(4-fluorophenyl)cyclopentyl)-5-fluoropiperidin-3-ylcarbamate isomer 2 (98 mg, 44.5%, isomer 2, 100% ee) as a white solid. LCMS for both isomers: m/z (ESI), [M+H]$^+$=472.

Step 2. 1-[2-(3-amino-5-fluoro-1-piperidyl)-4-(4-fluorophenyl)cyclopentyl]pyrazole-4-carbonitrile
Compound 6

Step 2. 1-[2-(3-amino-4,4-difluoro-1-piperidyl)-4-(4-fluorophenyl)cyclopentyl]pyrazole-4-carbonitrile
Compound 7

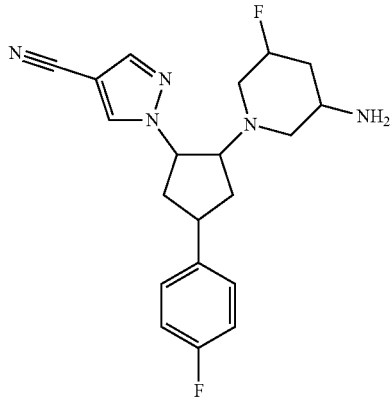 [SMILES: N#Cc1cnn(C2CC(c3ccc(F)cc3)CC2N2CC(N)CC(F)C2)c1]

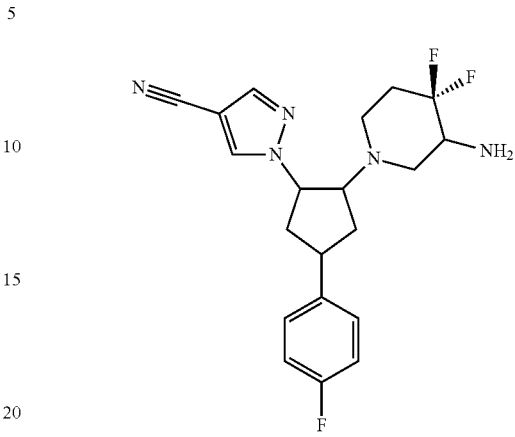

Boc-deprotection of tert-butyl (3R, 5R)-1-(2-(4-cyano-1H-pyrazol-1-yl)-4-(4-fluorophenyl)cyclopentyl)-5-fluoropiperidin-3-ylcarbamate isomer 1 (100 mg, 0.21 mmol) was carried out with TFA (3 mL, 38.94 mmol) in DCM (20 mL) at 0° C. After standard work-up, the crude product was purified by preparative HPLC [(XBridge Prep C18 OBD column, 5 μm silica, 19 mm diameter, 150 mm length), using decreasingly polar mixtures of water (containing 0.05% TFA) and MeCN as eluents]. Fractions containing the desired compound were evaporated to dryness to afford Compound 6, isomer 1 as the TFA salt (68.0 mg, 37.1%) as a white solid. LCMS: m/z (ESI), [M+H]$^+$=372. 1H NMR (400 MHz, CD$_3$OD) 8.52-8.44 (1H, d), 8.03-7.96 (1H, s), 7.41-7.29 (2H, m), 7.13-7.00 (2H, m), 5.06-4.95 (1.5H, m), 4.81 (0.5H, s) 3.79-3.64 (1H, dt), 3.66-3.49 (2H, m), 3.14-3.03 (1H, d), 3.03-2.89 (1H, q), 2.79-2.60 (1H, dd), 2.49-2.29 (4H, ddd), 2.26-2.15 (1H, d), 1.97-1.74 (2H, m). 19F NMR (282 MHz, CD$_3$OD) δ −77.36, −118.84, −185.37.

Compound 7

Step 1. tert-butyl 1-(2-(4-cyano-1H-pyrazol-1-yl)-4-(4-fluorophenyl)cyclopentyl)-4,4-difluoropiperidin-3-yl carbamate Mitsunobu reaction of di-tert-butyl (E)-diazene-1,2-dicarboxylate (220 mg, 0.21 mmol) F2c (220 mg, 0.53 mmol), 1H-pyrazole-4-carbonitrile (10 mg, 0.11 mmol) and PPh$_3$ (56.4 mg, 0.21 mmol) in DCM (10 mL) at 5° C. under nitrogen, gave after standard work-up and flash alumina chromatography (elution gradient 0 to 60% MeCN in water) tert-butyl 1-(2-(4-cyano-1H-pyrazol-1-yl)-4-(4-fluorophenyl)cyclopentyl)-4,4-difluoropiperidin-3-ylcarbamate (120 mg, 46%) as a colourless oil. The crude product was further purified by preparative chiral-HPLC [(Column: Phenomenex Lux 5 u Cellulose-4, AXIA Packed, 2.12*25 cm, 5 μm; Mobile Phase A: Hexanes-HPLC, Mobile Phase B: EtOH-HPLC; Flow rate: 20 ml/min; Gradient: A:B=80:20 in 40 min; 254/220 nm; RT1:10.664; RT2:13.923)] to afford 3 isomers (all white solid and m/z (ESI), [M+H]$^+$=490.4): isomer 1 (50.0 mg, 41.7%, 98% ee), isomer 2 (40.0 mg, 33.3%, 98% ee) and isomer 3 (30.0 mg, 25.00%, 100% ee; LCMS for all isomers: m/z (ESI), [M+H]$^+$=490.

Boc deprotection of tert-butyl 1-(2-(4-cyano-1H-pyrazol-1-yl)-4-(4-fluorophenyl)cyclopentyl)-4,4-difluoropiperidin-3-ylcarbamate isomer 2 (40 mg, 0.08 mmol) in DCM (3 ml) at 25° C. with TFA (47.5 mg, 0.49 mmol) gave, after preparative HPLC (Column: XBridge Prep C18 OBD Column 19×150 mm 5 μm; Mobile Phase A: Water (10 mmol/L NH$_4$HCO$_3$), Mobile Phase B: MeCN; Flow rate: 20 mL/min; Gradient: 46% B to 47% B in 7 min; 254/220 nm; Rt: 6.05 min) Compound 7 (15.00 mg, 47.1%) as a yellow solid. 1H NMR (300 MHz, CD$_3$OD) δ 1.70-2.03 (2H, m), 2.05-2.24 (1H, m), 2.25-2.45 (4H, m), 2.61 (2H, dddd), 2.80-3.11 (2H, m), 3.45-3.87 (2H, m), 4.94-5.03 (1H, m), 6.97-7.16 (2H, m), 7.26-7.45 (2H, m), 7.97 (1H, s), 8.46 (1H, s). 19F NMR (282 MHz, CD$_3$OD) δ −119.11−−118.71 (m), −107.36, −106.52. LCMS: m/z (ESI), [M+H]$^+$=390.

Compound 8

Step 1. tert-butyl (3R)-1-(4-(4-fluorophenyl)-2-(1H-pyrazol-1-yl)cyclopentyl)piperidin-3-ylcarbamate Mitsunobu reaction of F2a (10 g, 26.42 mmol), 1H-pyrazole (18 g, 264.40 mmol), PPh$_3$ (14 g, 53.38 mmol) and DTAD (12 g, 52.11 mmol) in DCM (1.5 L) was performed at 0° C. under nitrogen. After standard work up C18 flash column chromatography, (0 to 100% MeCN in water) gave the crude product (9.80 g, 87%) as a yellow oil. LCMS: m/z (ESI), [M+H]$^+$=429; 1H NMR (400 MHz, CDCl$_3$) δ 1.47 (9H, d), 1.52-1.82 (6H, m), 2.20-2.55 (6H, m), 2.66 (1H, d), 3.53-3.81 (2H, m), 4.75 (2H, s), 6.27 (1H, dt), 7.01 (2H, t), 7.23 (2H, td), 7.48-7.59 (2H, m). The crude product (4.5 g) was purified by on a Waters SFC 350 Preparative System [Phenomenex Lux 5 u Cellulose-3, 5 cm×25 cm, 5 μm; Mobile Phase A: CO$_2$:80%, Mobile Phase B: MeOH (0.1% isopropylamine): 20%; Flow rate: 160 mL/min; 220 nm; RT1:3.93; RT2:4.58] to afford tert-butyl (3R)-1-(4-(4-fluorophenyl)-2-(1H-pyrazol-1-yl)cyclopentyl)piperidin-3-ylcarbamate (2.000 g, 44.4%, 98.7% ee, isomer 1) as a yellow solid.

Step 2. 1-[4-(4-fluorophenyl)-2-pyrazol-1-yl-cyclopentyl]piperidin-3-amine Compound 8

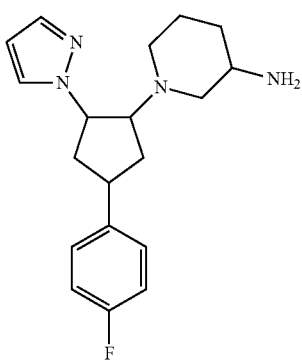 [SMILES: NC1CCCN(C2CC(c3ccc(F)cc3)CC2n2cccn2)C1]

Boc-deprotection of tert-butyl ((R)-1-((1S,2S,4R)-4-(4-fluorophenyl)-2-(1H-pyrazol-1-yl)cyclopentyl) piperidin-3-yl) carbamate isomer 1 (2.0 g, 4.667 mmol) in DCM (30.0 mL) with TFA (6.0 mL) was performed as described above. Flash silica chromatography (0 to 10% MeOH in DCM, 2% Ammonium hydroxide in DCM was used to basify the silica column) gave Compound 8 (1.400 g, 91%) as a white solid. LCMS: m/z (ESI), [M+H]⁺=329; 1H NMR (300 MHz, CD₃OD) δ 1.10 (1H, dtd), 1.48-2.08 (6H, m), 2.13-2.49 (3H, m), 2.77 (2H, ddt), 2.89-3.02 (1H, m), 3.54 (2H, ddt), 4.91 (1H, td), 6.31 (1H, t), 7.03 (2H, ddt), 7.28-7.39 (2H, m), 7.53 (1H, d), 7.79 (1H, dd). 19F NMR (376 MHz, CD₃OD) δ −119.16.

Compound 9

Step 1. tert-butyl (3R, 5R)-5-fluoro-1-(4-(4-fluorophenyl)-2-(1H-pyrazol-1-yl) cyclopentyl) piperidin-3-yl carbamate DTAD (1.742 g, 7.57 mmol) was added to F2b (1.0 g, 2.52 mmol), 1H-pyrazole (0.859 g, 12.61 mmol) and PPh₃ (1.985 g, 7.57 mmol) in DCM (50 mL) cooled to 0° C. over a period of 5 minutes under nitrogen. The resulting mixture was stirred at rt for 3 hours. The crude product was purified by preparative HPLC [XBridge Prep OBD C18 Column 19*250 mm, 5 μm; Mobile Phase A: Water (0.05% aq. NH₃), Mobile Phase B: MeCN; Flow rate: 60 mL/min; Gradient: 40% B to 50% B in 7 min; 220,254 nm; RT: 6.48 min] to afford tert-butyl (3R,5R)-5-fluoro-1-(4-(4-fluorophenyl)-2-(1H-pyrazol-1-yl) cyclopentyl) piperidin-3-yl carbamate (0,700 g, 62.2%) as a white solid. LCMS: m/z (ESI), [M+H]+=447.3; 1H NMR (CDCl₃) δ 7.58 (d, 1H), 7.51 (t, 1H), 7.24 (ddd, 2H), 7.11-6.94 (m, 2H), 6.29 (q, 1H), 4.73 (d, 2H), 3.68-3.46 (m, 3H), 2.83 (s, 1H), 2.74-2.52 (m, 2H), 2.39 (t, 3H), 2.34-2.19 (m, 1H), 2.00 (s, 1H), 1.78 (dt, 2H), 1.63 (s, 1H), 1.48 (d, 9H). Preparative SFC on a Waters SFC 350 Preparative System [Chiralpak AS-H, 5*25 cm, 5 μm; Mobile Phase A: CO₂:70%, Mobile Phase B: MeOH-Preparative: 30%; Flow rate: 150 ml/min; 220 nm; RT1:4.2; RT2:5.31] delivered the desired product as isomer 1 (330 mg, 47.1%) a white solid and isomer 2 (335 mg, 47.9%) a yellow gum.

Step 2. 5-fluoro-1-[4-(4-fluorophenyl)-2-pyrazol-1-yl-cyclopentyl]piperidin-3-amine Compound 9

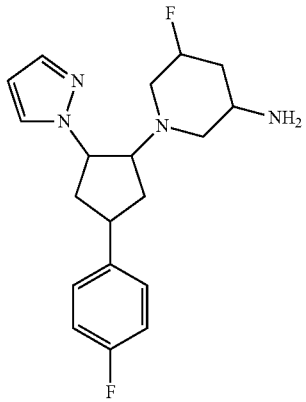 [SMILES: NC1CC(F)CN(C2CC(c3ccc(F)cc3)CC2n2cccn2)C1]

TFA (2.0 mL) was added to tert-butyl ((3R,5S)-5-fluoro-1-((1S,2S,4R)-4-(4-fluorophenyl)-2-(1H-pyrazol-1-yl)cyclopentyl)piperidin-3-yl)carbamate isomer1 (328 mg, 0.73 mmol) in DCM (8 mL). The resulting mixture was stirred at rt for 2 hours. Preparative HPLC [XBridge Prep OBD C18 Column 30×150 mm, 5 μm; Mobile Phase A: Water (0.05% NH₃H₂O), Mobile Phase B: MeCN; Flow rate: 60 ml/min; Gradient: 25% B to 50% B in 7 min; 254/220 nm; Rt: 5.40 min] gave Compound 9 (120 mg, 47.2%, isomer 1) as a white solid. m/z (ESI), [M+H]⁺=347.1; 1H NMR (300 MHz, CD₃OD) δ 7.81 (d, 1H), 7.54 (d, 1H), 7.43-7.25 (m, 2H), 7.12-6.97 (m, 2H), 6.32 (t, 1H), 5.01-4.88 (m, 1H), 4.75-4.64 (m, 1H), 3.67-3.45 (m, 2H), 3.17-2.83 (m, 3H), 2.49-2.15 (m, 4H), 2.14-1.74 (m, 3H), 1.43 (dddd, 1H). 19F NMR (282 MHz, CD₃OD) δ −119.15, −183.33.

Compound 10

Step 1. tert-butyl N-[(3R,5R)-5-fluoro-1-[(1R,2R,4S)-4-(4-fluorophenyl)-2-(1,2,4-triazol-1-yl)cyclopentyl]-3-piperidyl]carbamate and tert-butyl N-[(3R,5R)-5-fluoro-1-[(1S,2S,4R)-4-(4-fluorophenyl)-2-(1,2,4-triazol-1-yl)cyclopentyl]-3-piperidyl] carbamate

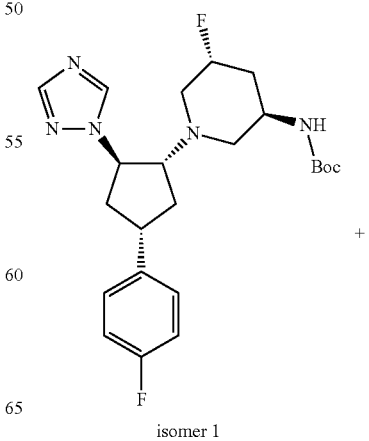

isomer 1

+

39
-continued

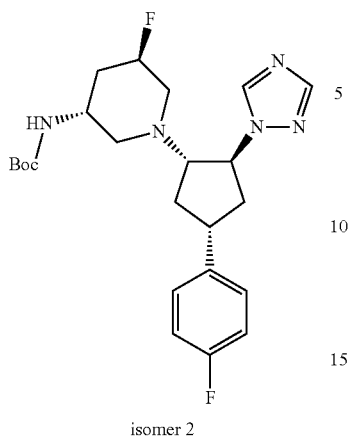

isomer 2

A 0° C. solution of 1:1 mixture of tert-butyl N-[(3R,5R)-5-fluoro-1-[(1R,2R,4S)-4-(4-fluorophenyl)-2-hydroxy-cyclopentyl]-3-piperidyl]carbamate and tert-butyl N-[(3R,5R)-5-fluoro-1-[(1S,2S,4R)-4-(4-fluorophenyl)-2-hydroxy-cyclopentyl]-3-piperidyl]carbamate (F2b) (12 g, 30.27 mmol), 1H-1,2,4-triazole (3.14 g, 45.40 mmol) and PPh$_a$ (11.91 g, 45.40 mmol) in THF (150 mL) was treated with di-isopropyl azodicarboxylate (9.18 g, 45.40 mmol). After 3 h at 25° C., the solvent was removed under reduced pressure. C18 flash column chromatography of the residue (10 to 28% MeCN in water (with 0.2% TFA)) to give the desired Mitsunobu products (12.00 g, 89%) as a light-yellow oil.

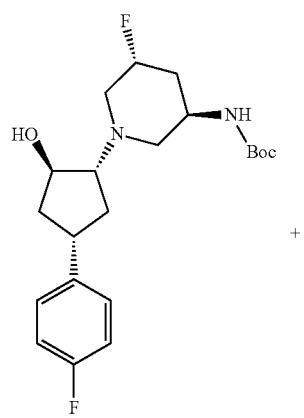

+

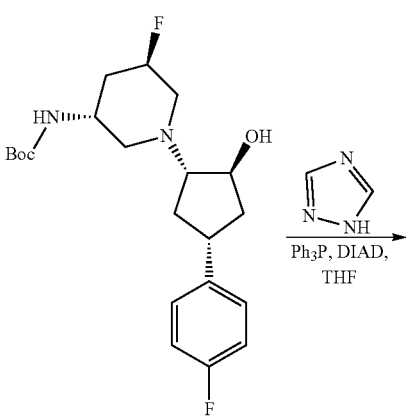

40
-continued

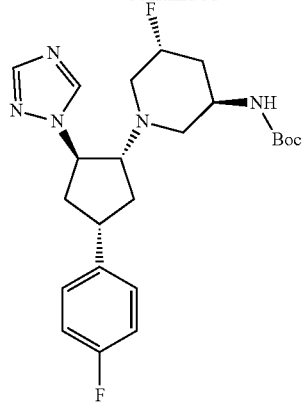

+

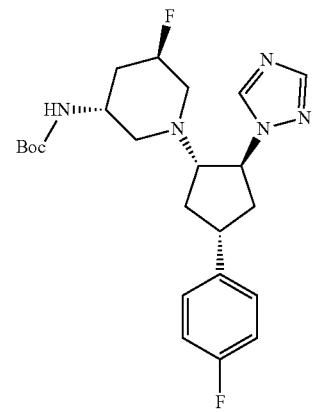

A mixture of the diastereomers from a series of reactions described above (i.e. tert-butyl N-[(3R,5R)-5-fluoro-1-[(1R,2R,4S)-4-(4-fluorophenyl)-2-(1,2,4-triazol-1-yl)cyclopentyl]-3-piperidyl]carbamate and tert-butyl N-[(3R,5R)-5-fluoro-1-[(1S,2S,4R)-4-(4-fluorophenyl)-2-(1,2,4-triazol-1-yl)cyclopentyl]-3-piperidyl]carbamate) (694 g, 1.55 mol) was separated by Chiral-SFC [Column: CelluCoat, 50×250 mm, 10 µm; Mobile Phase: 17% MeOH in CO$_2$; Flow rate: 450 ml/min; 260 nm; RT1:2.25 min; RT2:2.88 min] to give tert-butyl N-[(3R,5R)-5-fluoro-1-[(1R,2R,4S)-4-(4-fluorophenyl)-2-(1,2,4-triazol-1-yl)cyclopentyl]-3-piperidyl]carbamate (isomer 1) (335.3 g, 48.3%, 99.8% ee/de) as a white solid. 1H NMR (400 MHz, CDCl$_3$) δ 1.44 (9H, s), 1.73-1.93 (3H, m), 2.17-2.44 (4H, m), 2.55 (1H, s), 2.62-2.9 (2H, m), 3.54 (2H, dt), 3.94 (1H, s), 4.79 (3H, ddd), 6.9-7.07 (2H, m), 7.20 (2H, ddd), 7.97 (1H, s), 8.19 (1H, s); LCMS: m/z (ES+), [M+H]+=448; and tert-butyl N-[(3R,5R)-5-fluoro-1-[(1S,2S,4R)-4-(4-fluorophenyl)-2-(1,2,4-triazol-1-yl)cyclopentyl]-3-piperidyl]carbamate (isomer 2) (343 g, 49.4%, 98.1% ee/de) as a white solid. 1H NMR (400 MHz, CDCl$_3$) δ 1.45 (9H, s), 1.74 (3H, q), 2.18-2.46 (4H, m), 2.56-2.82 (3H, m), 3.53 (2H, dtd), 3.97 (1H, s), 4.80 (3H, ddd), 6.93-7.06 (2H, m), 7.20 (2H, ddd), 7.97 (1H, s), 8.16 (1H, s); LCMS: m/z (ES+), [M+H]+=448.

Step 2. (3R,5R)-5-fluoro-1-[(1R,2R,4S)-4-(4-fluorophenyl)-2-(1,2,4-triazol-1-yl)cyclopentyl]piperidin-3-amine Compound 10

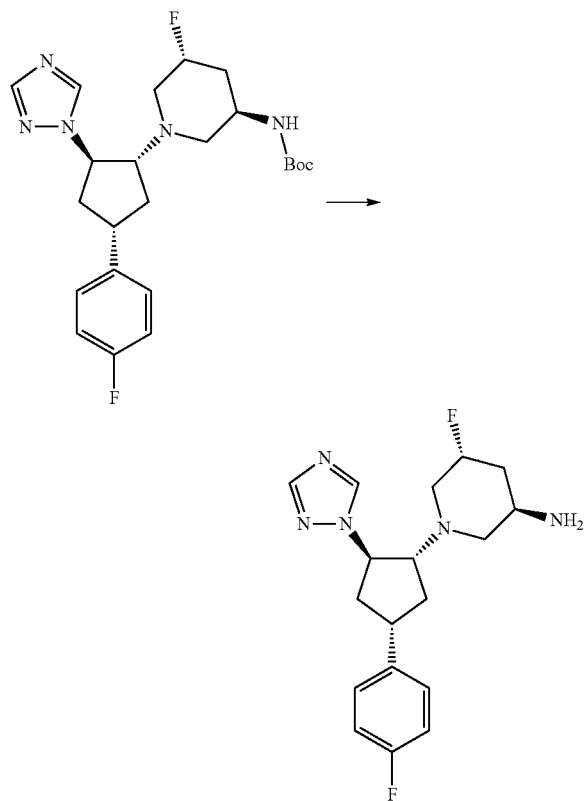

Boc-deprotection of tert-butyl N-[(3R,5R)-5-fluoro-1-[(1R,2R,4S)-4-(4-fluorophenyl)-2-(1,2,4-triazol-1-yl)cyclopentyl]-3-piperidyl]carbamate isomer 1 (335 g, 0.75 mol) in isopropanol (1.32 L) was carried out under a nitrogen atmosphere, by adding 3.8 M HCl (aq. 1.18 L, 4.5 mol, 6 eq.) at 20° C., then stirring for 15 h at 50° C. The solvents were removed by vacuum and the residue was diluted with DCM (2.5 L), cooled to ca 10° C. and basified to pH 10-11 with 1.5 M $Na_2CO_3$ (ca 2.5 L needed). The organic layer was separated and the aqueous layer was back-extracted with DCM (1.5 L). The combined organic layers were washed with water (1 L) and dried over $Na_2SO_4$. After polish filtration and evaporation of the solvents 260 g of the (3R,5R)-5-fluoro-1-[(1R,2R,4S)-4-(4-fluorophenyl)-2-(1,2,4-triazol-1-yl)cyclopentyl]piperidin-3-amine was obtained as a white amorphous solid (quantitative yield).

Crystallisation to the desired polymorph, referred to above as Compound 10 Form A or Form A, was performed by adding isopropyl acetate (450 mL) to (3R,5R)-5-fluoro-1-[(1R,2R,4S)-4-(4-fluorophenyl)-2-(1,2,4-triazol-1-yl)cyclopentyl]piperidin-3-amine (280 g, 804 mmol) and heating at 70° C. during 30 minutes (until a homogeneous solution was produced). Heptane (450 mL) was then added in a portionwise manner during 20-30 minutes. After stirring for 30 minutes at 70° C. the temperature was decreased stepwise and stirring continued at ca 20° C. overnight (ca 16 h). For XRPD analysis, the resultant solid Form A was isolated by filtration and then washed with cold heptane (150-200 ml). Drying overnight at 40° C. in vacuo yielded 269 g (96.4% yield, >99.9% ee/de) of Compound 10 Form A as a white crystalline solid. 1H NMR (500 MHz, DMSO-$d_6$) δ 1.31 (1H, m), 1.71 (1H, q), 1.85 (2H, m), 1.91 (1H, d), 2.20 (2H, d), 2.24 (2H, m), 2.33 (1H, dd), 2.81 (1H, d), 2.84 (1H, s), 2.89 (1H, s), 3.38 (1H, m), 3.49 (1H, m), 4.78 (1H, d), 5.01 (1H, s), 7.12 (2H, t), 7.37 (2H, dd), 8.01 (1H, s), 8.67 (1H, s); LCMS: m/z (ES+), [M+H]+=348. For crystallography data see above at e.g. Table 1 and FIG. 1.

Compound 11

Step 1. tert-butyl (3R,5R)-5-fluoro-1-(4-(4-fluorophenyl)-2-(2H-tetrazol-2-yl) cyclopentyl) piperidin-3-yl carbamate Di-tert-butyl azodicarboxylate (437 mg, 1.90 mmol) was added to F2b (376 mg, 0.95 mmol), 2H-tetrazole (100 mg, 1.42 mmol) and $Ph_3P$ (497 mg, 1.90 mmol) in DCM (30 mL) at 0° C. under nitrogen. The resulting mixture was stirred at 25° C. for 8 hours and then the solvent was removed under reduced pressure. The crude product was purified by flash C18-flash chromatography (0 to 40% MeCN in water). Pure fractions were evaporated to dryness to afford trans tert-butyl (3R, 5R)-5-fluoro-1-(4-(4-fluorophenyl)-2-(2H-tetrazol-2-yl)cyclopentyl)piperidin-3-ylcarbamate (253 mg, 59.5%) as a white solid. LCMS: m/z (ESI), [M+H]+= 449.5. $^1$H NMR (400 MHz, $CD_3OD$) δ 8.78 (s, 1H), 7.38 (dd, 2H), 7.06 (t, 2H), 5.68-5.55 (m, 1H), 4.74 (s, 1H), 3.85 (s, 1H), 3.73-3.57 (m, 2H), 3.10-2.92 (m, 2H), 2.51-2.35 (m, 4H), 2.12-1.86 (m, 4H), 1.45 (d, 9H). The crude product was purified by preparative chiral-HPLC on a Chiralpak IA column, eluting isocratically with 20% EtOH in Hexanes (0.1% DEA) as eluent. The fractions containing the desired compound were evaporated to dryness to afford, isomer 1 (114 mg, 45.1%, isomer 1, 100% ee) and fraction 2 (18.00 mg, 7.11%, mixture (isomer 2 and isomer 3) and isomer 4 (89 mg, 35.2%, 95.5% ee) as a white solid.

Step 2. 5-fluoro-1-[4-(4-fluorophenyl)-2-(tetrazol-2-yl)cyclopentyl]piperidin-3-amine Compound 11

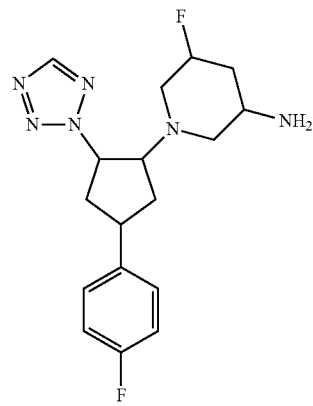 [SMILES: NC1CC(F)CN(C2CC(c3ccc(F)cc3)CC2n2ncnn2)C1]

TFA (1 mL, 12.98 mmol) was added to isomer 1 of the foregoing (112 mg, 0.25 mmol) in DCM (4 ml) at 25° C. to remove the Boc group. The resulting mixture was stirred at 25° C. for 2 hours and then the solvent was removed under reduced pressure. The crude product was purified by preparative HPLC [(XBridge Prep C18 OBD column, 5 μm silica, 19 mm diameter, 150 mm length), using decreasingly polar mixtures of water (containing 0.05% NH₃H₂O) and MeCN as eluents]. Fractions containing the desired compound were evaporated to dryness to afford Compound 11 (40.0 mg, 46.0%, isomer 1) as a white solid. This proved to be the most potent isomer. LCMS: m/z (ESI), [M+H]⁺= 349.5. DSC: temp: 272.86° C.; 1H NMR (300 MHz, CD₃OD) δ 8.79 (s, 1H), 7.52-7.31 (m, 2H), 7.18-6.98 (m, 2H), 5.59 (ddd, 1H), 4.75 (s, 1H), 3.66 (ddt, 2H), 3.20-2.94 (m, 3H), 2.59-2.26 (m, 4H), 2.28-1.86 (m, 3H), 1.62-1.23 (m, 1H). 19F NMR (300 MHz, CD₃OD) δ −118.88-118.76 (1F, s), 184.37-183.48 (1F, s).

Compound 12

Step 1. tert-butyl (3R)-1-(4-(4-fluorophenyl)-2-(2H-tetrazol-2-yl)cyclopentyl)piperidin-3-yl carbamate Di-tert-butyl (E)-diazene-1,2-dicarboxylate (122 mg, 0.53 mmol) was added to F2a (200 mg, 0.53 mmol), 2H-tetrazole (37.0 mg, 0.53 mmol) and triphenylphosphine (139 mg, 0.53 mmol) in DCM (10 ml) at 0° C. over a period of 5 minutes under nitrogen. The resulting mixture was stirred at rt for 15 hours. The solvent was removed under reduced pressure. Alumina flash column chromatography (0 to 70% MeCN in water) gave a white solid (155 mg, 68%) (LCMS: m/z (ESI), [M+H]⁺=431.15; TFA, HPLC Rt=0.729 min). Preparative chiral-HPLC [(Column: CHIRAL ART Cellulose-SB, 2×25 cm, 5 μm; Mobile Phase A: Hexanes (0.1% TFA), Mobile Phase B: EtOH; Flow rate: 20 mL/min; Gradient: A:B=85:15 in 15 min; 254/220 nm; RT1:11.2; RT2:13.32] gave tert-butyl (3R)-1-(4-(4-fluorophenyl)-2-(2H-tetrazol-2-yl)cyclopentyl)piperidin-3-ylcarbamate isomer 1 (70.0 mg, 45.1%, 100% ee) as a colourless oil and isomer 2 (70.0 mg, 45.1%, 100% ee) as a colourless oil.

Step 2. 1-[4-(4-fluorophenyl)-2-(tetrazol-2-yl)cyclopentyl]piperidin-3-amine Compound 12

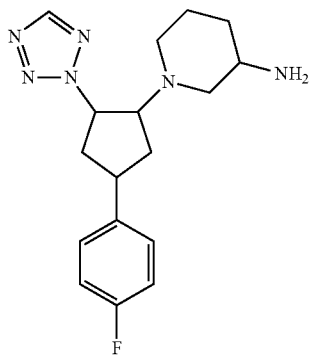 [SMILES: NC1CCCN(C2CC(c3ccc(F)cc3)CC2n2ncnn2)C1]

TFA (96 mg, 0.98 mmol) was added to tert-butyl (3R)-1-(4-(4-fluorophenyl)-2-(2H-tetrazol-2-yl)cyclopentyl)piperidin-3-ylcarbamate isomer 1 (70 mg, 0.16 mmol) in DCM (5 ml) at rt. After stirring for 1 hour at rt, the solvent was removed under reduced pressure. The crude product was purified by preparative HPLC [(Column: XBridge Prep OBD C18 Column 19×250 mm, 5 μm; Mobile Phase A: Water (0.05% aq. NH₃), Mobile Phase B: MeCN; Flow rate: 20 ml/min; Gradient: 36% B to 46% B in 7 min; 220,254 nm; Rt: 5.79 min to give Compound 12 (25.00 mg, 46.5%) as a white solid. LCMS: m/z (ESI), [M+H]⁺=331.5; TFA, HPLC Rt=1.129 min; 1H NMR (300 MHz, CD₃OD) δ 1.17 (1H, dtd), 1.50-1.64 (1H, m), 1.73 (1H, ddd), 1.83-2.19 (4H, m), 2.34-2.56 (3H, m), 2.77-3.02 (3H, m), 3.50-3.80 (2H, m), 5.59 (1H, ddd), 7.00-7.13 (2H, m), 7.31-7.43 (2H, m), 8.77 (1H, s). 19F NMR (282 MHz, CD₃OD) δ −118.65, −76.86. DSC: temp: 281.89° C.

Compound 13

Step 1. tert-butyl (3R)-1-(2-(3-cyano-1H-1,2,4-triazol-1-yl)-4-(4-fluorophenyl)cyclopentyl) piperidin-3-yl carbamate Di-tert-butyl azodicarboxylate (426 mg, 1.85 mmol) was added to F2a (350 mg, 0.92 mmol), 1H-1,2,4-triazole-3-carbonitrile (104 mg, 1.11 mmol) and Ph₃P (485 mg, 1.85 mmol) in DCM (10 ml) at 25° C. under nitrogen then stirred at 25° C. for 3 hours. After standard work up C18 flash column chromatography, (0 to 40% MeCN in water (containing 0.3% NH₃OH)) gave a white solid (350 mg). Preparative TLC (petroleum ether:EtOAc=2:1), afforded fraction 1 (110 mg, 26%) & fraction 2 (230 mg, 55%) as white solids. Fraction 1 was further separated by preparative chiral-HPLC on a Chiralpak IA column, eluting isocratically with Hexane in EtOH as eluent to give isomer 1 tert-butyl (3R)-1-(2-(3-cyano-1H-1,2,4-triazol-1-yl)-4-(4-fluorophenyl)cyclopentyl)piperidin-3-ylcarbamate (31.0 mg, 28%, 100% ee) and isomer 2 (37.0 mg, 34%, 100% ee) as a white solid.

Step 2. 1-[2-(3-amino-1-piperidyl)-4-(4-fluorophenyl)cyclopentyl]-1,2,4-triazole-3-carbonitrile Compound 13

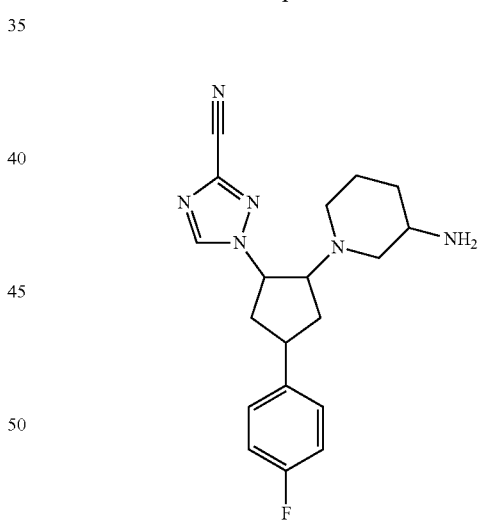

TFA (1.0 mL) was added to isomer 1 (31 mg, 0.07 mmol) obtained in step 1 in DCM (5 mL) at 25° C. The resulting mixture was stirred at 25° C. for 2 h, concentrated and then purified by preparative HPLC (XBridge Prep C18 OBD column, 5μ silica, 19 mm diameter, 150 mm length), using decreasingly polar mixtures of water (containing 0.05% TFA) and MeCN as eluents to give Compound 13 (24.3 mg, 46%), as a white solid; LCMS: m/z (ESI) [M+H]⁺=355.5; 1H NMR (300 MHz, CD₃OD) δ 8.27 (s, 1H), 7.35 (dd, 2H), 7.06 (t, 2H), 5.44 (q, 1H), 4.04 (dt, 1H), 3.72-3.37 (m, 3H), 3.03-2.87 (m, 1H), 2.82-2.67 (m, 2H), 2.50 (ddd, 3H), 2.13-1.87 (m, 3H), 1.85-1.48 (m, 2H).

Compound 14 and Compound 15

Step 1. tert-butyl (3R)-1-(4-(4-fluoro-3-methoxyphenyl)-2-hydroxycyclopentyl)piperidin-3-ylcarbamate To a solution of F4 (100 mg, 1.0 eq.) in 3 mL anhydrous ethanol was added (R)-tert-butyl piperidin-3-ylcarbamate (115 mg, 1.2 eq.) and sodium carbonate (101 mg, 2.0 eq.) in a sealed vial. The suspension was irradiated in microwave at 130° C. for 6 h, then filtered and concentrated. Column chromatography on (silica gel 0 to 3% methanol in DCM) to give tert-butyl (3R)-1-(4-(4-fluoro-3-methoxyphenyl)-2-hydroxycyclopentyl)piperidin-3-ylcarbamate (140 mg, 71% yield) as a colourless solid. 1H NMR (CDCl$_3$ 400 MHz) δ 6.99 (dd, 1H), 3.86 (dd, 1H), 6.75-6.71 (m, 1H), 4.92 (br. s, 1H), 4.27-4.21 (m, 1H), 3.89 (s, 3H), 3.75 (br. s, 1H), 3.10-3.06 (m, 2H), 2.88-2.75 (m, 2H), 2.53 (br. s, 2H), 2.41-2.35 (m, 2H), 2.15-2.05 (m, 1H), 1.90-1.66 (m, 6H), 1.40 (d, 9H).

Step 2. tert-butyl (3R)-1-(2-(4-cyanophenoxy)-4-(4-fluoro-3-methoxyphenyl) cyclopentyl) piperidin-3-yl carbamate A solution of tert-butyl (3R)-1-(2-(4-cyanophenoxy)-4-(4-fluoro-3-methoxyphenyl) cyclopentyl) piperidin-3-yl carbamate (140 mg, 1.0 eq.) in 3 mL anhydrous THF was stirred and treated with NaH (35 mg, 2.5 eq.). After 0.5 h, 4-fluorobenzonitrile (50 mg, 1.2 eq.) was added to the reaction which was then stirred for 18 h at rt, and then at 45° C. for 18 h. The reaction mixture was then poured into 5 mL saturated solution of NH$_4$Cl, extracted with EtOAc (5 mL×3), dried and purified by column chromatography on silica gel (DCM/MeOH=20/1) to afford the desired 4-cyanophenoxy compound (80 mg, 46% yield). Purification using Waters SFC 350 Preparative System [column: AS (250 mm*30 mm*5 μm), condition: 25% IPA in aq. NH$_3$ 60 mL/min] gave tert-butyl (3R)-1-(2-(4-cyanophenoxy)-4-(4-fluoro-3-methoxyphenyl) cyclopentyl) piperidin-3-ylcarbamate isomer 1 (30 mg, 37% yield) and isomer 2 (35 mg, 43% yield); Isomer 1 shows LCMS Rt=0.892 min in 5-95AB_1.5 min chromatography, MS (ESI) m/z=510.3 [M+H]$^+$. 1H NMR (CDCl$_3$ 400 MHz) δ 7.84 (dd, 1H), 7.60 (dd, 2H) 7.16-7.11 (m, 1H), 6.99-6.96 (m, 1H), 6.84-6.82 (m, 1H), 6.77-6.73 (m, 1H), 4.79-4.77 (m, 2H), 3.88 (s, 3H), 3.73 (br. s, 1H), 3.25-3.19 (m, 2H), 2.69-2.63 (m, 2H), 2.47-2.19 (m, 4H), 2.04-1.95 (m, 1H), 1.88-1.82 (m, 2H), 1.68-1.64 (m, 3H), 1.43 (d, 9H). LCMS: m/z (ESI), [M+H]$^+$=510.

Step 3. 4-[2-(3-amino-1-piperidyl)-4-(4-fluoro-3-hydroxy-phenyl)cyclopentoxy]benzonitrile (Compound 14) and 4-[2-(3-amino-1-piperidyl)-4-(4-fluoro-3-methoxy-phenyl)cyclopentoxy]benzonitrile (Compound 15)

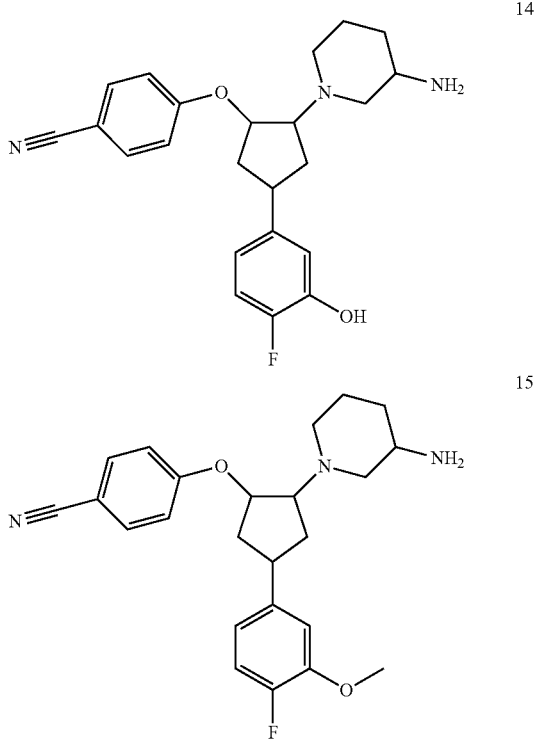

To a solution of isomer 1 of the carbamate described above (30 mg) in DCM (2 mL) was added BBr$_3$ (0.5 ml) at −78° C. The mixture was stirred at −78° C. for 1 h. The mixture was poured into aq. NH$_4$Cl (20 mL), adjusted pH=10 by using aq NaHCO$_3$, then extracted with DCM (2×20 mL). The organic layers were dried over sodium sulfate, concentrated and purified by prep-HPLC [(method: column: Durashell C18 150*25 mm*5 μm, gradient: 43-73% B (A=water/0.05% ammonia, B=acetonitrile), flow rate: 25 ml/min)] to give Compound 14 (1.3 mg, 5.6% yield) and Compound 15 (1.0 mg, 4.1% yield).

Compound 14

LCMS: m/z (ESI), [M+H]$^+$=396. 1H NMR (CD$_3$OD 400 MHz) δ 7.65 (d, 2H), 7.15 (d, 2H), 6.93 (dd, 1H), 6.82 (d, 1H), 6.70-6.64 (m, 1H), 5.00-4.98 (m, 1H), 3.26-3.18 (m, 2H), 3.05-2.95 (m, 1H), 2.93-2.63 (m, 3H), 2.30-2.14 (m, 2H), 2.10-1.95 (m, 2H), 1.90-1.65 (m, 3H), 1.63-1.49 (m, 1H), 1.24-1.10 (m, 1H).

Compound 15

LCMS: m/z (ESI), [M+H]$^+$=410. 1H NMR (CD$_3$OD 400 MHz) δ 7.66 (d, 2H), 7.15 (d, 2H), 7.00-6.96 (m, 2H), 6.83-6.75 (m, 1H), 4.72-4.65 (m, 1H), 3.84 (s, 3H), 3.42-3.35 (m, 1H), 3.30-3.23 (m, 1H), 3.05-2.95 (m, 1H), 2.90-2.65 (m, 3H), 2.35-2.15 (m, 2H), 2.14-1.95 (m, 2H), 1.91-1.68 (m, 3H), 1.62-1.49 (m, 1H), 1.25-1.13 (m, 1H).

Compound 16

Step 1. tert-butyl (3R)-1-(2-(2-chloro-4-cyanophenoxy)-4-(3-fluorophenyl)cyclopentyl)piperidin-3-ylcarbamate To a solution of F3 (580 mg) in THF (8 mL) was added NaH (184 mg, 3.0 eq) at 0° C. in portions. After stirred at the same temperature for 30 min, 3-chloro-4-fluorobenzonitrile (285 mg, 1.2 eq) dissolved in THF (2 ml) was added in portions. The reaction mixture was stirred at rt overnight, then quenched with aqueous NH₄Cl (20 ml), diluted with water (50 ml), extracted with ethyl acetate (50 ml×3), dried over Na₂SO₄. The combined organic layer was concentrated to give the desired ether (920 mg) as yellow oil. LCMS: m/z (ESI), [M+H]$^+$=514.

Step 2. 4-[2-(3-amino-1-piperidyl)-4-(3-fluorophenyl)cyclopentoxy]-3-chloro-benzonitrile Compound 16

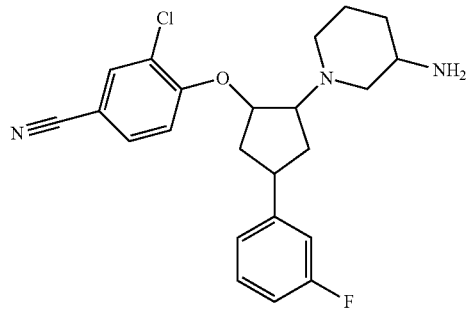 [SMILES: N#Cc1ccc(OC2CC(c3cccc(F)c3)CC2N2CCCC(N)C2)c(Cl)c1]

A solution of the above Boc protected compound (920 mg) in HCl/dioxane (10 ml) was stirred at rt for 2 h then concentrated to give a solid. The solid was washed with ethyl acetate (3×20 mL), then dried to give a residue (350 mg, 47%), which was separated by Waters SFC 350 Preparative System [column: AD (250×30 mm, 5 μm), condition: 30% ethanol/ammonia flow rate: 60 mL/min] to give isomer 1 Compound 16 (95.7 mg) and a second, isomer 2, of the same compound (125.1 mg).

Isomer 1 (Compound 16): LCMS: m/z (ESI) [M+H]$^+$=414. Most potent isomer: 1H NMR (CD₃OD 400 MHz) δ 7.81-7.80 (1H, m), 7.68-7.65 (1H, m), 7.31-7.28 (2H, m), 7.15-6.94 (3H, m), 5.06-4.92 (1H, m), 3.40-3.25 (2H, m), 3.05-2.95 (1H, m), 2.92-2.72 (2H, m), 2.45-2.36 (1H, m), 2.32-2.00 (4H, m), 1.90-1.51 (4H, m), 1.24-1.19 (1H, m).

Isomer 2: LCMS: m/z (ESI), [M+H]$^+$=414. 1H NMR (CD₃OD 400 MHz) δ 7.83-7.82 (1H, m), 7.68-7.67 (1H, m), 7.32-7.27 (3H, m), 7.05-7.01 (2H, m), 5.05-4.97 (1H, m), 3.43-3.35 (2H, m), 3.10-2.95 (1H, m), 2.95-2.75 (2H, m), 2.47-2.39 (1H, m), 2.35-2.05 (4H, m), 1.95-1.56 (4H, m), 1.28-1.22 (1H, m).

Compound 17

Step 1. tert-butyl 1-(2-(4-cyanophenoxy)-4-(4-fluorophenyl)cyclopentyl)-4,4-difluoropiperidin-3-ylcarbamate To a solution of tert-butyl 4,4-difluoro-1-(4-(4-fluorophenyl)-2-hydroxycyclopentyl)piperidin-3-ylcarbamate F2c (250 mg, 1.0 eq.), 4-hydroxybenzonitrile (86 mg, 1.2 eq.) and Ph₃P (470 mg, 3.0 eq.) in anhydrous THF (10 mL) was added DIAD (485 mg, 4.0 eq.) at 0° C. under nitrogen dropwise. The resulting mixture was stirred at 14-22° C. for 20 h. After standard work up, flash chromatography (petroleum ether/EA=90/10 to 80/20) gave the mixture of isomeric products (220 mg, 71% yield) as yellow thick oil. Separation by Waters SFC 350 Preparative System (column: OJ 250 mm*30 mm*5 μm, condition: base-methanol, flow rate: 60 ml/min) gave pure isomer 1 (20 mg, peak1) and isomer 2 (15 mg, peak2) and a mixture of two isomers (50 mg, peak 3+4) which was further separated by Waters SFC 350 Preparative System (column: IC 250 mm*30 mm*10 um, condition: base-methanol, flow rate: 70 ml/min) to give isomer 3 (15 mg, peak1 in second separation) and isomer 4 (10 mg, peak2 in second separation). All isomers were obtained as colourless oils. LCMS for isomer 1: m/z (ESI) [M+H]$^+$=516.

Step 2. 4-[2-(3-amino-4,4-difluoro-1-piperidyl)-4-(4-fluorophenyl)cyclopentoxy]benzonitrile Compound 17

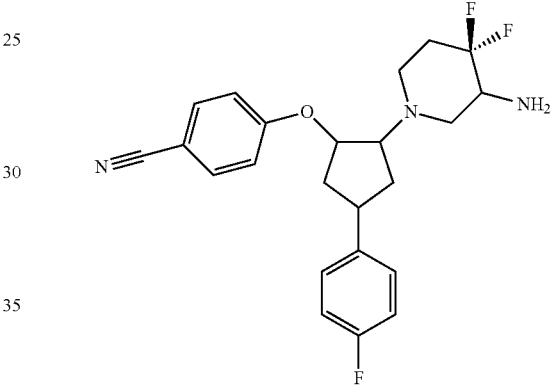

To a solution of the above isomer 1 (20 mg, 1.0 eq.) in anhydrous dichloromethane (5 mL) was added TFA (1 mL). The resulting mixture was stirred at 16-23° C. for 1 h. The mixture was poured into saturated NaHCO₃ solution (50 mL), extracted with DCM (30 mL×3), dried over anhydrous sodium sulfate, concentrated. The residue was purified by pre-HPLC (column: Durashell 150*25 mm*5 μm, gradient: 70%-95% B (A=0.05% ammonia/water, B=methanol, flow rate: 25 ml/min) to give Compound 17 (2.9 mg, 18% yield) as white solid after lyophilisation. LCMS: m/z (ESI), [M+H]$^+$=416. 1H NMR (CD₃OD 400 MHz) δ 7.68 (d, 2H), 7.33-7.29 (dd, 2H), 7.12 (d, 2H), 7.03 (t, 2H), 4.90-4.85 (m, 1H), 3.35-3.32 (m, 1H), 3.30-3.28 (m, 1H), 3.15-3.05 (m, 1H), 2.98-2.87 (m, 1H), 2.82-2.71 (m, 1H), 2.66-2.55 (m, 1H), 2.52-2.32 (m, 2H), 2.27-2.08 (m, 3H), 2.07-1.92 (m, 1H), 1.81-1.75 (m, 1H).

Compound 18

Step 1. tert-butyl (3R)-1-(2-(4-cyanophenoxy)-4-(4-fluorophenyl) cyclopentyl)-5,5-difluoropiperidin-3-yl carbamate To a mixture of PPh₃ (569 mg, 3.0 eq.) and 4-hydroxybenzonitrile (129 mg, 1.5 eq.) was added solution of F2d (290 mg, 1.0 eq.) and DIAD (439 mg, 3.0 eq.) in 3 mL anhydrous THF under nitrogen. The yellow solution was stirred at 17-27° C. for 18 h. The solution was concentrated and purified by column on silica gel (petroleum ether/ EtOAc, 0 to 20% EA), washed with saturated solution of potassium carbonate (3×10 ml) and concentrated to afford tert-butyl (3R)-1-(2-(4-cyanophenoxy)-4-(4-fluorophenyl) cyclopentyl)-5,5-difluoropiperidin-3-ylcarbamate (328 mg, 88% yield) as a white solid. LCMS: m/z (ESI), [M+H]⁺= 516.

Step 2. 4-[2-(5-amino-3,3-difluoro-1-piperidyl)-4-(4-fluorophenyl)cyclopentoxy]benzonitrile Compound 18

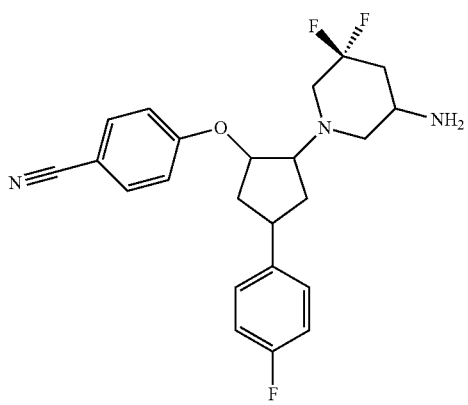

To a solution of the above Boc-protected compound (328 mg, 1.0 eq.) in 5 mL DCM was added 2 mL TFA. The solution was stirred at rt for 1 h then concentrated. The residue was diluted with aq. HCl and extracted with petroleum ether/EtOAc (1:1) (20 mL×3) to remove impurities. The aqueous layer was basified with sodium bicarbonate and extracted with dichloromethane (10 mL×3). The combined organic layers were dried over sodium sulfate, filtered and concentrated to afford a yellow solid (50 mg, yield 19%) which was separated by Berger MG-Il SFC Preparative System [ChiralPak AD 250×30 mm I.D., 5 um; Mobile phase: CO₂/MeOH (0.1% aq. NH₃)=70/30 at 60 ml/min)] to afford Compound 18 (5.2 mg, 10%) as a white solid. A second isomer, data not reported here, was also isolated.

Compound 18 Showed

LCMS: m/z (ESI), [M+H]⁺=416. 1H NMR (CD₃OD 400 MHz) δ 7.68 (d, 2H), 7.32 (dd, 2H), 7.15 (d, 2H), 7.04 (t, 2H), 4.89-4.84 (m, 1H), 3.38-3.36 (m, 1H), 3.18 (br. s, 1H), 2.96-2.92 (m, 2H), 2.79-2.73 (m, 1H), 2.39-2.15 (m, 6H), 1.84-1.78 (m, 2H).

Compound 19

Step 1. tert-butyl (3R)-1-(2-(4-cyano-3-fluorophenoxy)-4-(4-fluorophenyl) cyclopentyl) piperidin-3-yl carbamate To a solution of F2a (200 mg), 2-fluoro-4-hydroxybenzonitrile (108 mg, 1.5 eq) and PPh₃ (272 mg, 2.0 eq) in THF (4 ml) was added DIAD (180 mg, 2.0 eq) in THF (1 mL) at 0° C. The mixture was stirred at 25° C. for 3 days. The mixture was diluted with water (20 mL), extracted with EA (2×20 ml). The organic layers were dried over sodium, concentrated and purified by chromatography column on silica gel (petroleum ether/EA=5/1) to give the product (200 mg, 76% yield), which was separated by Waters SFC 350 Preparative System [column: AD (300 mm*50 mm, 10 μm), condition: 35% IPA+aq. NH₃ 80 ml/min] to give isomer 1 (77 mg, 38% yield, Rt=8.21 min) and isomer 2 (76 mg, 38% yield, Rt=9.64 min). LCMS for both isomers, m/z (ESI), [M+Na]⁺=520.

Step 2. 4-[2-(3-amino-1-piperidyl)-4-(4-fluorophenyl)cyclopentoxy]-2-fluoro-benzonitrile Compound 19

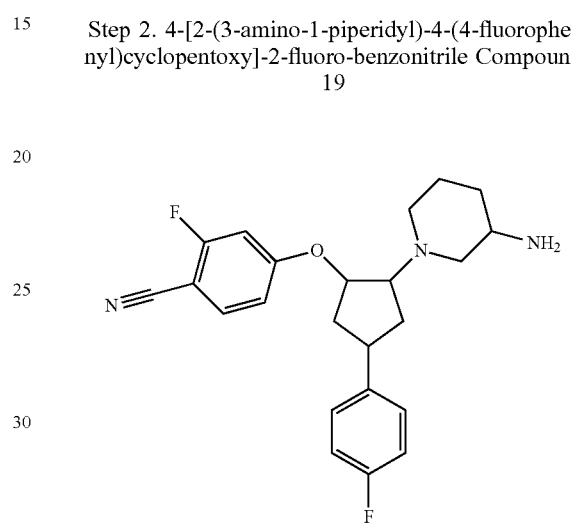

A solution of isomer 1 obtained directly above (77 mg) in DCM (2 mL) and TFA (1 mL) was stirred at 27° C. for 30 min. The mixture was concentrated and purified by pre-HPLC (method: column: Waters Xbridge C18 150*20 mm*5 μm, gradient: 65-95% B (A=water/0.05% ammonia, B=methanol), flow rate: 25 mL/min) to give Compound 19 (13.5 mg, 20% yield). LCMS: m/z (ESI), [M+H]⁺=398. 1H NMR (CD₃OD 400 MHz) δ 7.65 (t, 1H), 7.32-7.25 (m, 2H), 7.07-6.98 (m, 3H), 6.94 (dd, 1H), 4.84-4.80 (m, 1H), 3.30-3.24 (m, 1H), 3.20-3.14 (m, 1H), 3.03-2.94 (m, 1H), 2.89-2.73 (m, 2H), 2.38-2.32 (m, 1H), 2.25-2.07 (m, 3H), 1.99 (t, 1H), 1.92-1.84 (m, 1H), 1.81-1.66 (m, 2H), 1.64-1.48 (m, 1H), 1.21-1.11 (m, 1H).

Compound 20

Step 1. tert-butyl (3R)-1-(2-(2-cyanophenoxy)-4-phenylcyclopentyl) piperidin-3-yl carbamate To a stirred solution of F1 (400 mg) in DMF (3 mL) was added NaH (133 mg, 3.0 eq) in portions at 0° C., then after 30 min, 2-fluorobenzonitrile (148 mg, 1.1 eq) dissolved in DMF (2 mL) was introduced dropwise and the reaction was stirred at rt overnight. After standard work up the reaction was purified by chromatography column (petroleum ether/EtOAc 1:1) to give crude tert-butyl (3R)-1-(2-(2-cyanophenoxy)-4-phenylcyclopentyl)piperidin-3-ylcarbamate (210 mg, 41% yield). LCMS: m/z (ESI) [M+H]⁺=462.

Step 2. 2-[2-(3-amino-1-piperidyl)-4-phenyl-cyclopentoxy]benzonitrile Compound 20

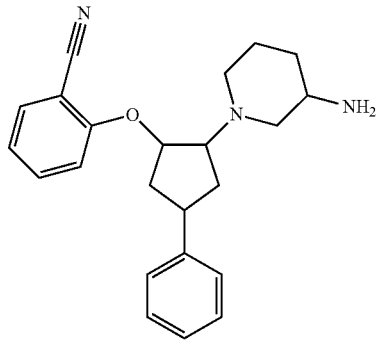 [SMILES: N#Cc1ccccc1OC1CC(c2ccccc2)CC1N1CCCC(N)C1]

To a stirred solution of the product of the preceding experiment (210 mg) in dichloromethane (3 ml) was added HCl/dioxane (2 mL, 4M) at rt. Then the mixture was stirred at rt for 2 h, then extracted with dichloromethane (15 ml×3) and then the aqueous was adjusted to pH 8 by adding saturated solution of NaHCO$_3$. The aqueous layer was extracted with dichloromethane (20 mL×3). The combined organic layers were dried over anhydrous sodium sulfate and concentrated to crude give 2-(2-((R)-3-aminopiperidin-1-yl)-4-phenylcyclopentyloxy)benzonitrile (93 mg, 56% yield). LCMS: m/z (ESI), [M+H]$^+$=362. Purification using Waters SFC 350 Preparative System on this crude product [column: OJ (250 nm*30 nm*5 μm), condition: 30% ethanol/ammonia flow rate: 60 ml/min] gave Compound 20 (23.2 mg, isomer 1) and a second, less potent, isomer (10.5 mg, isomer 2).

Compound 20 (Isomer 1)

LCMS: m/z (ESI), [M+H]$^+$=361. 1H NMR (CD$_3$OD, 400 MHz) δ 7.64-7.60 (m, 2H), 7.30-7.28 (m, 4H), 7.20-7.18 (m, 2H), 7.10-7.06 (m, 1H), 3.38-3.35 (m, 1H), 3.35-3.33 (m, 1H), 2.86-2.81 (m, 3H), 2.40-1.60 (m, 9H), 1.22-1.16 (m, 1H). Isomer 2 LCMS: m/z (ESI), [M+H]$^+$=362. 1H NMR (CD$_3$OD, 400 MHz) δ 7.64-7.60 (m, 2H), 7.30-7.28 (m, 4H), 7.21-7.17 (m, 2H), 7.10-7.07 (m, 1H), 3.37-3.34 (m, 1H), 3.25-3.23 (m, 1H), 3.01-2.81 (m, 3H), 2.41-1.63 (m, 9H), 1.21-1.13 (m, 1H).

Compound 21

1. tert-butyl (3R)-1-(2-(2-chloro-4-cyanophenoxy)-4-phenylcyclopentyl)piperidin-3-ylcarbamate To a mixture of NaH (1.1 g, 2.5 eq.) in anhydrous THF (20 mL) was added a solution of F1 (4.0 g, 1.0 eq., 11.1 mmol) in THF (30 mL) dropwise at 0° C. under nitrogen. After stirring for 0.5 h, a solution of 3-chloro-4-fluorobenzonitrile (2.0 g, 1.2 eq.) in THF (10 mL) was added to the reaction. After stirring at 17-21° C. for another 18 h the mixture was poured into water (200 mL) and extracted with ethyl acetate (3×100 mL). The combined organic layers were dried over sodium sulfate, filtered and concentrated. Column chromatography on silica gel (0 to 30% ethyl acetate in petroleum ether) to afford tert-butyl (3R)-1-(2-(2-chloro-4-cyanophenoxy)-4-phenylcyclopentyl)piperidin-3-ylcarbamate isomer 1 (460 mg, 8.3% yield) and a mixture of other products. Isomer 1 was the least polar product observed from TLC. 1H NMR (CDCl$_3$ 400 MHz) δ 1.45 (9H, s), 1.61-1.85 (4H, m), 2.05-2.46 (4H, m), 2.48 (2H, br. s), 2.73 (1H, br. s), 3.15-3.25 (1H, m), 3.34-3.42 (1H, m), 3.75 (1H, br. s), 4.75 (1H, br. s), 4.85 (1H, br. s), 7.08-7.15 (1H, m), 7.23-7.26 (3H, m), 7.29-7.32 (2H, m), 7.52-7.55 (1H, m), 7.66-7.67 (1H, m).

Step 2. 4-[2-(3-amino-1-piperidyl)-4-phenyl-cyclopentoxy]-3-chloro-benzonitrile Compound 21

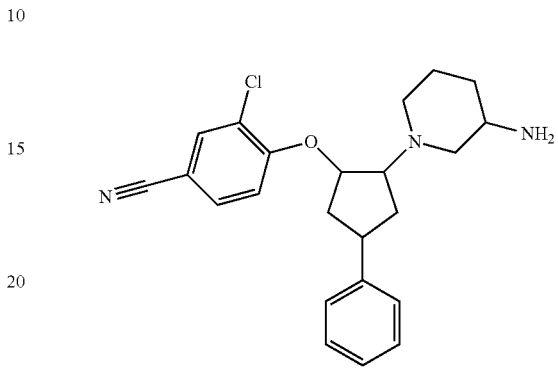

To a solution of isomer 1 (610 mg, 1.0 eq., 1.23 mmol) obtained in the preceding experiment in dichloromethane (5 mL) was added TFA (3 mL). The resulting solution was stirred for 0.5 h at 7-17° C.

The solution was then concentrated, diluted with water (10 mL), basified with ammonia and extracted with DCM (15 mL×3). The combined organic layers were dried over sodium sulfate, filtered and concentrated. The residue was diluted with water then dried (lyophilisation) to afford the final product Compound 21 (348.6 mg, 71% yield) as white solid. LCMS: Rt=1.633 in 4.0 min chromatography, LCMS: m/z (ESI), [M+H]$^+$=396. 1H NMR (CD$_3$OD 400 MHz) δ 1.13-1.26 (1H, m), 1.53-1.66 (1H, m), 1.70-1.77 (1H, m), 1.77-1.85 (1H, m), 1.86-1.94 (1H, m), 2.01-2.07 (1H, m), 2.09-2.17 (1H, m), 2.18-2.29 (2H, m), 2.36-2.45 (1H, m), 2.76-2.83 (1H, m), 2.84-2.92 (1H, m), 2.98-3.05 (1H, m), 3.22-3.39 (2H, m), 4.91-4.95 (1H, m), 7.16-7.22 (1H, m), 7.24-7.33 (5H, m), 7.66 (1H, dd), 7.80 (1H, d).

Compound 22

Step 1. tert-butyl (3R,5R)-1-(2-(6-chloro-4-methylpyridazin-3-yloxy)-4-(4-fluorophenyl) cyclopentyl)-5-fluoropiperidin-3-yl carbamate F2b (950 mg, 2.40 mmol) was added to NaH (115 mg, 4.79 mmol), 3,6-dichloro-4-methylpyridazine (586 mg, 3.59 mmol) in DMF (8 mL) cooled to 0° C. over a period of 5 minutes under nitrogen. The resulting solution was stirred at rt. for 2 hours. The residue was purified by preparative TLC (petroleum ether:EtOAc=2:1) to afford the product as yellow oil (450 mg, 35.9%); LCMS: m/z (ESI), [M+H]$^+$=523; 1H NMR (400 MHz, DMSO-d$_6$) δ 7.89-7.58 (m, 1H), 7.35 (t, 2H), 7.11 (td, 2H), 6.79 (dd, 1H), 5.48 (t, 1H), 4.85 (d, 1H), 3.67 (s, 1H), 3.34 (s, 2H), 3.17 (d, 1H), 2.51 (m, 4H), 2.36-2.08 (m, 4H), 2.13-1.79 (m, 2H), 1.76-1.47 (m, 2H), 1.43-1.26 (m, 21H).

Step 2. tert-butyl (3R,5R)-1-(2-(6-cyano-4-methylpyridazin-3-yloxy)-4-(4-fluorophenyl)cyclopentyl)-5-fluoropiperidin-3-ylcarbamate The 6-chloro-4-methylpyridazin-3-yloxy compound (150 mg, 0.29 mmol) obtained above was added to zinc cyanide (67.3 mg, 0.57 mmol) and 2-di-t-butylphosphino-2',4',6'-tri-i-propyl-1,1'-biphenyl (18.27 mg, 0.04 mmol) in THF (5 mL) under nitrogen. The resulting mixture was stirred at 80° C. for 1 hour then evaporated. The residue was purified by preparative TLC (petroleum ether:EtOAc=2:1), to afford crude product (120 mg, 81%) as a yellow oil. LCMS: m/z (ESI), [M+H]$^+$=514; basic, HPLC Rt=1.371 min. Preparative chiral-HPLC [CHIRALPAK IE, 2 cm×25 cm, 5 μm; Mobile Phase A: Hexanes (0.1% DE)-HPLC, Mobile Phase B: EtOH-HPLC; Flow rate: 20 mL/min; Gradient: A:B=70: 30 in 31 min; 220/254 nm] afforded 8 fractions each with an ee of >98%; Fraction 1 (RT1: 9.37 minutes, 10.00 mg, 6.67%) as a white solid. Isomer 2 (RT2: 12.16 minutes; 15.00 mg, 10.00%) as a white solid. Isomer 3 (RT3: 14.92 minutes; 10.00 mg, 6.67%) as a white solid. Isomer 4 (RT4:17.38 minutes; 10.00 mg, 6.67%) as a white solid. Isomer 5 (RT5: 18.6 minutes; 5.00 mg, 3.33%) as a white solid. Isomer 6 (RT6: 21.8 minutes; 20.00 mg, 13.33%) as a white solid. Isomer 7 (RT7: 23.6 minutes; 15.00 mg, 10.00%) as a white solid. Isomer 8 (RT8: 28 minutes; 10.00 mg, 6.67%) as a white solid.

Step 3. 6-[2-(3-amino-5-fluoro-1-piperidyl)-4-(4-fluorophenyl)cyclopentoxy]-5-methyl-pyridazine-3-carbonitrile Compound 22

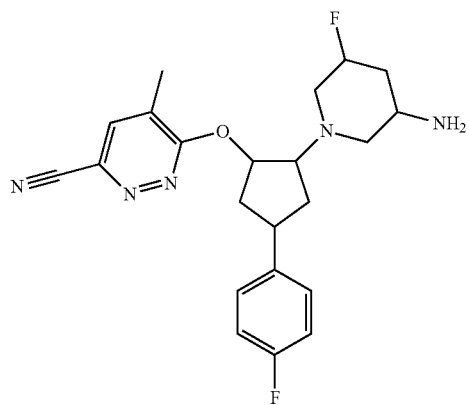 [SMILES: Cc1cc(C#N)nnc1OC1CC(c2ccc(F)cc2)CC1N1CC(N)CC(F)C1]

TFA (0.1 mL, 0.02 mmol) was added to isomer 4 obtained above (8 mg, 0.02 mmol) in DCM (1 mL). The resulting solution was stirred at rt for 30 minutes. The solvent was removed under reduced pressure. The mixture was adjusted to pH=8 with aq. NH$_3$. The crude product was purified by preparative HPLC [(XBridge Prep OBD C18 Column 30×150 mm 5 μm; Mobile Phase A: Water (0.05% aq. NH$_3$), Mobile Phase B: MeCN; Flow rate: 55 ml/min; Gradient: 35% B to 55% B in 7 min; 254/220 nm; Rt: 6.15 mins)]. Fractions containing the desired compound were evaporated to dryness to afford Compound 22 (4.40 mg, 68.3%) as a white solid, which proved the potent isomer. LCMS: m/z (ESI), [M+H]$^+$=414; 1H NMR (300 MHz, CD$_3$OD) δ 7.89 (s, 1H), 7.30-7.30 (m, 2H), 7.07-7.0 (m, 2H), 5.82 (br s, 1H), 5.02 (br s, 1H), 3.58 (br s, 2H), 3.34 (m, 1H), 3.18 (m, 2H), 2.90 (m, 2H), 2.47 (m, 1H), 2.38-2.13 (m, 6H), 1.85 (m, 2H). 19F NMR (282 MHz, CD$_3$OD) δ −118.834, −185.169.

Compound 23

Step 1. ((3R)-1-(2-((4-chloropyridazin-3-yl)oxy)-4-(4-fluorophenyl)cyclopentyl)piperidin-3-yl) carbamate F2 (500 mg, 1.32 mmol) was added to PPh$_3$ (520 mg, 1.98 mmol) and 4-chloropyridazin-3(2H)-one (207 mg, 1.59 mmol) in DCM (8 mL) at 0° C. over a period of 5 minutes under nitrogen. DEAD (0.314 mL, 1.98 mmol) was then introduced in a dropwise manner. The resulting solution was allowed to warm to rt and stirred over 2 hours. The solvent was then removed under reduced pressure and the residue was purified by silica gel flash column chromatography with elution gradient 0 to 50% EtOAc in petroleum ether to afford yellow oil (1000.0 mg, 154%). The crude product was purified by Waters SFC 350 Preparative System [(Column: (R,R)WHELK-01 5/100 Kromasil, 2.11 cm*25 cm (5 μm); Mobile Phase A: CO$_2$: 65%, Mobile Phase B: EtOH-HPLC: 35%; Flow rate: 45 mL/min; 220 nm; RT1:4.06; RT2:4.85)] to afford tert-butyl ((3R)-1-(2-((4-chloropyridazin-3-yl)oxy)-4-(4-fluorophenyl)cyclopentyl)piperidin-3-yl)carbamate isomer 1 (220 mg, 36.7%, 100% ee) as a yellow solid and isomer 2 (240 mg, 40.0%, 96.1% ee) as a yellow solid.

Isomer 1 LCMS: m/z (ESI), [M+H]$^+$=491; 1H NMR (400 MHz, DMSO-d$_6$) δ 8.03 (d, 1H), 7.79 (d, 1H), 7.40-7.31 (m, 2H), 7.17-7.07 (m, 2H), 6.59 (d, 1H), 3.47 (dq, 1H), 3.33 (s, 3H), 3.17 (d, 1H), 2.75 (d, 1H), 2.62 (s, 1H), 2.25-2.14 (m, 2H), 2.03 (d, 2H), 1.94 (d, 2H), 1.82-1.71 (m, 1H), 1.62 (s, 1H), 1.53 (s, 1H), 1.37 (s, 9H).

Isomer 2 LCMS: m/z (ESI), [M+H]$^+$=491; 1H NMR (400 MHz, DMSO-d) δ 8.04 (d, 1H), 7.80 (d, 1H), 7.40-7.32 (m, 1H), 7.11 (t, 2H), 6.60 (d, 1H), 3.44 (d3H), 3.17 (m, 1H), 2.52 (s, 5H), 2.36-2.14 (m, 2H), 2.00 (s, 1H), 1.89 (s, 1H), 1.84-1.70 (m, 2H), 1.67 (d, 1H), 1.55 (s, 1H), 1.36 (s, 9H).

Step 2. 1-[2-(4-chloropyridazin-3-yl)oxy-4-(4-fluorophenyl)cyclopentyl]piperidin-3-amine Compound 23

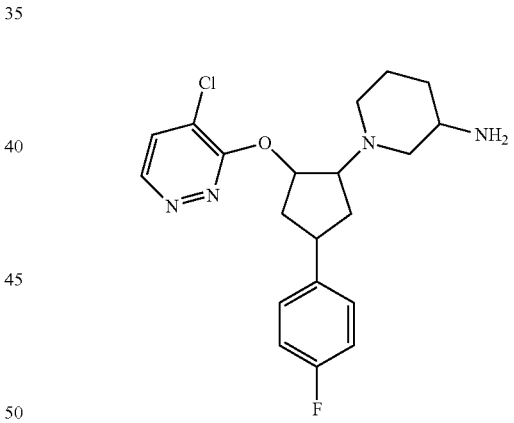

To a solution of isomer 2 (240 mg, 0.49 mmol) in DCM (10 mL) was added TFA (1 mL, 0.49 mmol). The resulting solution was stirred at rt for 30 minutes and then the solvent was evaporated. The mixture was adjusted to pH=8 with NH$_3$.H$_2$O. Preparative HPLC [(XBridge Prep OBD C18 Column 30×150 mm 5 μm; Mobile Phase A: Water (0.05% aq. NH$_3$), Mobile Phase B: MeCN; Flow rate: 55 ml/min; Gradient: 35% B to 40% B in 7 min; 254/220 nm; Rt: 5.53 min) gave Compound 23 (128 mg, 67.0%) as a white solid, which proved the more potent isomer. LCMS: m/z (ESI), [M+H]$^+$=391; 1H NMR (300 MHz, CD$_3$OD) δ 8.00 (d, 1H), 7.66 (d, 1H), 7.38-7.24 (m, 2H), 7.10-6.95 (m, 2H), 5.71 (ddd, 1H), 3.56 (dt, 2H), 2.98 (d, 1H), 2.81 (t, 2H), 2.47-2.00 (m, 4H), 1.94-1.34 (m, 5H), 1.11 (d, 1H). 19F NMR (282 MHz, CD$_3$OD) δ −119.158.

Compound 24

Step 1. tert-butyl (3R,5R)-1-(2-(6-cyanopyridazin-3-yloxy)-4-(4-fluorophenyl)cyclopentyl)-5-fluoropiperidin-3-ylcarbamate A solution of F2b (26 g, 65.58 mmol) in THF (300 ml) was cooled to 0° C. then treated with sodium hydride (4.72 g, 196.73 mmol), and after 10 mins, 6-chloropyridazine-3-carbonitrile (10.98 g, 78.69 mmol). The resulting mixture was stirred at 0° C. for 30 minutes, and rt for 30 minutes. After standard work up, the crude product was purified by flash C18-flash chromatography (0 to 40% MeCN in water (0.5% TFA)). tert-butyl (3R, 5R)-1-(2-(6-cyanopyridazin-3-yloxy)-4-(4-fluorophenyl)cyclopentyl)-5-fluoropiperidin-3-ylcarbamate (20.00 g, 61.1%) was obtained as a white solid. The product was further purified by Waters SFC 350 Preparative System [(Column: Lux 5 um Cellulose-4, 5*25 cm, 5 μm; Mobile Phase A: $CO_2$: 60%, Mobile Phase B: MeOH: 40%; Flow rate: 150 ml/min; 230 nm; RT1:6.52; RT2:7.27)] to afford isomer 1: (7.00 g, 96.8% ee) and isomer2: (10.00 g, 95.5% ee) as white solids. LCMS: m/z (ESI), $[M+H]^+$=500.

Step 2. 6-[2-(3-amino-5-fluoro-1-piperidyl)-4-(4-fluorophenyl)cyclopentoxy]pyridazine-3-carbonitrile Compound 24

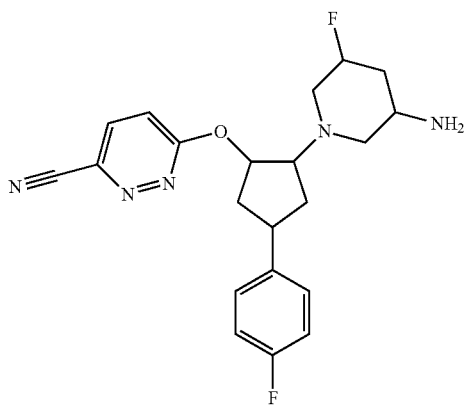 [SMILES: N#Cc1ccc(OC2CC(c3ccc(F)cc3)CC2N2CC(N)CC(F)C2)nn1]

Dimethylsulfane (30 ml, 391.94 mmol) and TFA (30 mL, 392.03 mmol) were added dropwise at batches to isomer 2 obtained in the preceding experiment (10 g, 20.02 mmol) in DCM (100 ml) at 25° C. The resulting mixture was stirred at 25° C. for 2 h and then the solvent was removed under reduced pressure. C18-flash chromatography (10 to 30% MeCN in water (0.05% TFA)) afforded Compound 24 (9.00 g, 82%) as a white solid. LCMS: m/z (ESI), $[M+H]^+$=400; 1H NMR (300 MHz, $CD_3OD$) δ 8.03 (d, 1H), 7.46-7.23 (m, 3H), 7.14-6.97 (m, 2H), 5.87 (d, 1H), 5.07 (s, 1H), 3.65 (s, 2H), 3.51-3.36 (m, 1H), 3.31 (d, 2H), 3.08-2.83 (m, 1H), 2.73 (d, 1H), 2.50 (s, 1H), 2.29 (tt, 3H), 1.93 (dq, 2H). 19F NMR (376 MHz, $CD_3OD$) δ −77.3, −118.76, −185.06.

Compound 25

Step 1. tert-butyl (3R)-1-(2-(5-chloropyridazin-3-yloxy)-4-(4-fluorophenyl) cyclopentyl) piperidin-3-yl carbamate DTAD (487 mg, 2.11 mmol) was added to 5-chloropyridazin-3(2H)-one (207 mg, 1.59 mmol), F2a (400 mg, 1.06 mmol) and $PPh_3$ (554 mg, 2.11 mmol) in DCM (20 mL). The resulting mixture was stirred at 30° C. for 2 hours and then the solvent was removed under reduced pressure. C18 flash column chromatography (40 to 42% MeCN in water (modified with 0.1% aq. $NH_3$) gave the desired product (450 mg, 87%) as a yellow solid. LCMS: m/z (ESI), $[M+H]^+$=492; 1H NMR (300 MHz, $CD_3OD$) δ 1.20-1.32 (m, 1H), 1.44 (d, 10H), 1.49 (d, 1H), 1.62-1.94 (m, 4H), 1.95-2.17 (m, 3H), 2.16-2.46 (m, 2H), 2.68-2.98 (m, 2H), 3.55 (dt, 3H), 5.64 (tt, 1H), 6.97-7.15 (m, 3H), 7.26-7.37 (m, 2H), 8.12 (t, 1H).

Step 2. tert-butyl (3R)-1-(4-(4-fluorophenyl)-2-(5-fluoropyridazin-3-yloxy) cyclopentyl) piperidin-3-yl carbamate KF (237 mg, 4.07 mmol) was added to the foregoing piperidin-3-ylcarbamate compound (400 mg, 0.81 mmol) in DMSO (10 mL). The resulting mixture was stirred at 100° C. for 72 h then diluted with DCM (20 ml), and washed with water (25 mL×3). The organic layer was dried over $Na_2SO_4$, filtered and evaporated to afford crude product. Preparative HPLC [XBridge Prep OBD C18 Column 19*250 mm, 5 μm; Mobile Phase A: Water (0.05% aq. $NH_3$), Mobile Phase B: MeCN; Flow rate: 20 ml/min; Gradient: 66% B to 66% B in 8 min; 220,254 nm; Rt: 6.57-7.18 mins] gave tert-butyl (3R)-1-(4-(4-fluorophenyl)-2-(5-fluoropyridazin-3-yloxy) cyclopentyl)piperidin-3-ylcarbamate (60.0 mg, 15.52%) as a yellow solid. LCMS: m/z (ESI), $[M+H]^+$=475.

Step 3. 1-[4-(4-fluorophenyl)-2-(5-fluoropyridazin-3-yl)oxy-cyclopentyl]piperidin-3-amine Compound

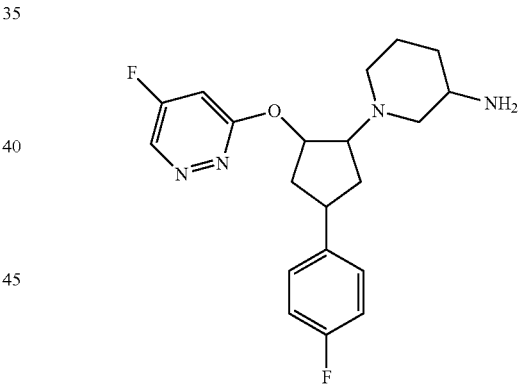

TFA (3 ml, 0.13 mmol) was added to the carbamate obtained above (60 mg, 0.13 mmol) in DCM (15 mL). The resulting solution was stirred at 25° C. for 2 hours and the solvent was removed under reduced pressure. Preparative HPLC [Column XSelect CSH Prep C18 OBD Column, 5 μm, 19*150 mm; Mobile Phase A: Water (0.05% TFA), Mobile Phase B: MeCN; Flow rate: 25 mL/min; Gradient: 15% B to 25% B in 7 min; 254; 220 nm; Rt: 4.42 min] gave compound 25, (R)-1-((1S,2S,4R)-4-(4-fluorophenyl)-2-(5-fluoropyridazin-3-yloxy)cyclopentyl)piperidin-3-amine, (20.00 mg, 42.2%) as a colourless oil. LCMS: m/z (ESI), $[M+H]^+$=375; 1H NMR (300 MHz, $CD_3OD$) δ 8.23 (d, 1H), 7.30-7.34 (m, 2H), 7.01-7.07 (m, 2H), 6.77 (d, 1H), 5.86 (s, 1H), 4.11 (s, 1H), 3.08-3.58 (m, 4H), 2.89-2.91 (m, 2H), 2.59 (s, 1H), 2.32-2.36 (m, 1H), 2.17-2.27 (m, 1H), 1.85-2.03 (m, 3H), 1.79-1.82 (m, 1H), 1.63-1.66 (m, 1H). 19F NMR (300 MHz, $CD_3OD$) δ −77.16, −111.97.

Compound 26

Step 1. tert-butyl (3R)-1-(2-(5-cyanopyridin-2-yloxy)-4-(4-fluorophenyl)cyclopentyl)piperidin-3-ylcarbamate To a mixture of F2a (360 mg, 0.95 mmol), 6-hydroxynicotinonitrile (114 mg, 0.95 mmol), PPh$_3$ (499 mg, 1.90 mmol) in THF (25 ml), was added DTAD (438 mg, 1.90 mmol). After stirring for 16 h the solvent was evaporated. The residue was purified by preparative TLC (EtOAc:petroleum ether=1:2), to afford tert-butyl the product (280 mg, 61.3%) as a yellow oil. Prep-HPLC to afforded fraction 1 (120 mg, 33.8%) as a white solid and fraction 2 (70.0 mg, 19.69%) as a white solid.

Fraction 1: 1H NMR (300 MHz, CDCl$_3$) δ 8.67-8.76, 8.13 (1H, s), 7.61-7.71 (1H, m), 7.28-7.40 (2H, m), 7.12 (2H, t), 6.61 (1H, s), 6.48 (1H, dd), 5.33 (1H, s), 3.54 (2H, d), 3.26 (2H, s), 2.77 (1H, s), 2.15 (4H, s), 1.61 (7H, s), 1.35 (9H, s), 1.20 (1H, m). LCMS: m/z (ESI), [M+H]=481.

Fraction 2: 1H NMR (300 MHz, CDCl$_3$) δ 1.33 (9H, d), 1.75 (4H, s), 2.13 (3H, s), 5.69 (1H, s), 6.99-7.19 (3H, m), 7.29-7.40 (2H, m), 8.17 (2H, d), 8.72 (1H, s); LCMS: m/z (ESI), [M+H]$^+$=481.

Step 2. 6-(2-((R)-3-aminopiperidin-1-yl)-4-(4-fluorophenyl)cyclopentyloxy)nicotinonitrile Compound 26

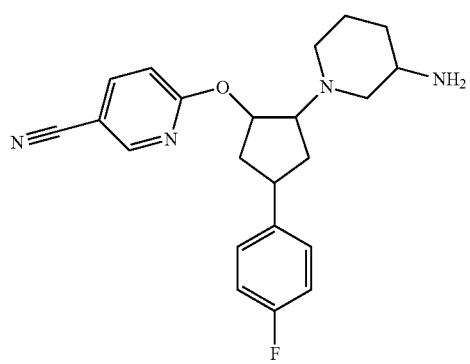 [SMILES: N#Cc1ccc(OC2CC(c3ccc(F)cc3)CC2N2CCCC(N)C2)nc1]

To a solution of the above fraction 2 (70 mg, 0.15 mmol) in DCM (15 ml), was added TFA (0.15 mL, 1.95 mmol). The reaction mixture was stirred at 25° C. for 1 hour and concentrated to dryness. The residue was purified by preparative HPLC, [water (containing 0.05% NH$_3$) and MeCN gradient) to give a white solid (50.0 mg, 90%), which was further purified by prep-chiral-HPLC to afford 6-(2-((R)-3-aminopiperidin-1-yl)-4-(4-fluorophenyl)cyclopentyloxy) nicotinonitrile isomer 1, Compound 26 (22.70 mg, 32.4%) as a white solid and isomer 2 (15.50 mg, 22.14%). Compound 26 showed: 1H NMR (300 MHz, CD$_3$OD) δ 1.24 (1H, t), 1.49-1.81 (3H, m), 1.89 (1H, dq), 2.02-2.29 (4H, m), 2.34-2.49 (1H, m), 2.79-2.93 (2H, m), 3.01 (1H, d), 3.11-3.41 (2H, m), 5.60 (1H, ddd), 6.88-7.09 (3H, m), 7.22-7.36 (2H, m), 7.98 (1H, dd), 8.56 (1H, dd). LCMS: m/z (ESI), [M+H]$^+$=381.

Isomer 2: 1H NMR (300 MHz, DMSO-d$_6$) δ 1.17 (1H, td), 1.53-2.28 (9H, m), 2.32-2.47 (1H, m), 2.78-2.93 (2H, m), 3.01 (1H, d), 3.09-3.39 (1H, m), 5.58 (1H, d), 6.89-7.07 (3H, m), 7.28 (2H, dd), 7.97 (1H, dt), 8.55 (1H, d). LCMS: m/z (ESI), [M+H]$^+$=381.

Compound 27

Step 1. tert-butyl (3R)-1-(2-(6-cyanopyridin-3-yloxy)-4-(4-fluorophenyl) cyclopentyl) piperidin-3-yl carbamate F2a (226.8 mg, 0.60 mmol), 5-hydroxypicolinonitrile (86 mg, 0.72 mmol) and Ph$_3$P (393 mg, 1.50 mmol) in DCM (10 ml) were reacted at 0° C. with DTAD (276 mg, 1.20 mmol). The reaction was allowed to warm to rt over 2 h. After standard work up C18 flash column chromatography, (0 to 45% MeCN in water (0.1M aq. NH$_3$)) gave tert-butyl (3R)-1-(2-(6-cyanopyridin-3-yloxy)-4-(4-fluorophenyl)cyclopentyl) piperidin-3-yl carbamate (160 mg, 55.6%) as a light red solid. LCMS: m/z (ESI), [M+H]$^+$=481.30. Preparative chiral-HPLC [(Column: Chiralpak IA, 2*25 cm, 5 μm; Mobile Phase: Phase A: Hexanes-HPLC Phase B: EtOH-HPLC Gradient; Flow rate: 20 mL/min; Gradient: A:B=90:10 in 12.5 min; 254/220 nm; RT1:11.13; RT2:14.44)] afforded two fractions containing isomer 1 (30 mg, 0.06 mmol) and isomer 2 (30 mg, 0.06 mmol) as white solids.

Step 2. 6-[2-(3-amino-1-piperidyl)-4-(4-fluorophenyl)cyclopentoxy]pyridine-3-carbonitrile Compound 27

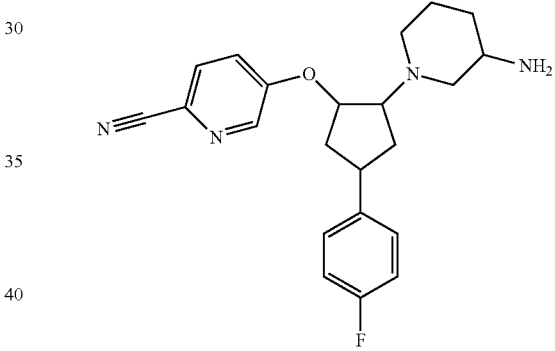

To a stirred solution of isomer 1 (30 mg, 0.06 mmol) in DCM (2 mL) was added TFA (0.66 mL) at r.t for 16 h. Purification by preparative HPLC (XBridge Prep C18 OBD column, 5μ silica, 19 mm diameter, 150 mm length, water (containing 0.05% TFA)/MeCN gradient) gave Compound 27, (24.00 mg, 90%) as a white solid which proved to be the most potent isomer. LCMS: m/z (ESI), [M+H]$^+$=381; 1H NMR (300 MHz, CD$_3$OD) δ 8.43 (s, 1H), 8.33 (s, 1H), 7.85 (d, 1H), 7.56 (d, 1H), 7.32 (dd, 2H), 7.16-6.97 (m, 2H), 4.92 (s, 2H), 3.38 (s, 2H), 2.93 (d, 1H), 2.61 (d, 3H), 2.38 (dt, 1H), 2.21 (t, 2H), 2.05-1.76 (m, 3H), 1.77-1.48 (m, 2H).

Compound 28

Step 1. tert-butyl 1-((1R)-4-(4-fluorophenyl)-2-(pyridazin-3-yloxy)cyclopentyl)piperidin-3-yl carbamate DIAD (427 mg, 2.11 mmol) PPh$_3$ (554 mg, 2.11 mmol), pyridazin-3(2H)-one (152 mg, 1.59 mmol) and F2a (400 mg, 1.06 mmol) in DCM (10 ml) were reacted under standard Mitsunobu conditions. After 2 h at rt the solvent was removed under reduced pressure. C18 flash column chromatography, (45 to 50% MeCN in water (modified with 0.1 aq. NH$_3$) gave tert-butyl ((3R)-1-(4-(4-fluorophenyl)-2-(pyridazin-3-yloxy)cyclopentyl)piperidin-3-yl)carbamate (400 mg, 83%) as a yellow solid. LCMS: m/z (ESI), [M+H]$^+$=457; 1H NMR (300 MHz, CD$_3$OD) δ 1.17-1.33 (m, 1H), 1.45 (d, 9H), 1.51-2.14 (m, 4H), 2.18-2.50 (m, 2H), 2.66-2.90 (m, 1H), 2.94 (d, 1H), 3.38 (s, 2H), 3.49-3.66 (m, 3H), 5.64-5.79 (m, 1H), 6.93-7.12 (m, 3H), 7.26-7.49 (m, 3H), 8.09 (ddd, 1H). Preparative chiral-HPLC [Chiralpak IB, eluting isocratically with 40% IPA in Hexanes (modified with 0.1% DEA) as eluent] afforded tert-butyl 1-((1R)-4-(4-fluorophenyl)-2-(pyridazin-3-yloxy)cyclopentyl)piperidin-3-ylcarbamate isomer 1 (180 mg, 45.0%, 99.5% ee) as a yellow solid and isomer 2 (180 mg, 45.0%, 99.5% ee) as a yellow solid. LCMS (for both isomers) m/z (ESI), [M+H]$^+$=457.

Step 2. 1-[4-(4-fluorophenyl)-2-pyridazin-3-yloxy-cyclopentyl]piperidin-3-amine Compound 28

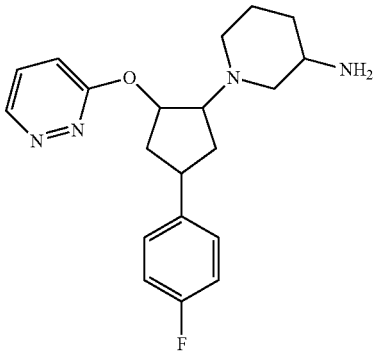 [SMILES: NC1CCCN(C2CC(c3ccc(F)cc3)CC2Oc2cccnn2)C1]

TFA (2 mL, 25.96 mmol) was added to isomer 1 obtained above (180 mg, 0.39 mmol) in DCM (10 ml). The resulting mixture was stirred at 25° C. for 2 hours. The solvent was then removed under reduced pressure and the crude product was purified by preparative HPLC [X select CSH OBD Column 30*150 mm 5 μm; Mobile Phase A: Water (0.05% TFA), Mobile Phase B: MeCN; Flow rate: 60 mL/min; Gradient: 11% B to 21% B in 7 min; 254; 220 nm; Rt: 5.57 min] to afford Compound 28 (240 mg, 70.7%) as a white solid. LCMS: m/z (ESI), [M+H]$^+$=357; 1H NMR (300 MHz, CD$_3$OD) δ 1.56-1.75 (m, 1H), 1.82-2.31 (m, 5H), 2.47 (ddd, 1H), 2.65-2.80 (m, 1H), 2.93 (t, 1H), 3.08 (t, 1H), 3.66 (dtd, 4H), 4.32 (dt, 1H), 5.99 (ddd, 1H), 6.99-7.14 (m, 3H), 7.29-7.42 (m, 2H), 7.48 (dd, 1H), 8.14 (dd, 1H). 19F NMR (300 MHz, CD$_3$OD) δ −77.173 (m, 13F), −118.211 (s, 1F).

Compound 29

Step 1. tert-butyl (3R,5R)-5-fluoro-1-(4-(4-fluorophenyl)-2-(pyrimidin-4-yloxy)cyclopentyl)piperidin-3-ylcarbamate DTAD (581 mg, 2.52 mmol) was added to F2b (500 mg, 1.26 mmol), pyrimidin-4-ol (145 mg, 1.51 mmol) and PPh$_3$ (827 mg, 3.15 mmol) in DCM (15 ml) at 0° C. over a period of 5 minutes. The resulting solution was stirred at 25° C. for 2 hours. The solvent was removed under reduced pressure. C18 flash column chromatography (40 to 50% water in MeCN) gave fraction 1 (former peak: 200 mg, 33.4%) as a colourless oil and fraction 2 (later peak: 300 mg, 50.1%) as a white solid. Fraction 2 was further separated and purified by preparative chiral-HPLC on a CHIRALPAK IA-3 column, eluting isocratically with 50% IPA in petroleum ether (modified with diethylamine) as eluent. The fractions containing the desired compound were evaporated to dryness to afford isomer 1 tert-butyl((3S,5R)-5-fluoro-1-((1S,2S,4R)-4-(4-fluorophenyl)-2-(pyrimidin-4-yloxy)cyclopentyl)piperidin-3-yl)carbamate (160 mg, 41%, 100% ee) as a white solid and isomer 2 (110 mg, 28.2%, 99.6% ee) as a white solid. LCMS for both isomers: m/z (ESI), [M+H]$^+$=475.

Step 2. 5-fluoro-1-[4-(4-fluorophenyl)-2-pyrimidin-4-yloxy-cyclopentyl]piperidin-3-amine Compound 29

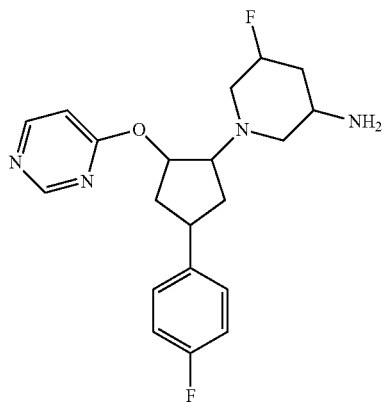 [SMILES: NC1CC(F)CN(C2CC(c3ccc(F)cc3)CC2Oc2ccncn2)C1]

TFA (3 mL, 0.34 mmol) was added to above isomer 1 (160 mg, 0.34 mmol) in DCM (15 mL). The resulting solution was stirred at 25° C. for 2 hours. Preparative HPLC [XBridge Prep OBD C18 Column 30×150 mm 5 um; Mobile Phase A: Water (0.05% aq. NH$_3$), Mobile Phase B: MeCN; Flow rate: 60 mL/min; Gradient: 28% B to 40% B in 7 min; 254/220 nm; Rt: 5.95 min] gave Compound 29 as a white solid (75.0 mg, 59.0%). LCMS: m/z (ESI), [M+H]$^+$=375; 1H NMR (300 MHz, CD$_3$OD) δ 8.75 (dd, 1H), 8.46 (dd, 1H), 7.38-7.24 (m, 2H), 7.09-6.89 (m, 3H), 5.62 (ddd, 1H), 4.90 (d, 0.5H), 4.76 (s, 0.5H), 3.35 (s, 1H), 3.30-3.01 (m, 4H), 2.51-1.96 (m, 6H), 1.77 (td, 1H), 1.44 (dt, 1H). 19F NMR (300 MHz, CD$_3$OD) δ −183.07, −119.12

Compound 30

Step 1. tert-butyl (3R)-1-(2-(5-bromopyrimidin-2-yloxy)-4-(4-fluorophenyl) cyclopentyl) piperidin-3-yl carbamate To a solution of F2a (900 mg, 2.38 mmol) in DMF (6 ml) was added NaH (190 mg, 4.76 mmol) at rt. The mixture was stirred for 3 min, then 5-bromo-2-chloropyrimidine (690 mg, 3.57 mmol). After 8 h the reaction mixture was quenched with saturated NH$_4$Cl (aq). (30 mL) and extracted with DCM (2×20 mL), the organic layer was dried over Na$_2$SO$_4$, filtered and evaporated to afford crude product. Preparative TLC (EtOAc:petroleum ether=1:2), gave the product (500 mg, 39.3%) as a white solid. LCMS: m/z (ESI), [M+H]$^+$=379.

Step 2. tert-butyl (3R)-1-(2-(5-cyanopyrimidin-2-yloxy)-4-(4-fluorophenyl)cyclopentyl) piperidin-3-yl carbamate To a solution of the above carbamate (330 mg, 0.62 mmol) in DMF (5 ml) was added Zn(CN)$_2$ (145 mg, 1.23 mmol) and zinc (4.03 mg, 0.06 mmol) at rt. Pd$_2$dba$_3$ (106.8 mg, 0.12 mmol) and dppf (137 mg, 0.25 mmol) were then added and the reaction stirred for 3 h at 120° C. After dilution with EtOAc (20 mL), and washing (water (10 mL×2), saturated brine (10 mL)), the combined organics were dried over and evaporated. The residue was purified by preparative TLC (DCM:MeOH=50:1), to afford a crude product (200 mg, 67.4%) as a yellow solid. Preparative chiral-HPLC (Column: CHIRAL Cellulose-SB size: 0.46*15 cm; 3 μm. Mobile phase: Hexanes (0.1% DEA): IPA=80:20; Flow rate: 1.0 ml/min; Detector: UV-254 nm; RT1:7.353; RT2:8.710) afforded tert-butyl (R)-1-((1S,2S,4R)-2-(5-cyanopyrimidin-2-yloxy)-4-(4-fluorophenyl)cyclopentyl)piperidin-3-ylcarbamate isomer 1 (120 mg, 57.1%, 100% ee), and isomer 2 (50.0 mg, 23.81%, 98.7% ee) as white solids. LCMS: m/z (ESI), [M+H]$^+$=482.

Step 3. 2-[2-(3-amino-1-piperidyl)-4-(4-fluorophenyl)cyclopentoxy]pyrimidine-5-carbonitrile Compound 30

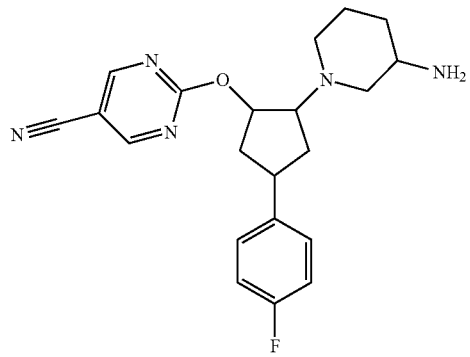 [SMILES: N#Cc1cnc(OC2CC(c3ccc(F)cc3)CC2N2CCCC(N)C2)nc1]

To a solution of the above isomer 1 (120 mg, 0.25 mmol) in DCM (2 ml) was added TFA (0.66 mL) at rt. After stirring for 16 h and standard work up the crude product was purified by preparative HPLC (Column: XSelect CSH Prep C18 OBD Column, 5 μm, 19*150 mm; Mobile Phase A: Waters (0.1% FA), Mobile Phase B: MeCN; Flow rate: 20 ml/min; Gradient: 2% B to 27% B in 7 min; 220,254 nm) to afford Compound 30 (100 mg, 93%), as a white solid, which proved to be the potent isomer. 1H NMR (300 MHz, CD$_3$OD) δ 8.98 (s, 2H), 8.31 (s, 1H), 7.32 (d, 2H), 7.04 (t, 2H), 5.59 (d, 1H), 3.42 (br s, 1H), 3.26 (s, 1H), 2.96 (d, 1H), 2.85-2.67 (m, 1H), 2.67-2.51 (m, 2H), 2.43 (d, 1H), 2.23 (d, 2H), 2.05-1.46 (m, 5H). LCMS: m/z (ESI), [M+H]$^+$=382.

Compound 31

Step 1. tert-butyl (3R)-1-(2-(5-bromopyrimidin-2-yloxy)-4-(4-fluorophenyl)cyclopentyl) piperidin-3-yl carbamate To a solution of F2a (900 mg, 2.38 mmol) in DMF (6 ml) was added NaH (190 mg, 4.76 mmol) at rt. The mixture was stirred for 3 min then 5-bromo-2-chloropyrimidine (690 mg, 3.57 mmol) was introduced. The reaction was worked up after 8 h stirring. Purification by Prep-TLC to give the product (500 mg, 39.3%) as a white solid. This crude product was further purified by preparative chiral-HPLC [(CHIRALPAK IC-3 size: 0.46*10 cm; 3 μm. Mobile phase: Hexanes (0.1% DEA): EtOH=80:20; Flow rate: 1 mL/min;

Detector: 254 nm; RT1:4.759; RT2:5.595) to afford tert-butyl (3R)-1-(2-(5-cyanopyrazin-2-yloxy)-4-(4-fluorophenyl)cyclopentyl)piperidin-3-ylcarbamate isomer 1 (100 mg, 55.6%, 99.9% ee), and isomer 2 (50.0 mg, 27.8%, 100% ee) as white solid.

Step 2. 5-[2-(3-amino-1-piperidyl)-4-(4-fluorophenyl)cyclopentoxy]pyrazine-2-carbonitrile Compound 31

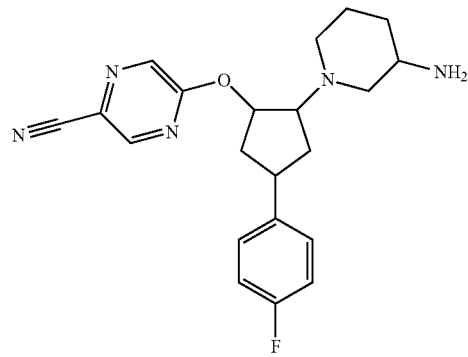 [SMILES: N#Cc1cnc(OC2CC(c3ccc(F)cc3)CC2N2CCCC(N)C2)cn1]

To a solution of isomer 2 obtained above (50 mg, 0.10 mmol) in DCM (2 ml) was added TFA (0.5 mL, 6.5 mmol) at rt. The reaction was stirred for 2 h then subjected to standard work up. The crude product was purified by preparative HPLC [XBridge Prep C18 OBD Column, 5 μm, 19*150 mm; Mobile Phase A: Waters (10 mmol/L NH$_4$HCO$_3$), Mobile Phase B: MeCN; Flow rate: 20 ml/min; Gradient: 20% B to 33% B in 20 min; 254/220 nm to give Compound 31 (30.0 mg, 76%) as a white solid LCMS: m/z (ESI), [M+H]$^+$=382.4; 1H NMR (400 MHz, CD$_3$OD) δ 8.64 (s, 1H), 8.36 (s, 1H), 7.30 (dd, 2H), 7.04 (t, 2H), 5.65-5.53 (m, 1H), 3.51-3.35 (m, 3H), 2.93 (d, 1H), 2.71 (d, 1H), 2.57 (d, 2H), 2.42 (s, 1H), 2.20 (dd, 2H), 2.02-1.89 (m, 1H), 1.89-1.72 (m, 2H), 1.65 (d, 2H).

Compound 32

Step 1. tert-butyl (3R)-1-(2-(2-cyanopyrimidin-5-yloxy)-4-(4-fluorophenyl) cyclopentyl) piperidin-3-yl carbamate To a solution of F2a (260 mg, 0.69 mmol), 5-hydroxypyrimidine-2-carbonitrile (100 mg, 0.82 mmol) and Ph$_3$P (270 mg, 1.03 mmol) in DCM (10 mL) at 0° C., was added DTAD (237 mg, 1.03 mmol). The mixture was stirred for 2 h at 25° C. The reaction mixture was quenched with saturated NaHCO$_3$ (100 mL), extracted with DCM (2×50 ml), then dried and evaporated to afford an orange gum. Preparative HPLC (XBridge Prep C18 OBD column, 5 μm silica, 19 mm diameter, 150 mm length, water (containing 0.05% NH$_3$)/MeCN gradient) gave the product (190 mg, 57.4%) as a white solid. LCMS: m/z (ESI), [M+H]$^+$=482. Preparative chiral-HPLC [Column: CHIRALPAK IC, 2.0 cm I.D*25 cm L; Mobile Phase A: Hexanes-HPLC, Mobile Phase B: EtOH-HPLC; Flow rate: 20 ml/min; Gradient: A:B=85:15 in 24 min; gave tert-butyl (3R)-1-(2-(2-cyanopyrimidin-5-yloxy)-4-(4-fluorophenyl)cyclopentyl)piperidin-3-ylcarbamate isomer 1 (first fraction: 95 mg, 50.0%, 100% ee) and isomer 2 (second fraction; 100 mg, 52.6%, 88.6% ee).

Step 2. 5-[2-(3-amino-1-piperidyl)-4-(4-fluorophenyl)cyclopentoxy]pyrimidine-2-carbonitrile Compound 32

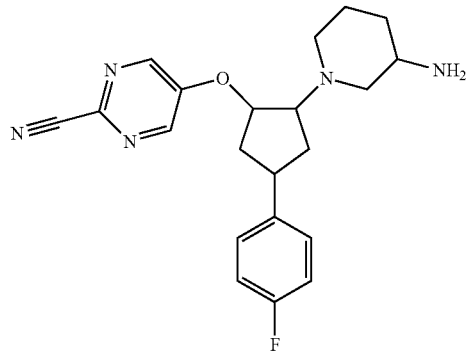 [SMILES: N#Cc1ncc(OC2CC(c3ccc(F)cc3)CC2N2CCCC(N)C2)cn1]

To a solution of the isomer 2 (100 mg, 0.21 mmol) obtained above in DCM (10 mL) was added TFA (0.66 mL) at 25° C. The reaction mixture was stirred for 16 h then worked up. The crude product was purified by preparative HPLC (Column: XSelect CSH Prep C18 OBD Column, 5 μm, 19 mm×150 mm; Mobile Phase A: Waters (0.05% TFA), Mobile Phase B: MeCN; Flow rate: 20 mL/min; Gradient: 10% B to 32% B in 7 min; 254; 220 nm) to give Compound 32 (80 mg, 51.6%) as a white solid. LCMS: m/z (ESI), $[M+H]^+$=382; 1H NMR (300 MHz, $CD_3OD$) δ 8.63 (s, 2H), 7.42-7.26 (m, 2H), 7.13-6.97 (m, 2H), 5.57-5.40 (m, 1H), 4.08 (ddd, 1H), 3.76-3.36 (m, 5H), 3.11 (q, 2H), 2.63 (ddd, 1H), 2.35 (dtd, 2H), 2.23-2.01 (m, 3H), 2.01-1.81 (m, 1H), 1.70 (dd, 1H). 19F NMR (282 MHz, $CD_3OD$) δ −77.14, −118.01.

X-Ray Crystallographic Studies of Compound 10, Form A.

The sample of compound 10 obtained as described above was mounted on single silicon crystal (SSC) wafer mount and powder X-ray diffraction was recorded with a Theta-Theta PANalytical X'Pert PRO (wavelength of X-rays 1.5418 Å nickel-filtered Cu radiation, Voltage 45 kV, filament emission 40 mA). Automatic variable divergence and anti-scatter slits were used and the samples were rotated during measurement. Samples were scanned from 2-50° 2Theta using a 0.013° step width and a 233 seconds step measurement time using a PIXCEL detector (active length 3.35° 2Theta).

The 13 most prominent X-Ray powder diffraction peaks for Compound 10, Form A, are reported in Table 1 above. relative intensity values of Table 1 are assigned according to the definitions of Table 3 below.

TABLE 3

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with fixed slits

The invention claimed is:

1. A compound of Formula I

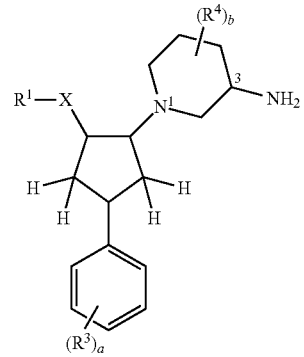

Formula I wherein:
X is $NR^2$, and wherein N, $R^1$ and $R^2$ together form 1,2,4-triazole, 1,2,3-triazole, pyrazole, pyrrole, imidazole or tetrazole that is optionally substituted with one or two substituents Y that are independently selected from F, Cl, CN, or Me;
$R^3$ is independently selected from F, Cl, CN, methyl, methoxy, hydroxy and ethynyl;
$R^4$ is independently selected from F or Cl attached to C2, C4 or C5 of the piperidine ring; and
the integers a and b are independently selected from 0, 1 or 2;
or a pharmaceutically acceptable salt thereof.

2. Compound according to claim 1 in which the piperidine group and the group $XR^1$ are in the trans-configuration.

3. Compound according to claim 1 wherein the piperidine and the phenyl group are in the cis-configuration.

4. Compound according to claim 1 wherein a substituent $R^3$ is located para-to the bond to the cyclopentane ring.

5. Compound according to claim 4 wherein the substituent $R^3$ is F and a=1.

6. Compound according to claim 1, wherein N, $R^1$ and $R^2$ together form 1,2,4-triazole, 1,2,3-triazole, pyrazole, pyrrole, imidazole or tetrazole that is unsubstituted.

7. Compound according to claim 1 selected from:
1-[4-(4-fluorophenyl)-2-(2H-1,2,3-triazol-2-yl)cyclopentyl]piperidin-3-amine;
1-[2-(3-amino-1-piperidyl)-4-(4-fluorophenyl)cyclopentyl]pyrazole-4-carbonitrile;
1-[2-(3-amino-1-piperidyl)-4-(4-fluorophenyl)cyclopentyl]pyrazole-3-carbonitrile;
1-[2-(3-amino-1-piperidyl)-4-(4-fluorophenyl)cyclopentyl]pyrrole-3-carbonitrile;
1-[2-(3-amino-1-piperidyl)-4-(4-fluorophenyl)cyclopentyl]-1H-1,2,3-triazole-4-carbonitrile;
1-[2-(3-amino-5-fluoro-1-piperidyl)-4-(4-fluorophenyl)cyclopentyl]pyrazole-4-carbonitrile;
1-[2-(3-amino-4,4-difluoro-1-piperidyl)-4-(4-fluorophenyl)cyclopentyl]pyrazole-4-carbonitrile;
1-[4-(4-fluorophenyl)-2-pyrazol-1-yl-cyclopentyl]piperidin-3-amine;
5-fluoro-1-[4-(4-fluorophenyl)-2-pyrazol-1-yl-cyclopentyl]piperidin-3-amine;
5-fluoro-1-[4-(4-fluorophenyl)-2-(1,2,4-triazol-1-yl)cyclopentyl]piperidin-3-amine;

5-fluoro-1-[4-(4-fluorophenyl)-2-(tetrazol-2-yl)cyclopentyl]piperidin-3-amine;

1-[4-(4-fluorophenyl)-2-(tetrazol-2-yl)cyclopentyl]piperidin-3-amine;

1-[2-(3-amino-1-piperidyl)-4-(4-fluorophenyl)cyclopentyl]-1,2,4-triazole-3-carbonitrile;

or a pharmaceutically acceptable salt thereof.

8. (3R,5R)-5-fluoro-1-((1R,2R,4S)-4-(4-fluorophenyl)-2-(1H-1,2,4-triazol-1-yl)cyclopentyl)piperidin-3-amine, or a pharmaceutically acceptable salt thereof.

9. A pharmaceutical composition comprising a compound or a pharmaceutically acceptable salt thereof according to claim 1, and at least one pharmaceutically acceptable diluent, excipient or inert carrier.

* * * * *